(12) United States Patent
Sang et al.

(10) Patent No.: US 9,549,911 B2
(45) Date of Patent: Jan. 24, 2017

(54) GINGER METABOLITES AND USES THEREOF

(71) Applicant: North Carolina A&T State University, Greensboro, NC (US)

(72) Inventors: Shengmin Sang, Concord, NC (US); Huadong Chen, Kannapolis, NC (US); Yingdong Zhu, Kannapolis, NC (US)

(73) Assignee: North Carolina A&T State University, Greensboro, NC (US)

( * ) Notice: Subject to any disclaimer, the term of this patent is extended or adjusted under 35 U.S.C. 154(b) by 0 days.

(21) Appl. No.: 15/010,011

(22) Filed: Jan. 29, 2016

(65) Prior Publication Data

US 2016/0235697 A1    Aug. 18, 2016

Related U.S. Application Data

(62) Division of application No. 14/134,504, filed on Dec. 19, 2013, now Pat. No. 9,272,994.

(60) Provisional application No. 61/790,281, filed on Mar. 15, 2013, provisional application No. 61/739,169, filed on Dec. 19, 2012.

(51) Int. Cl.
| | | |
|---|---|---|
| *C07D 487/04* | (2006.01) |
| *A61K 31/198* | (2006.01) |
| *A61K 36/9068* | (2006.01) |
| *C07D 519/00* | (2006.01) |

(52) U.S. Cl.
CPC ......... *A61K 31/198* (2013.01); *A61K 36/9068* (2013.01); *C07D 487/04* (2013.01); *C07D 519/00* (2013.01)

(58) Field of Classification Search
None
See application file for complete search history.

(56) References Cited

U.S. PATENT DOCUMENTS

| | | | | |
|---|---|---|---|---|
| 2006/0018867 A1* | 1/2006 | Kawasaki | ............... | A61K 8/898 424/70.122 |
| 2010/0286283 A1 | 11/2010 | Ishiguro et al. | | |
| 2011/0136916 A1 | 6/2011 | Li et al. | | |

OTHER PUBLICATIONS

"Pharmacokinetics of [6]-Shogaol, a Pungent Ingredient of Zingiber Officinale Roscoe (Part I)." Asami, A., Tsutomu S., Yasuharu M., Takayuki A., Shuichi T., Takashi A., Ken-Ichi M., and Masaki A., J. of Natural Medicines 64, No. 3 (2010).
"Synthesis of Some Novel Potent and Selective Catechol O-methyltransferase Inhibitors," Backstrom, R.; Honkanen, E.; Pippuri, A.; Kairisalo, P,; Pystynen, J.; Heinola, K.; Nissinen, E.; Linden, I. B.; Mannisto, P. T.; Kaakkola, S., J. Med. Chem. 32 (1989).
"6-Shogaol Rich Extract From Ginger Up-regulates the Antioxidant Defense Systems in Cells and Mice," Bak, M. J., Ok, S., Jun, M., and Jeong, W. S., Molecules 17 (2012).
"Update on the Chemopreventive Effects of Ginger and its Phytochemicals," Baliga, M. S., Haniadka, R., Pereira, M. M., D'Souza, J. J., Pallaty, P. L., Bhat, H. P., & Popuri, S., Critical Reviews in Food Science and Nutrition, (2011) 51(6).
"6-Shogaol (Alkanone From Ginger) Induces Apoptotic Cell Death of Human Hepatoma p53 Mutant Mahlavu Subline Via an Oxidative Stress-mediated Caspase-dependent Mechanism," Chen, C-Y., Liu, T-Z., Liu, Y-W., Tseng, W-C, Liu, R.H., Lu, F-J., Lin, Y-S., Kuo, S-H., Chen, C-H., J. Agric. Food Chem. (2007).
"Dietary Cancer-chemopreventive Compounds: From Signaling and Gene Expression to Pharmacological Effects," Chen, C., and Kong, A. N., Trends Pharmacol. Sci. (2005) 26.
"Effect of [6]-Shogaol on Cytosolic Ca2+ Levels and Proliferation in Human Oral Cancer Cells (OC2)," Chen, C.Y., Yang, Y.H. and Kuo, S.Y., J. Nat. Prod., (2010) 73(8).
"[10]-Gingerdiols as the Major Metabolites of [10]-Gingerol in Zebrafish Embryos and in Humans and Their Hematopoietic Effects in Zebrafish Embryos," Chen, H.; Soroka, D. N.; Haider, J.; Ferri-Lagneau, K. F.; Leung, T., J. Agric. Food Chem. (2013) 61.
"Cysteine-conjugated Metabolite of Ginger Component [6]-Shogaol Serves as a Carrier of [6]-Shogaol in Cancer Cells and in Mice," Chen, H.; Soroka, D. N.; Zhu, Y.; Hu, Y.; Chen, X.; Sang, S., Chem. Res. Toxicol. (2013) 26.
"Identification of Phase II Metabolites of Thiol-conjugated [6]-Shogaol in Mouse Urine Using High-performance Liquid Chromatography Tandem Mass Spectrometry," Chen, H., and Sang, S., *Journal of Chromatography B* 907 (2012).
"Characterization of Thiol-conjugated Metabolites of Ginger Components Shogaols in Mouse and Human Urine and Modulation of the Glutathione Levels in Cancer Cells by [6]-Shogaol," Chen, H., Soroka, D.N., Hu, Y., Chen, X., and Sang, S., *Molecular Nutrition & Food Research* 57, No. 3 (2013).
"Ginger Compound [6]-Shogaol and Its Cysteine-Conjugated Metabolite (M2) Activate Nrf2 in Colon Epithelial Cells in Vitro and in Vivo," Chen, H., Fu, J., Chen, H., Hu, Y., Soroka, D.N., Prigge, J.R., Schmidt, E.E., Yan, F., Major, M., Chen, X., and Sang, S., *Chemical Research in Toxicology* 27, No. 9 (2014).
"Metabolism of [6]-Shogaol in Mice and in Cancer Cells," Chen, H., L.v, L., Soroka, D.N., Warin, R.F., Parks, T.A., Hu, Y., Zhu, Y., Chen, X., and Sang, S., *Drug Metabolism and Disposition* 40, No. 4 (2012).
"Effects of Ginger Supplementation on Cell-cycle Biomarkers in the Normal-appearing Colonic Mucosa of Patients at Increased Risk for Colorectal Cancer: Results From a Pilot, Randomized, and Controlled Trial," Citronberg, J., Bostick, R., Ahearn, T., Turgeon, D.K., Ruffin, M.T., Djuric, Z., Sen, A., Brenner, D.E., and Zick, S.M., Cancer Prevention Research 6, No. 4 (2013).
"Plant Catechols and Their S-glutathionyl Conjugates as Antinitrosating Agents: Expedient Synthesis and Remarkable Potency of 5-S-glutathionylpiceatannol," De Lucia, M.; Panzelia, L.; Pezzella, A.; Napolitano, A.; D'Ischia, M., Chem, Res. Toxicol. (2008) 21.

(Continued)

*Primary Examiner* — Kamal Saeed
(74) *Attorney, Agent, or Firm* — MacCord Mason PLLC

(57) ABSTRACT

The present application generally relates to the use of metabolites of ginger and analogs thereof for the treatment and prevention of diseases, including but not limited to, cancer.

12 Claims, 12 Drawing Sheets

(56) References Cited

OTHER PUBLICATIONS

"Sulforaphane Homologues: Enantiodivergent Synthesis of Both Enantiomers, Activation of the Nrf2 Transcription Factor and Selective Cytotoxic Activity," Elhalem, E.; Recio, R.; Werner, S.; Lieder, F.; Calderon-Montano, J. M.; Lopez-Lazaro, M.; Fernandez, I.; Khiar, N., Eur. J. Med. Chem. (2014) 87C.

"Trapping of 4-hydroxynonenal by Glutathione Efficiently Pevents Formation of DNA Adducts in Human Cells," Falletti, O., Cadet, J., Favier, A., Douki, T., Free Radic. Biol. Med. (2007) 42.

"Ginger Extract Consumption Reduces Plasma Cholesterol, Inhibits LDL Oxidation and Attenuates Development of Atherosclerosis in Atherosclerotic, Apolipoprotein E-deficient Mice," Fuhrman, B.; Rosenblat, M.; Hayek, T.; Coleman, R.; Aviram, M., J. Nutr. (2000) 130.

"Shogaols at Proapoptotic Concentrations Induce G2/M Arrest and Aberrant Mitotic Cell Death Associated with Tubulin Aggregation," Gan, F-F, Nagle, A.A. Ang, X., Ho, O.H., Tan, S-H., Yang, H., Chui, W-K., Chew, E-H., Apoptosis (2011) 16, No. 8.

"A Novel Shogaol Analog Suppresses Cancer Cell Invasion and Inflammation, and Displays Cytoprotective Effects Through Modulation of NF-κB and Nrf2-Keap1 Signaling Pathways," Gan, F-F., Ling, H., Ang, X., Reddy, S.A., Lee, S.S.H., Yang, H., Tan, S-H., Hayes, J.D., Chui, W-K., Chew, E-H., *Toxicology and Applied Pharmacology* (2013)272, No. 3.

"Growth Inhibition of Human Non-small Lung Cancer Cells h460 by Green Tea and Ginger Polyphenols," Hessien, M., El-Gendy, S., Donia, T., & Abou Sikkena, M., Anti-Cancer Agents in Medicinal Chemistry (Formerly Current Medicinal Chemistry-Anti-Cancer Agents), (2012) 12(4).

"6-Shogaol Induces Apoptosis in Human Hepatocellular Carcinoma Cells and Exhibits Anti-tumor Activity in Vivo Through Endoplasmic Reticulum Stress," Hu, R., Zhou, P., Peng, Y. B., Xu, X. Ma, J., Liu, Q., Zhang, L., Wen, X-D., Qi, L-W., Gao, N., Li, P., PLoS One (2012) 7.

"6-Shogaol, An Active Constituent of Dietary Ginger, Induces Autophagy by Inhibiting the AKT/mTOR Pathway in Human Non-small Cell Lung Cancer A549 Cells," Hung, J. Y., Hsu, Y. L., Li, C. T., Ko, Y. C., Ni, W. C., Huang, M. S., Kuo, P. L., J. Agric. Food Chem. (2009) 57.

"Specific Reaction of Alpha,beta-unsaturated Carbonyl Compounds Such as 6-Shogaol with Sulfhydryl Groups in Tubulin Leading to Microtubule Damage," Ishiguro, K., Ando, T., Watanabe, O., Goto, H., FEBS Lett. (2008) 582.

"Ginger Ingredients Reduce Viability of Gastric Cancer Cells via Distinct Mechanisms," Ishiguro, K., Ando, T., Maeda, O., Ohmiya, N., Niwa, Y., Kadomatsu, K., & Goto, H., Biochemical and Biophysical Research Communications, (2007) 362(1).

"Profiling of the Compounds Absorbed in Human Plasma and Urine After Oral Administration of a Traditional Japanese (Kampo) Medicine, Daikenchuto," Iwabu, J., Watanabe, J., Hirakura, K., Ozaki, Y. Hanazaki, K., Drug Metab. Dispos. (2010) 38.

"Characterization of Gingerol-related Compounds in Ginger Rhizome (Zingiber Officinale Rosc.) by High-performance Liquid Chromatography/Electrospray Ionization Mass Spectrometry," Jiang, H., Solyom, A. M., Timmermann, B. N., Gang, D. R., Rapid Commun. Mass Spectrom. (2005) 19.

"Characterization and Identification of Diarylheptanoids in Ginger (Zingiber Officinale Rosc.) Using High-performance Liquid Chromatography/Electrospray Ionization Mass Spectrometry," Jiang, H., Timmermann, B. N., Gang, D. R., Rapid Commun. Mass Spectrom. (2007) 21.

"Metabolic Profiling and Phylogenetic Analysis of Medicinal Zingiber Species: Tools for Authentication of Ginger (Zingiber Officinale Rosc)," Jiang, H., Xie, Z., Koo, H. J., McLaughlin, S. P., Timmermann, B. N., Gang, D. R., Phytochemistry (2006) 67.

"Fresh Organically Grown Ginger (Zingiber Officinale): Composition and Effects on LPS-induced PGE 2 Production," Jolad, S. D., Lantz, R. C., Solyom, A. M., Chen, G. J., Bates, R. B., & Timmermann, B. N., Phytochemistry, (2004), 65(13).

"Biotransformation of the Naturally Occurring Isothiocyanate Sulforaphane in the Rat: Identification of Phase I Metabolites and Glutathione Conjugates," Kassahun, K., Davis, M., Hu, P., Martin, B., Baillie., T., Chem. Res. Toxicol. (1997) 10.

"[6]-Shogaol Inhibits Growth and Induces Spoptosis of Non-small Vell Lung Cancer Cells by Directly Regulating Akt1/2," Kim, M. O., Lee, M. H., Oi, N., Kim, S. H., Rae, K. B., Huang, Z., Kim, D. J., Reddy, K., Lee, S. Y., Park, S. J., Kim, J. Y., Xie, H., Kundu, J. K., Ryoo, Z. Y., Bode, A. M., Surh, Y. J., Dong, Z., Carcinogenesis (2014) 35.

"Peracetylation as a Means of Enhancing In Vitro Bioactivity and Bioavailability of Epigallocatechin-3-Gallate," Lambert, J. D.; Sang, S.; Hong, J.; Kwon, S. J.; Lee, M. J.; Ho, C. T.; Yang, C. S., Drug Metab. Dispos. (2006) 34.

"Plasma Cholesterol-Lowering Activity of Gingerol-and Shogaol-Enriched Extract is Mediated by Increasing Sterol Excretion," Lei, L., Liu, Y., Wang, X., Jiao, R., Ma, K.Y., Li, Y.M., Wang, L., Man, S.W., Sang, S., Huang, Y., Chen, Z-Y., J. of Agricultural and Food Chem. 62, No. 43 (2014).

"In Vitro Antioxidant and Anti-Inflammatory Activities of 1-Dehydro-[6]-Gingerdione, 6-Shogaol, 6-Dehydroshogaol and Hexahydrocurcumin," Li, F., Nitteranon, V., Tang, X., Liang, J., Zhang, G., Parkin, K. L., Hu, Q., Food Chem. (2012) 135.

"6-Shogaol, An Active Constituent of Ginger, Inhibits Breast Cancer Cell Invasion by Reducing Matrix Metalloproteinase-9 Expression Via Blockade of Nuclear Factor-kappaB Activation," Ling, H., Yang, H., Tan, S. H., Chui, W. K., and Chew, E. H., Br. J. Pharmacol. (2010) 161.

"6-Shogaol Induces Apoptosis in Human Leukemia Cells Through a Process Involving Caspase-mediated Cleavage of eLF2alpha," Liu, Q., Peng, Y. B., Zhou, P., Qi, L. W., Zhang, M., Gao, N., Liu, E. H., Li, P., Mol. Cancer (2013) 12.

"Anti-Oxidative and Anti-Inflammatory Effects of Ginger in Health and Physical Activity: Review of Current Evidence," Mashhadi, N. S., Ghiasvand, R., Askari, G., Hariri, M., Darvishi, L., Mofid, M. R., Int, J. Prev. Med. (2013) 4.

"Electrophiles in Foods: The Current Status of Isothiocyanates and Their Chemical Biology," Nakamura, Y., Miyoshi, N., Biosci. Biotechnol. Biochem. (2010) 74.

"6-Shogaol Suppressed Lipopolysaccharide-induced Up-expression of iNOS and COX-2 in Murine Macrophages," Pan, M. H.; Hsieh, M. C.; Hsu, P. C.; Ho, S. Y.; Lai, C. S.; Wu, H.; Sang, S.; Ho, C. T., Mol. Nutr. Food Res. (2008) 52.

"6-Shogaol Induces Apoptosis in Human Colorectal Carcinoma Cells Via ROS Production, Caspase Activation, and GADD 153 Expression," Pan, M-H., Hsieh, M.C., Kuo, J.M., Lai, C.S., Wu, H., Sang, S., Ho, C.T., Molecular Nutrition & Food Research 52, No. 5 (2008).

"6-Shogaol, An Active Compound of Ginger, Protects Dopaminergic Neurons in Parkinson's Disease Models Via Antineuroinflammation," Park, G., Kim, H. G., Ju, M. S., Ha, S. K., Park, Y., Kim, S. Y., Oh, M. S., Acta Pharmacol. Sin. (2013) 34.

"TBK1—Targeted Suppression of TRIF-Dependent Signaling Pathway of Toll-like Receptors by 6-Shogaol, An Avtive Component of Ginger," Park., S.J., Lee, M. Y., Son, B. S., Youn, H. S., Biosci., Biotechnol., Biochem. (2009) 73.

"Ginger Inhibits Cell Growth and Modulates Angiogenic Factors in Ovarian Cancer Cells," Rhode, J.; Fogoros, S.; Zick, S.; Wahl, H.; Griffith, K., A.; Huang, J.; Liu, J. R., BMC Complementary Altern. Med. (2007) 7.

"Enhanced Glutathione Depletion, Protein Adduct Formation, and Cytotoxicity Following Exposure to 4-Hydroxy-2-Nonenal (HNE) in Cells Expressing Human Multidrug Resistance Protein-1 (MRP1) Together with Human Glutathione S-Transferase-M1 (GSTM1)," Rudd, L. P., Kabler, S. L., Morrow, C. S., Townsend, A. J., Chem. Biol. Interact. (2011) 194.

"Increased Growth Inhibitory Effects on Human Cancer Cells and Anti-Inflammatory Potency of Shogaols from Zingiber Officinale Relative to Gingerols," Sang, S., Hong, J., Wu, H., Liu, J., Yang, C.S., Pan, M.H., Badmaev, V., Ho, C-T., Journal of Agricultural and Food Chemistry 57, No. 22 (2009).

(56) References Cited

OTHER PUBLICATIONS

"High-performance Liquid Chromatographic Analysis of 6-Gingerol, 8-Gingerol, 10-Gingerol, and 6-Shogaol in Ginger-containing Dietary Supplements, Spices, Teas, and Beverages," Schwertner, H. A.; Rios, D. C., J. Chromatogr., B: Anal. Technol. Biomed. Life Sci. (2007) 856.
"Quantitative Analysis of Ginger Components in Commercial Products Using Liquid Chromatography with Electrochemical Array Detection," Shao, Xi, Lv, L., Parks, T., Wu, H., Ho, C-T., Sang, S., Journal of Agricultural and Food Chemistry 58, No. 24 (2010).
"Synthesis of Analogues of Gingerol and Shogaol, The Active Pungent Principles From the Rhizomes of Zingiber Officinale and Evaluation of Their Anti-platelet Aggregation Effects," Shih, H. C.; Chern, C. Y.; Kuo, P. C.; Wu, Y. C.; Chan, Y. Y.; Liao, Y. R.; Teng, C. M.; Wu, T. S., Int. J. Mol. Sci. (2014) 15.
"Cancer Preventive Properties of Ginger: A Brief Review," Shukla, Y., & Singh, M., Food Chem, Toxicol. (2007) 45.
"Anti-Tumor Promoting Potential of Selected Spice Ingredients with Antioxidative and Anti-Inflammatory Activities: A Short Review," Surh, Y.J., Food Chem. Toxicol. (2002) 40.
"Chemoprotective Properties of Some Pungent Ingredients Present in Red Pepper and Ginger," Surh, Y.J., Lee, E., & Lee, J.M., Mutat Res, (1998) 402(1-2).
"6-Shogaol Inhibits Breast and Colon Cancer Cell Proliferation Through Activation of Peroxisomal Proliferator Activated Receptor Gamma (PPARgamma)," Tan, B. S., Kang, O., Mai, C. W., Tiong, K. H., Khoo, A. S., Pichika, M. R., Bradshaw, T. D., Leong, C. O., Cancer Lett. (2013) 336.
"Simultaneous Determination of 6-Gingerol, 8-Gingerol, 10-Gingerol and 6-Shogaol in Rat Plasma by Liquid Chromatography-Mass Spectrometry: Application to Pharmacokinetics," Wang, W., Li, C. Y., Wen, X. D., Li, P., Qi, L. W., J. Chromatogr. B: Anal. Technol. Biomed. Life Sci. (2009) 877.
"Induction of Lung Cancer Cell Apoptosis Through a p53 Pathway by [6]-Shogaol and its Cysteine-conjugated Metabolite M2," Warin, R. F., Chen, H., Soroka, D. N., Zhu, Y., Sang, S., J. Agric. Food Chem. (2014) 62.
"Anti-Invasion Effects of 6-Shogaol and 6-Gingerol, Two Active Components in Ginger, on Human Hepatocarcinorna Cells," Weng, C. J., Wu, C. F., Huang, H. W., Ho, C. T., & Yen, G. C., Molecular Nutrition & Food Research, (2010) 54(11).
"Chemopreventive Effects of Dietary Phytochemicals Against Cancer Invasion and Metastasis: Phenolic Acids, Monophenol, Polyphenol, and Their Derivatives," Weng, C-J., Yen, G-C., Cancer Treatment Reviews 38, No. 1 (2012).
"Molecular Mechanism Inhibiting Human Hepatocarcinoma Cell Invasion by 6-Shogaol and 6-Gingerol," Weng, C-J., Chou, C-P., Ho, C-T., Yen, G.C., Molecular Nutrition & Food Research 56, No. 8 (2012).
"6-Shogaol is More Effective Than 6-Gingerol and Curcumin in Inhibiting 12-O-tetradecanoylphorbol 13-acetate-induced Tumor Promotion in Mice," Wu, H., Hsieh, M-C., Lo, C-Y/. Liu, C.B., Sang, S., Ho, C-T., Pan, M-H., Molecular Nutrition & Food Research 54, No. 9 (2010).
"Structure and Synthesis of [n]-dehydroshogaols from Zingiber Officinale," Wu, T-S., Wu, Y-C., Wu, P-L., Chern., C-Y., Leu, Y-L., Chan, Y-Y., Phytochemistry 48, No. 5 (1998).
"Examination of the Pharmacokinetics of Active Ingredients of Ginger in Humans,"Yu, Y., Zick, S., Li, X., Zou, P., Wright, B., & Sun, D., The AAPS Journal, (2011) 13(3).
"Metabolites of Ginger Component [6]-Shogaol Remain Bioactive in Cancer Cells and Have Low Toxicity in Normal Cells: Chemical Synthesis and Biological Evaluation," Zhu, Y, Warin, R.F., Soroka, D.N., Chen, H., Sang, S., PloS one 8, No. 1 (2013).
"Quantitation of 6-, 8- and 10-Gingerols and 6-Shogaol in Human Plasma by High-performance Liquid Chromatography with Electrochemical Detection," Zick, S. M., Ruffin, M. T., Djuric, Z., Normolle, D., Brenner, D.E., Int. J. Biomed. Sci. (2010) 6.
"Pharmacokinetics of 6-Gingerol, 8-Gingerol, 10-Gingerol, and 6-Shogaol and Conjugate Metabolites in Healthy Human Subjects," Zick, S.M., Djuric. Z., Ruffin, M.T., Litzinger, A.J., Normolle, D.P., Alrawi, S., Feng, M.R., Brenner, D.E., Cancer Epidemiology Biomarkers & Prevention 17, No. 8 (2008).

\* cited by examiner (a)  (b)

(a)

(b)

(c)

(d)

(a)

(b)

(c)

(a)

(b)

(a)

(b)

GINGER METABOLITES AND USES THEREOF

RELATED APPLICATIONS

This application is a divisional of, and claims the benefit of U.S. patent application Ser. No. 14/134,504 having a filing date of Dec. 19, 2013, which claims the benefit of U.S. Provisional Patent Applications 61/739,169, filed Dec. 19, 2012 and 61/790,291, filed Mar. 15, 2013, the disclosure of each of which is incorporated herein by reference in its entirety.

STATEMENT OF FEDERAL SUPPORT

This invention was made with Government support under CA138277 awarded by the National Institutes of Health National Cancer Institute and Office of Dietary Supplements. The United States Government has certain rights in this invention.

FIELD

The present inventions relate generally to metabolites of shogaol components of ginger, including compounds related to 6-shogaol, 8-shogaol and 10-shogaol. Such compounds generally are preferentially toxic to cancer cells with decreased killing of non-cancer cells. The present inventions also relate generally to pharmaceutical or nutraceutical compositions comprising such compounds.

BACKGROUND

Ginger (*Zingiber officinale* Rosc.), a member of the Zingiberaceae family, has been cultivated for thousands of years as a spice and for medicinal purposes. It is believed that the major pharmacologically active components of ginger are gingerols and shogaols. Shogaols, α,β-unsaturated ketones which are the dehydrated products of gingerols, are the predominant pungent constituents in dried ginger.

SUMMARY

The present application is generally directed to shogaol-related compounds. For example, the present application discloses metabolites of ginger components, such as metabolites of [6]-shogaol, [8]-shogaol and [10]-shogaol, including but not limited to 5-cysteinyl-[6]-shogaol (herein referred to as "M2"); 5-cysteinyl-[8]-shogaol (herein referred to as "M2'"); and 5-cysteinyl-[10]-shogaol (herein referred to as "M2''"). Such derivatives are used as pharmaceuticals for the treatment and prevention of diseases such as cancer, or can be used as a dietary supplement, nutraceutical or adjunct therapy. Generally, the shogaol derivatives disclosed herein are used (a) to help control symptoms of disease, such as cancer; (b) to alleviate unwanted side effects of an underlying disease or a therapy for such an underlying disease; (c) to prevent future disease; or (d) to contribute to treatment of a present disease.

In one aspect, the present application discloses a compound of Formula I:

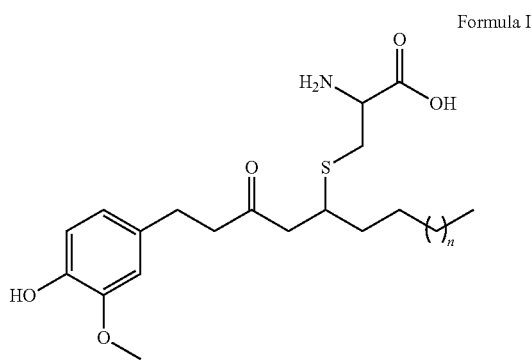

Formula I wherein n is 2, 4 or 6 or a pharmaceutically acceptable salt or hydrate thereof.

In another aspect, the present application discloses compound of Formula II:

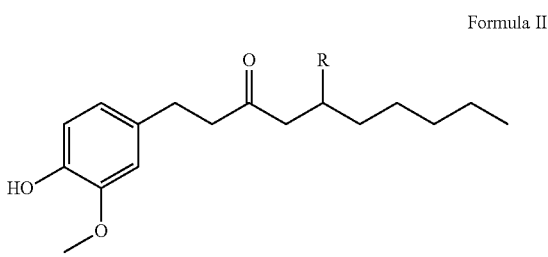

Formula II or a pharmaceutically acceptable salt or hydrate thereof wherein R is

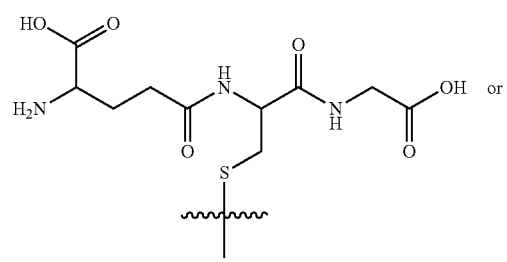 or

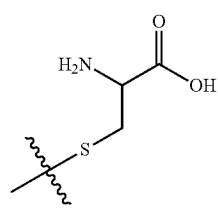

and any diastereomers thereof.

In one variation, the present application discloses a compound of Formula III:

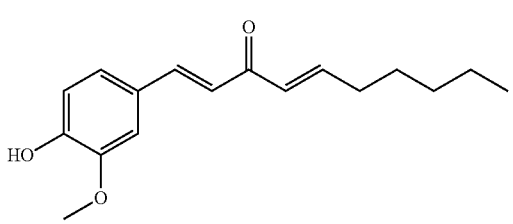

Formula III or a pharmaceutically acceptable salt or hydrate thereof.

A first aspect of the present invention is a composition comprising, consisting essentially of or consisting of a compound of Formula I, II, or III.

A second aspect of the present invention is a pharmaceutical composition comprising, consisting essentially of or consisting of a compound of Formula I, II, or III and a pharmaceutically acceptable carrier.

A third aspect of the present invention is a nutraceutical composition comprising, consisting essentially of or consisting of a compound of Formula I, II, or III and an acceptable carrier.

A fourth aspect of the present invention is a dietary supplement comprising, consisting essentially of or consisting of a compound of Formula I, II, or III and an acceptable carrier.

A fifth aspect of the present invention is a method of producing a compound of Formula I, II, or III.

A sixth aspect of the present invention is a method of preventing and/or treating a disorder in a subject in need thereof, comprising, consisting essentially of or consisting of administering to said subject a therapeutically effective amount of a composition comprising, consisting essentially of or consisting of a compound of Formula I, II, or III.

A seventh aspect of the present invention is a method of preventing and/or treating a disorder in a subject in need thereof, comprising, consisting essentially of or consisting of administering to said subject a pharmaceutical composition comprising, consisting essentially of or consisting of a compound of Formula I, II, or III and a pharmaceutically acceptable carrier.

An eighth aspect of the present invention is a method of preventing, treating, and/or contributing to the treatment of a disorder in a subject in need thereof, comprising, consisting essentially of or consisting of administering to said subject a composition comprising, consisting essentially of or consisting of a compound of Formula I, II, or III and an acceptable carrier. The composition can be a nutraceutical composition or a dietary supplement.

A ninth aspect of the present invention is a kit for preventing, treating and/or contributing to the treatment of a disorder in a subject comprising, consisting essentially of or consisting of a compound, a pharmaceutical composition, a nutraceutical composition or a dietary supplement of the present invention and instructions for using the compound, the pharmaceutical composition or the nutraceutical composition.

These and other objects and aspects of the present inventions will become apparent to those skilled in the art after a reading of the following description of the disclosure when considered with the drawings.

It will be understood that the drawings are for the purpose of describing embodiments of the present application and are not intended to limit the inventions thereto.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
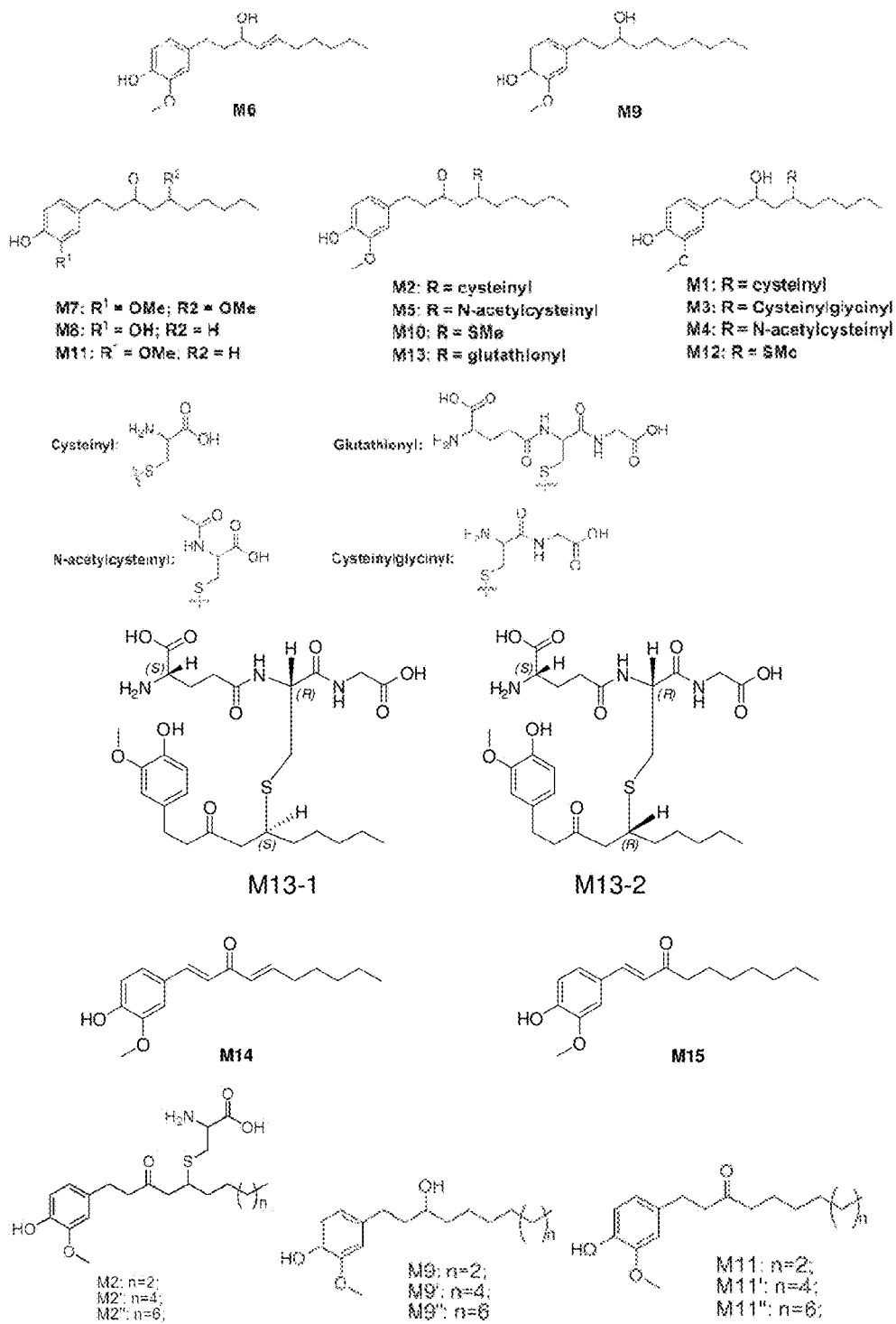
FIG. 1 shows the structure of [6]-shogaol, [8]-shogaol, [10]-shogaol, and some metabolites of those compounds.

The foregoing and other aspects of the present invention will now be described in more detail with respect to compositions and methodologies provided herein.

This description is not intended to be a detailed catalogue of all the ways in which the present invention may be implemented or of all the features that may be added to the present invention. For example, features illustrated with respect to one embodiment may be incorporated into other embodiments, and features illustrated with respect to a particular embodiment may be deleted from that embodiment. Thus, one or more of the method steps included in a particular method described herein may, in other embodiments, be omitted and/or performed independently. In addition, numerous variations and additions to the embodiments suggested herein, which do not depart from the instant invention, will be apparent to those skilled in the art in light of the instant disclosure. Hence, the following description is intended to illustrate some particular embodiments of the invention, and not to exhaustively specify all permutations, combinations and variations thereof. It should therefore be appreciated that the present invention is not limited to the particular embodiments set forth herein. Rather, these particular embodiments are provided so that this disclosure will convey the full scope of the invention to those skilled in the art.

The terminology used herein is for the purpose of describing particular embodiments of the present invention only and is not intended to limit the present invention.

Although the following terms are believed to be well understood by one of skill in the art, the following definitions are set forth to facilitate understanding of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

As used herein, the terms "a" or "an" or "the" may refer to one or more than one. For example, "a" pharmaceutically acceptable excipient can mean one pharmaceutically acceptable excipient or a plurality of pharmaceutically acceptable excipients.

As used herein, the term "about," when used in reference to a measurable value such as an amount of mass, dose, time, temperature, and the like, is meant to encompass variations of +/−20% of the specified amount.

All ranges set forth, unless otherwise stated, include the stated endpoints and all increments between.

As used herein, the term "and/or" refers to and encompasses any and all possible combinations of one or more of the associated listed items, as well as the lack of combinations when interpreted in the alternative ("or").

As used herein, the term "cancer" refers to any benign or malignant abnormal growth of cells. Examples include, without limitation, breast cancer, prostate cancer, lymphoma, skin cancer, pancreatic cancer, colon cancer, colorectal cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In some embodiments, the cancer is selected from the group of tumor-forming cancers. In some embodiments, the cancer is colorectal cancer or lung cancer.

In some embodiments, the cancer is a cancer formed at a different site of a body as a result of migration of a cell from a cancer (i.e. metastasis) including but not limited to any cancer mentioned herein.

In other embodiments, a compound or composition of the present application is used for the prevention of one cancer or metastasis of one cancer and concurrently for the treatment of another cancer mentioned hereinabove.

The present application also involves the delivery of therapeutic compounds to subjects exhibiting pre-cancerous symptoms to prevent the onset of cancer. Cells of this category include but are not limited to polyps and other precancerous lesions, premalignancies, preneoplastic or other aberrant phenotype indicating probable progression to a cancerous state.

As used herein, the phrase "nutraceutical composition" or variants thereof refers to compositions containing a compound disclosed herein and further containing a food or a liquid, part of a food or a liquid, or is an addition to a food or a liquid, wherein such composition provides medical or health benefits, including the prevention and treatment of disease either alone or in combination with a primary therapy, or the trigger of a beneficial physiological response.

A nutraceutical composition as disclosed herein provides a nutritional source, thus, a nutraceutical composition can be a food product, foodstuff, functional food, or a supplement composition for a food product or a foodstuff. As used herein, the term food product refers to any food which provides a nutritional source and is suitable for oral consumption by humans or animals. The food product may be a prepared and packaged food or an animal feed. As used herein, the term foodstuff refers to a nutritional source for human or animal consumption. Functional foods are foods consumed as part of a diet which are demonstrated to have physiological benefits beyond basic nutritional functions. Food products, foodstuffs, or functional foods include but are not limited to beverages, such as non-alcoholic and alcoholic drinks as well as liquid preparations to be added to drinking water and liquid food, and solid or semi-solid foods. Non-alcoholic drinks include but are not limited to nutritional shakes, soft drinks; sport drinks; fruit juices; and milk and other dairy drinks such as yogurt drinks and protein shakes. Examples of solid or semi-solid food include, but are not limited to, baked goods; puddings; dairy products; confections; snack foods; or frozen confections or novelties; prepared frozen meals; candy; liquid food such as soups; spreads; sauces; salad dressings; prepared meat products; cheese; yogurt and any other fat or oil containing foods; and food ingredients.

As used herein, the term "consists essentially of" (and grammatical variants thereof), as applied to the compositions and methods of the present invention, means that the compositions/methods may contain additional components so long as the additional components do not materially alter the composition/method. The term "materially alter," as applied to a composition/method of the present invention, refers to an increase or decrease in the effectiveness of the composition/method of at least about 20% or more. For example, a component added to a composition of the present invention would "materially alter" the composition if it increases or decreases the composition's ability to inhibit tumor growth by at least 20%.

As used herein, the term "emulsion" refers to a suspension or dispersion of one liquid within a second immiscible liquid. In some embodiments, the emulsion is an oil-in-water emulsion or a water-in-oil emulsion. In some embodiments, "emulsion" may refer to a material that is a solid or semi-solid at room temperature and is a liquid at body temperature (about 37° C.).

As used herein, "pharmaceutically acceptable" means that the material is suitable for administration to a subject and will allow desired treatment to be carried out without giving rise to unduly deleterious adverse effects. The severity of the disease and the necessity of the treatment are generally taken into account when determining whether any particular side effect is unduly deleterious.

As used herein, the terms "purified," or "isolated" refer to a compound after isolated from a synthetic process (e.g., from a reaction mixture), or from a natural source or some combination thereof. Thus, the term "purified," or its alternatives, including "in purified form" or "in isolated and purified form" refers to the physical state of a compound after being obtained from a purification process or processes as described herein or well known to the skilled artisan (e.g., chromatography, recrystallization and the like), in sufficient purity to be characterizable by standard analytical techniques described herein or well known to the skilled artisan. The purification techniques disclosed herein result in isolated and purified forms of the subject metabolites. Such isolation and purification techniques would be expected to result in product purities of 95 wt % or better, including enantiomers of the same molecule.

As used herein, the terms "prevent," "preventing," and "prevention" (and grammatical variants thereof) refer to avoidance, prevention and/or delay of the onset of a disease, disorder and/or a clinical symptom(s) in a subject and/or a reduction in the severity of the onset of the disease, disorder and/or clinical symptom(s) relative to what would occur in the absence of the compositions and/or methods of the present invention. In some embodiments, prevention is complete, resulting in the total absence of the disease, disorder and/or clinical symptom(s). In some embodiments, prevention is partial, resulting in reduced severity and/or delayed onset of the disease, disorder and/or clinical symptom(s).

As used herein, the term "prevention effective amount" (and grammatical variants thereof) refers an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

As used herein, the term "subject" (and grammatical variants thereof) refers to mammals, avians, reptiles, amphibians, or fish. Mammalian subjects may include, but are not limited to, humans, non-human primates (e.g., monkeys, chimpanzees, baboons, etc.), dogs, cats, mice, hamsters, rats, horses, cows, pigs, rabbits, sheep and goats. Avian subjects may include, but are not limited to, chickens, turkeys, ducks, geese, quail and pheasant, and birds kept as pets (e.g., parakeets, parrots, macaws, cockatoos, and the like). In particular embodiments, the subject is from an endangered species. In particular embodiments, the subject is a laboratory animal. Human subjects may include neonates, infants, juveniles, adults, and geriatric subjects. In particular embodiments, the subject is male. In particular embodiments, the subject is female.

As used herein, the term "therapeutically effective" refers to provision of some improvement or benefit to the subject. Alternatively stated, a "therapeutically effective amount" is an amount that will provide some alleviation, mitigation, or decrease in at least one clinical symptom in the subject (e.g., in the case of cancer, reduced tumor size, decreased incidence of metastasis, etc.). Those skilled in the art will appreciate that the therapeutic effects need not be complete or curative, as long as some benefit is provided to the subject.

As used herein, the terms "therapeutically effective amount" and "therapeutically acceptable amount" (and grammatical variants thereof) refer to an amount that will elicit a therapeutically useful response in a subject. The therapeutically useful response may provide some alleviation, mitigation, or decrease in at least one clinical symptom in the subject. The terms also include an amount that will prevent or delay at least one clinical symptom in the subject and/or reduce and/or delay the severity of the onset of a clinical symptom in a subject relative to what would occur in the absence of the methods of the invention. Those skilled in the art will appreciate that the therapeutically useful response need not be complete or curative or prevent permanently, as long as some benefit is provided to the subject.

As used herein, the terms "treatment," "treat," and "treating" refer to reversing, alleviating, delaying the onset of, inhibiting the progress of or preventing a disease or disorder. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

As used herein, the term "treatment effective amount" (and grammatical variants thereof) refers to an amount that is sufficient to provide some improvement or benefit to the subject. Alternatively stated, a "treatment effective amount" is an amount that will provide some alleviation, mitigation, decrease, or stabilization in at least one clinical symptom in the subject. Those skilled in the art will appreciate that the therapeutic effects need not be complete or curative, as long as some benefit is provided to the subject.

In one aspect of the present invention, the compositions disclosed herein are "nutraceutical compositions" help control symptoms of disease; alleviate unwanted side effects of an underlying disease or a therapy for such an underlying disease; prevent future disease, or contribute to treatment of a disease. In some embodiments, the nutraceutical composition is administered at the same time as the pharmaceutical treatment; in other embodiments, nutraceutical composition is administered before or after pharmaceutical treatment. When the nutraceutical composition is administered before or after pharmaceutical treatment, such administration occurs hours, days, or months before pharmaceutical treatment. In some embodiments, the nutraceutical composition is administered after one or more symptoms have developed. In other embodiments, the nutraceutical composition is administered in the absence of symptoms. For example, the nutraceutical composition is administered to a susceptible individual prior to the onset of symptoms (e.g., in light of a history of symptoms and/or in light of genetic or other susceptibility factors). Administration of the nutraceutical composition may also be continued after symptoms have resolved, for example, to prevent or delay their recurrence.

The present invention provides compositions useful for the prevention and/or treatment of disease.

In one aspect, the present application discloses a compound of Formula I:

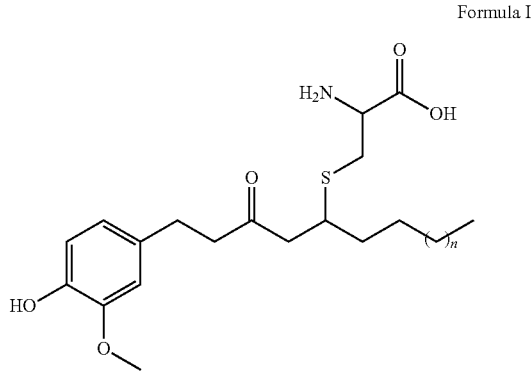

Formula I wherein n is selected from the group of 2, 4, 6 and combinations thereof. In one variation, the compound is a pharmaceutically acceptable salt or hydrate thereof. In one variation, the compound is in an isolated or purified form. In one embodiment of the compound of Formula I, n is 2; in another embodiment, n is 4 and in yet another embodiment, n is 6. As would be understood by those in the art, "2" indicates the existence of two "n" components, "4" indicates the existence of four "n" components, and "6" indicates the existence of six "n" components.

In another aspect, the present application discloses compound of Formula II:

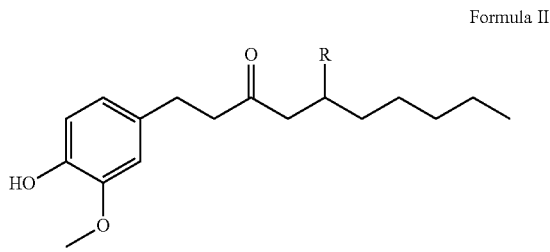

Formula II or a pharmaceutically acceptable salt or hydrate thereof, wherein R is

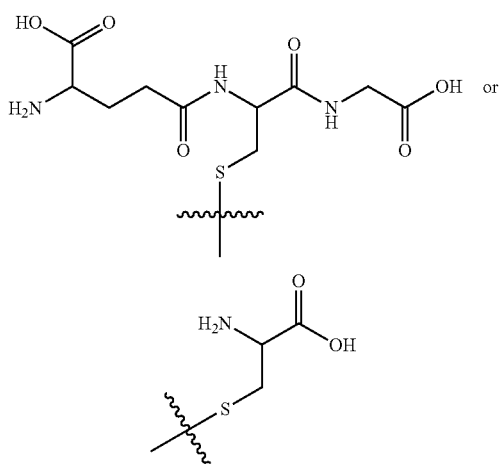

and any diastereomers thereof. In one variation, the compound is in an isolated or purified form. In one embodiment, the compound is:

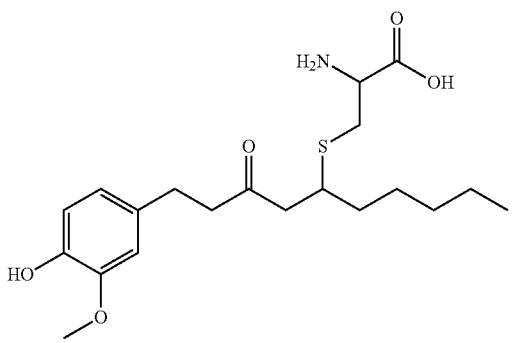 [SMILES: CCCCCC(CC(=O)CCc1ccc(O)c(OC)c1)SCC(N)C(=O)O]

or a pharmaceutically acceptable salt or hydrate thereof in an isolated or purified form. In another embodiment, the compound is:

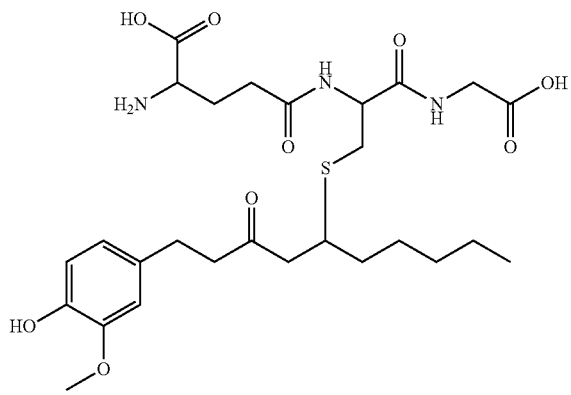 [SMILES: CCCCCC(CC(=O)CCc1ccc(O)c(OC)c1)SCC(NC(=O)CCC(N)C(=O)O)C(=O)NCC(=O)O]

or a pharmaceutically acceptable salt or hydrate thereof in an isolated or purified form.

In another aspect, the present application discloses a compound of Formula III:

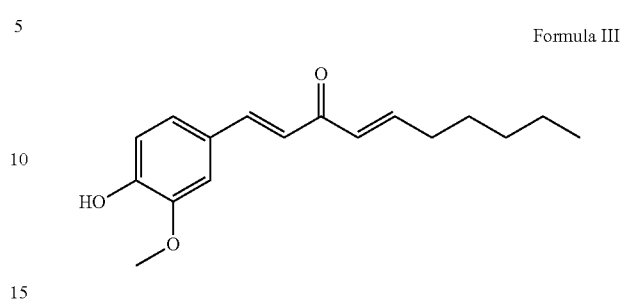

Formula III or a pharmaceutically acceptable salt or hydrate thereof in an isolated or purified form.

In another aspect, the present application discloses a compound having the formula:

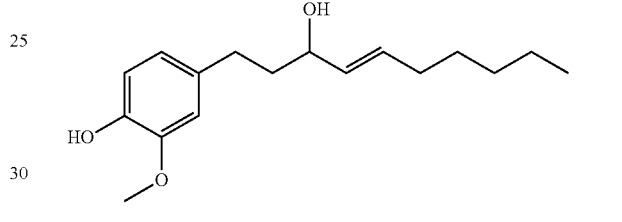

M6

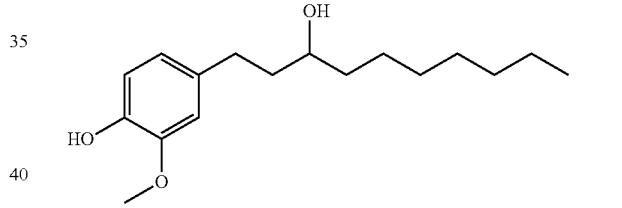

M9

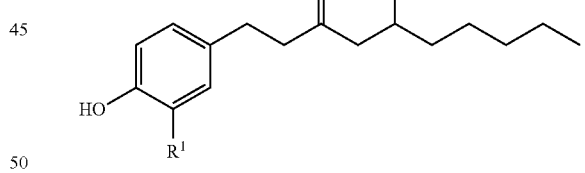

M7: $R^1$ = OMe; $R^2$ = OMe
M8: $R^1$ = OH; $R^2$ = H
M11: $R^1$ = OMe; $R^2$ = H

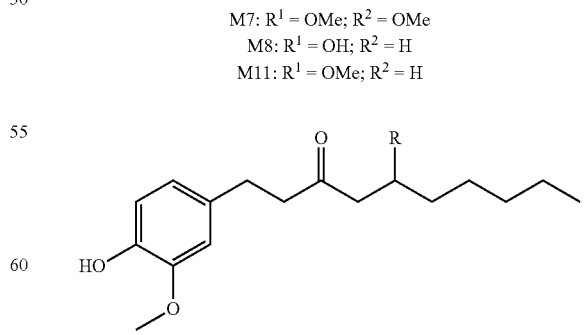

M2: R = cysteinyl
M5: R = N-acetylcysteinyl
M10: R = SMe
M13: R = glutathionyl

-continued

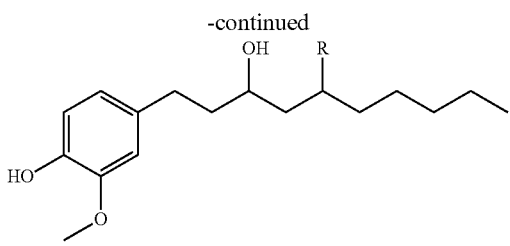

M1: R = cysteinyl
M3: R = Cysteinylglycinyl
M4: R = N-acetylcysteinyl
M12: R = SMe Cysteinyl:

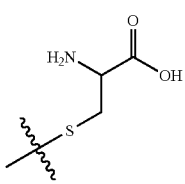

Glutathionyl:

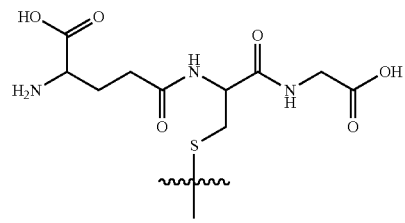

N-acetylcysteinyl:

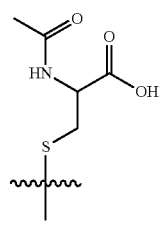

Cysteinylglycinyl:

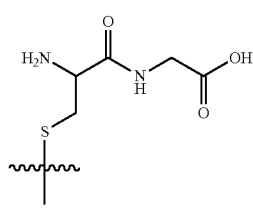

or a pharmaceutically acceptable salt or hydrate thereof in an isolated or purified form.

In another aspect, the present application discloses a compound having the formula:

M14

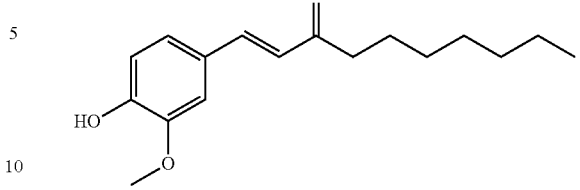

-continued

M15

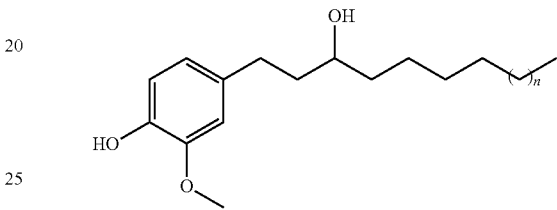

or a pharmaceutically acceptable salt or hydrate thereof in an isolated or purified form.

In yet another aspect, the present application discloses a compound having the formula:

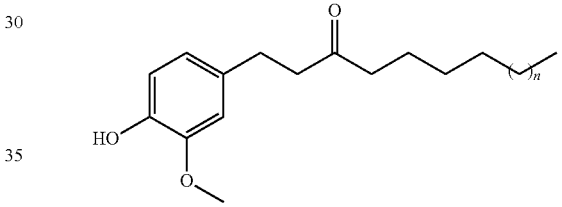

M9: n = 2;
M9': n = 4;
M9": n = 6;

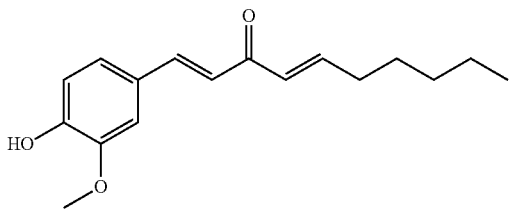

M11: n = 2;
M11': n = 4;
M11": n = 6;

or a pharmaceutically acceptable salt or hydrate thereof, in an isolated or purified form.

Compounds of the present invention may exist as stereoisomers, such as double-bond isomers (i.e., geometric isomers), enantiomers or diastereomers. The chemical structures depicted herein are intended to encompass all possible enantiomers and stereoisomers of the illustrated compounds, including the stereoisomerically pure form (e.g., geometrically pure, enantiomerically pure or diastereomerically pure) and enantiomeric and stereoisomeric mixtures. As will be understood by those skilled in the art, enantiomeric and stereoisomeric mixtures can be resolved into their component enantiomers or stereoisomers using well known separation techniques and/or chiral synthesis techniques.

Compounds of the present invention may exist in several tautomeric forms, including the enol form, the keto form and mixtures thereof. The chemical structures depicted herein are intended to encompass all possible tautomeric forms of the illustrated compounds.

Compounds of the present invention may be stable in environments having a pH less than about 0.1 to 14.0, or any sub-range within that range.

Compounds of the present invention may exist as isotopically labeled compounds, wherein one or more atoms have an atomic mass different from the atomic mass conventionally found in nature. Examples of isotopes that can be incorporated into the compounds of the present invention include, but are not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$. The chemical structures depicted herein are intended to encompass all possible isotopically labeled versions of the compounds of the present invention. Isotopically labeled compounds of the present invention may be used in any suitable method known in the art, including, but not limited to, methods of preventing, diagnosing, monitoring and/or treating a disorder.

Compounds of the present invention may comprise any suitable pharmaceutically acceptable salt, including, but not limited to, acid addition salts and base addition salts. Examples of suitable salts can be found for example in Stahl and Wermuth, *Handbook of Pharmaceutical Salts Properties, Selection, and Use*, Wiley-VCH, Weinheim, Germany (2002); and Berge et al., "Pharmaceutical Salts," J. of Pharmaceutical Science, 1977; 66:1-19. In some embodiments, the pharmaceutically acceptable salts of the compounds is a disalt. In some embodiments, the pharmaceutically acceptable salt is an L-tartrate salt.

Pharmaceutically acceptable acid addition salts include but are not limited to non-toxic salts derived from inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include the acetate, aspartate, benzoate, besylate (benzenesulfonate), bicarbonate/carbonate, bisulfate, caprylate, camsylate (camphor sulfonate), chlorobenzoate, citrate, edisylate (1,2-ethane disulfonate), dihydrogenphosphate, dinitrobenzoate, esylate (ethane sulfonate), fumarate, gluceptate, gluconate, glucuronate, hibenzate, hydrochloride/chloride, hydrobromide/bromide, hydroiodide/iodide, isobutyrate, monohydrogen phosphate, isethionate, D-lactate, L-lactate, malate, maleate, malonate, mandelate, mesylate (methanesulfonate), metaphosphate, methylbenzoate, methylsulfate, 2-napsylate (2-naphthalene sulfonate), nicotinate, nitrate, orotate, oxalate, palmoate, phenylacetate, phosphate, phthalate, propionate, pyrophosphate, pyrosulfate, saccharate, sebacate, stearate, suberate, succinate sulfate, sulfite, D-tartrate, L-tartrate, tosylate (toluene sulfonate), and xinafoate salts, and the like of compounds described herein. Also contemplated are the salts of amino acids such as arginate, gluconate, galacturonate, and the like.

Acid addition salts of the compounds disclosed herein may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present application.

Pharmaceutically acceptable base addition salts may be formed with metals or amines, such as alkali and alkaline earth metal hydroxides, or of organic amines. Examples of metals used as cations are aluminum, calcium, magnesium, potassium, sodium, and the like. Examples of suitable amines include arginine, choline, chloroprocaine, N,N'-dibenzylethylenediamine, diethylamine, diethanolamine, diolamine, ethylenediamine (ethane-1,2-diamine), glycine, lysine, meglumine, N-methylglucamine, olamine, procaine (benzathine), and tromethamine.

The base addition salts of the compounds disclosed herein may be prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present application.

In some embodiments, the present invention provides a composition comprising, consisting essentially of or consisting of one or more compounds of the present invention.

In some embodiments, the present invention provides a pharmaceutical composition comprising, consisting essentially of or consisting of 1) a pharmaceutically acceptable carrier and 2) a unit dose of an active ingredient wherein said active ingredient is a compound of Formula I:

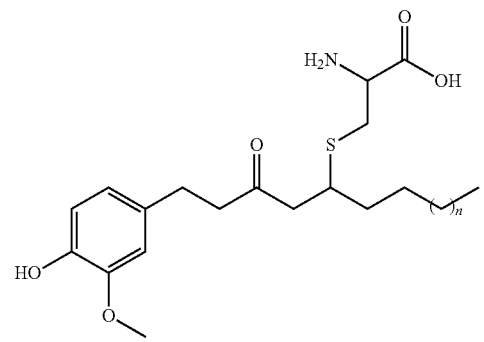

Formula I wherein n is selected from the group consisting of 2, 4, 6 and combinations thereof. In one variation, the compound is a pharmaceutically acceptable salt or hydrate thereof. In another variation, the compound is in an isolated or purified form.

In one embodiment of the composition comprises a compound of Formula I wherein n is 2; in another embodiment, n is 4 and in yet another embodiment, n is 6. In another embodiment, the composition comprises one or more of the compounds of Formula I, such as a composition comprising a compound where n is 2 and a compound where n is 4, or a compound where n is 2 and a compound where n is 6 or a compound where n is 4 and a compound where n is 6. Alternately, such a composition comprises a compound where n is 2 and a compound where n is 4 and a compound where n is 6. In one variation, the compound is in an isolated or purified form.

In another aspect, the present invention provides a pharmaceutical composition comprising, consisting essentially of or consisting of 1) a pharmaceutically acceptable carrier and 2) a unit dose of an active ingredient wherein said active ingredient is a compound of Formula II:

Formula II

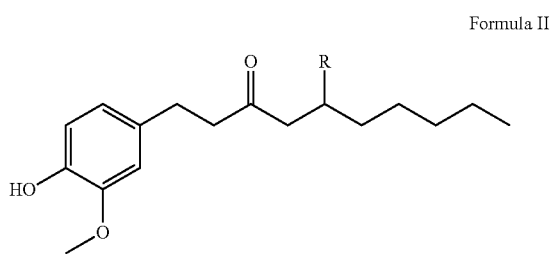

or a pharmaceutically acceptable salt or hydrate thereof wherein R is

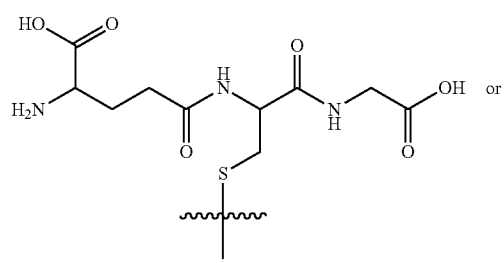

and any diastereomers thereof. In one variation, the compound is in an isolated or purified form.

In one variation, the pharmaceutical composition comprises:

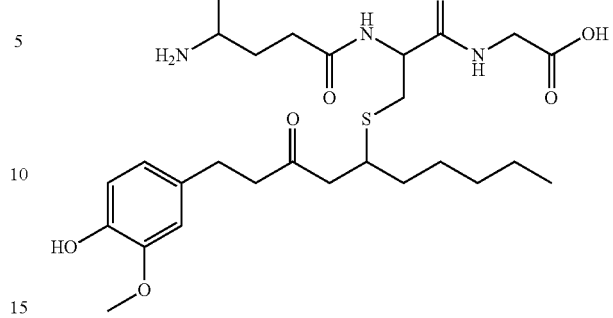

or a pharmaceutically acceptable salt or hydrate thereof. In another variation, the pharmaceutical composition comprises:

or a pharmaceutically acceptable salt or hydrate thereof. In one variation, the compound is in an isolated or purified form.

In another aspect, the present invention provides a pharmaceutical composition comprising, consisting essentially of or consisting of 1) a pharmaceutically acceptable carrier and 2) a compound of Formula III:

Formula III

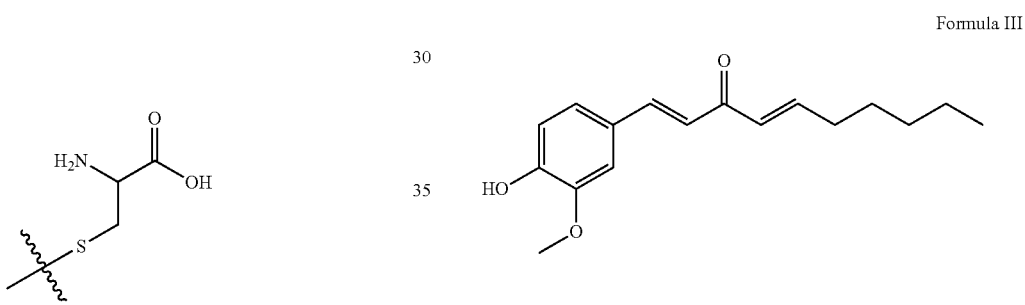

or a pharmaceutically acceptable salt or hydrate thereof. In one variation, the compound is in an isolated or purified form.

In some embodiments, the present invention provides a nutraceutical composition comprising, consisting essentially of or consisting of 1) a food grade carrier and 2) an active ingredient wherein said active ingredient is a compound of Formula I Formula I wherein n is 2, 4, 6, and combinations thereof. In one variation, the compound is a pharmaceutically acceptable salt or hydrate thereof. In one variation, the compound is in an isolated or purified form.

In one embodiment of the composition comprises a compound of Formula I wherein n is 2; in another embodiment, n is 4 and in yet another embodiment, n is 6. In another embodiment, the composition comprises one or more of the compounds of Formula I, such a composition comprises a compound where n is 2 and a compound where n is 4, or the composition comprises a compound where n is 2 and a compound where n is 6, or the composition comprises a compound where n is 4 and a compound where n is 6. Alternately, such a composition comprises a compound where n is 2, a compound where n is 4 and a compound where n is 6. In another variation, the composition comprises a compound where n consists essentially of 2 and 4, or 2 and 6, or 4 and 6, or n consists essentially of 2, 4 and 6.

In another aspect, the present invention provides a nutraceutical composition comprising, consisting essentially of or consisting of 1) a food grade carrier and 2) a compound of Formula II:

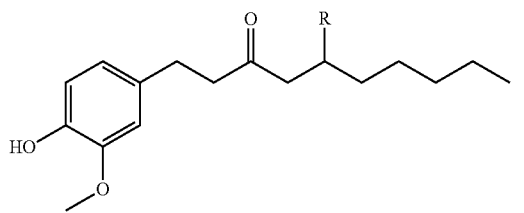

Formula II or a pharmaceutically acceptable salt or hydrate thereof wherein R is

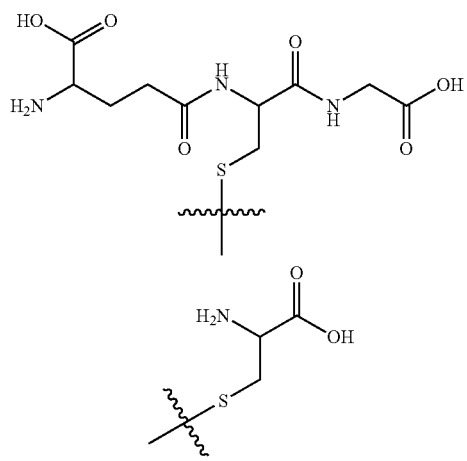

and any diastereomers thereof. In one variation, the compound is in an isolated or purified form.

In one variation, the nutraceutical composition comprises:

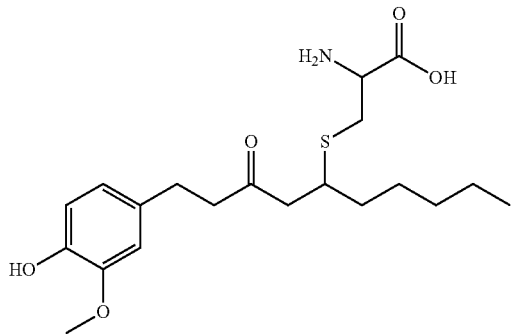 [SMILES: CCCCCC(CC(=O)CCc1ccc(O)c(OC)c1)SCC(N)C(=O)O]

or a pharmaceutically acceptable salt or hydrate thereof.

In another variation, the nutraceutical composition comprises:

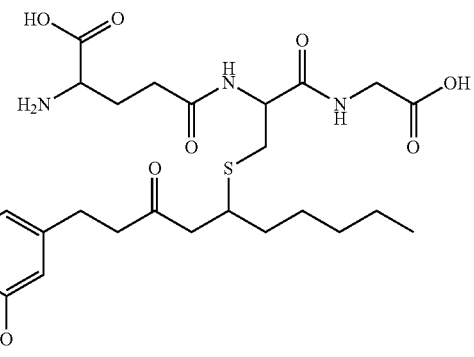

or a pharmaceutically acceptable salt or hydrate thereof. In one variation, the compound is in an isolated or purified form.

In another aspect, the present invention provides a nutraceutical composition comprising, consisting essentially of or consisting of 1) a food grade carrier and 2) a compound of Formula III:

Formula III

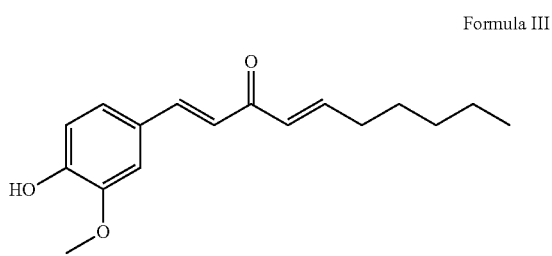 [SMILES: CCCCC/C=C/C(=O)/C=C/c1ccc(O)c(OC)c1]

or a pharmaceutically acceptable salt or hydrate thereof. In one variation, the compound is in an isolated or purified form.

In another aspect, the present invention provides a composition comprising, consisting essentially of or consisting of 1) an acceptable carrier and 2) one or more compounds having the formula:

M6

M9

M7: R¹ = OMe; R² = OMe
M8: R¹ = OH; R² = H
M11: R¹ = OMe; R² = H

M2: R = cysteinyl
M5: R = N-acetylcysteinyl
M10: R = SMe
M13: R = glutathionyl

M1: R = cysteinyl
M3 = R = Cysteinylglycinyl
M4: R = N-acetylcysteinyl
M12: R = SMe Cysteinyl:

Glutathionyl:

N-acetylcysteinyl:

Cysteinylglycinyl:

or a pharmaceutically acceptable salt or hydrate thereof. In one variation, the compound is in an isolated or purified form.

In another aspect, the present invention provides a composition comprising, consisting essentially of or consisting of 1) an acceptable carrier and 2) one or more compounds having the formula:

M14

M15 or a pharmaceutically acceptable salt or hydrate thereof. In one variation, the compound is in an isolated or purified form.

In yet another aspect, the present invention provides a composition comprising, consisting essentially of or consisting of 1) an acceptable carrier and 2) one or more compounds having the formula:

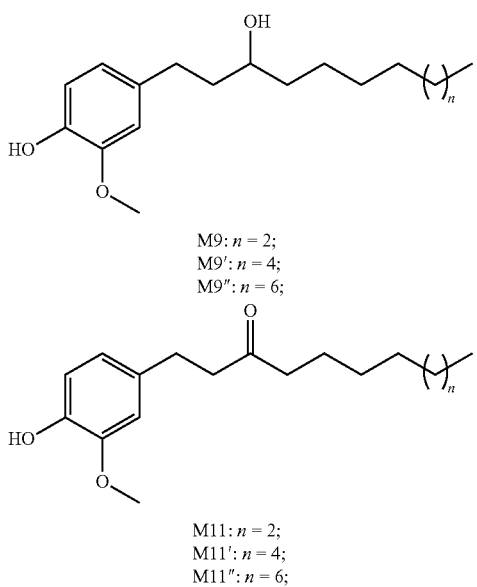

M9: n = 2;
M9': n = 4;
M9": n = 6;

M11: n = 2;
M11': n = 4;
M11": n = 6;

or a pharmaceutically acceptable salt or hydrate thereof. In one embodiment, the composition comprises one or more of M9, M9' and M9" or a pharmaceutically acceptable salt or hydrate thereof. In another embodiment, the composition comprises one or more of M11, M11' and M11" or a pharmaceutically acceptable salt or hydrate thereof. In one variation of any disclosed aspect or embodiment, the composition does not comprise M2, M9 or M11. In another variation, the composition comprises M2, M2', M2", M9, M9', M9", M11, M11' and M11" or a pharmaceutically acceptable salt. In yet another variation, the composition comprises M2', M2", M9', M9", M11' and M11". In one variation, the compound is in an isolated or purified form.

Formulations

Pharmaceutical compositions of the present invention may comprise any suitable pharmaceutical carrier moiety, including, but not limited to, phosphate buffered saline and isotonic saline solution. Other examples of pharmaceutically acceptable carriers may be found, for example, in ANSEL'S PHARMACEUTICAL DOSAGE FORMS AND DRUG DELIVERY SYSTEMS (9th Ed., Lippincott Williams and Wilkins (2010)), PHARMACEUTICAL SCIENCES (18th Ed., Mack Publishing Co. (1990) or REMINGTON: THE SCIENCE AND PRACTICE OF PHARMACY (21st Ed., Lippincott Williams & Wilkins (2005)).

Pharmaceutical compositions of the present invention may comprise any suitable diluent or excipient, including, but not limited to, those set forth in ANSEL'S PHARMACEUTICAL DOSAGE FORMS AND DRUG DELIVERY SYSTEMS (9th Ed., Lippincott Williams and Wilkins (2010)), HANDBOOK OF PHARMACEUTICAL EXCIPIENTS (6th Ed., American Pharmaceutical Association (2009)) and REMINGTON: THE SCIENCE AND PRACTICE OF PHARMACY (21st Ed., Lippincott Williams & Wilkins (2005)). In some embodiments, the composition comprises one or more pharmaceutically acceptable diluents and/or one or more pharmaceutically acceptable excipients.

Pharmaceutical compositions of the present invention may comprise any suitable auxiliary substance, including, but not limited to, pH adjusting and/or buffering agents, tonicity adjusting and/or buffering agents and lipid-protective agents that protect lipids against free-radical and lipid-peroxidative damages (e.g., alpha-tocopherol and water-soluble iron-specific chelators, such as ferrioxamine).

Pharmaceutical compositions containing the active ingredient may be in any form suitable for the intended method of administration and may be prepared according to any suitable method. Compositions in the form of tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil Aqueous suspensions of the application contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the application suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the application may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the application may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The compositions can be administered intravenously or by catheter-based techniques, or a combination thereof, with or without associated delivery devices (i.e. pumps). For example, treatment can be administered intravenously, in or associated with cardioplegia solutions, via local delivery procedures including direct injection into grafts or native arteries, and via perfusion-assisted techniques. The compositions of the present application can be infused intravenously, while other therapeutically active agents are delivered to the target organ selectively, or both therapies can be delivered by either intravenous or intravascular selective administration.

As noted above, formulations of the present application suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

The compositions described herein can be immediate-release formulations. A variety of known methods and materials may be used to bring about the immediate release. For instance, placement of the agent along an exterior of a tablet (e.g., coating the exterior or formulating the outer layer with the agent) and/or combined with forming a tablet by compressing the powder using low compaction can produce immediate-release of the agent from the composition. The composition can also be in a controlled-release form. The compositions can also be in a sustained release form.

The compositions therefore can comprise one or more carriers that protect the agents against rapid elimination from the body, such as time-release formulations or coatings. Such carriers include controlled-release formulations, including, for example, microencapsulated delivery systems. Compounds of the present application, a pharmaceutically acceptable salt thereof, can be included in the pharmaceutically acceptable carrier in amounts sufficient to treat an individual. The controlled-release form can be in an amount that is effective to protect the agent from rapid elimination from the body, or to provide a sustained release or dosage, such as between about 1 μg/kg/min to about 500 μg/kg/min, or any sub-range within. In other embodiments, the unit dose is from about 1 to about 500 mg/kg, or any sub-range within, of compound of the present application, such as a compound of the present application, or pharmaceutically acceptable salt thereof.

In certain embodiments the compositions are in oral dosage form and comprise a matrix that includes a controlled-release material. In certain embodiments, the matrix is compressible into a tablet and can be optionally over-coated with a coating that can control the release of the compound of the present application or pharmaceutically acceptable salt thereof, from the composition. In this embodiment, the compound or pharmaceutically acceptable salt thereof, is maintained within a therapeutic range over an extended period of time. In certain alternate embodiments, the matrix is encapsulated.

Tablets or capsules containing a composition of the present application can be coated or otherwise compounded to provide a dosage form affording the advantage of prolonged action. For example, the tablet or capsule can contain an inner dosage and an outer dosage component, the latter being in the form of an envelope over the former. The two components can be separated by an enteric layer that serves to resist disintegration in the stomach and permit the inner component to pass intact into the duodenum or to be delayed in release. For controlled extended release, the capsule can also have micro drilled holes.

A coating comprising an initial dose or first dose of a compound of the present application or pharmaceutically acceptable salt thereof, in immediate release form, can be added to the outside of a controlled-release tablet core comprising a second dose of a compound of the present application or pharmaceutically acceptable salt thereof, to produce a final dosage form. Such a coating can be prepared by admixing the first dosage with polyvinylpyrrolidone (PVP) 29/32 or hydroxypropyl methylcellulose (HPMC) and water/isopropyl alcohol and triethyl acetate. Such an immediate-release coating can be spray coated onto the tablet cores. The immediate-release coating can also be applied using a press-coating process with a blend consisting of 80% by weight promethazine and 20% by weight of lactose and hydroxypropyl methylcellulose type 2910. Press-coating techniques are known in the art.

The immediate-release or controlled-release dosage forms of the present application can also take the form of a multilayer tablet, such as a bi-layered tablet, which comprises a first layer and a second layer. In a further aspect of the bi-layered tablet, the first layer is an immediate release layer and/or the second layer is a controlled-release layer. For example, a multilayered tablet can comprise at least one immediate release layer comprising an amount of a compound of the present application or pharmaceutically acceptable salt thereof and at least one controlled release layer which comprises an amount of a compound of the present application or a pharmaceutically acceptable salt thereof. The controlled release layer may provide sustained release of a compound of the present application or pharmaceutically acceptable salt thereof, for a period of time. Alternatively, the immediate release layer and the controlled released layer may provide sustained release of a compound of the present application or pharmaceutically acceptable salt thereof, but at different dosage amounts.

The immediate-release or controlled release dosage forms of the present application can also take the form of pharmaceutical particles manufactured by a variety of methods, including but not limited to high-pressure homogenization, wet or dry ball milling, or small particle precipitation. Other methods to make a suitable powder formulation are the preparation of a solution of active ingredients and excipients, followed by precipitation, filtration, and pulverization, or followed by removal of the solvent by freeze-drying, followed by pulverization of the powder to the desired particle size. These dosage forms can include immediate-release particles in combination with controlled-release particles in a ratio sufficient useful for delivering the desired dosages of active agents.

In another aspect of the present application, the components are released from a multi-layered tablet that comprise at least a first layer, a second layer and a third layer. Wherein, the layers containing a therapeutically active agent can be optionally separated by one or more layers of inert materials. In one embodiment the layers containing an agent have similar rates of release, e.g. all are immediate release or all are controlled-release. In an alternative embodiment the layers have different rates of release. In this aspect at least one layer is an immediate release layer and at least one layer is a controlled release layer.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Transdermal delivery systems manufactured as an adhesive disc or patch that slowly releases the active ingredient for percutaneous absorption may be used. To this end, permeation enhancers may be used to facilitate transdermal penetration of the active agent. For example, for transdermal administration, the compounds herein may be combined with skin penetration enhancers, such as propylene glycol, polyethylene glycol, isopropanol, ethanol, oleic acid, N-methylpyrrolidone, dimethyl sulfoxide, and the like, which increase the permeability of the skin to the compounds, and permit them to penetrate through the skin and into the bloodstream. The compounds herein may also be combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. The compounds may be administered transdermally to achieve a local concentration of the active agent or to achieve systemic administration of the active agent.

Generally speaking, transdermal drug delivery systems are commonly either reservoir-type or matrix-type devices. Both types of devices include a backing layer that forms the outer surface of the finished transdermal device and which is exposed to the environment during use, and a release liner or protective layer that forms the inner surface and which covers the adhesive means for affixing the devices to the skin or mucosa of a user. The release liner or protective layer is removed prior to application, exposing the adhesive means which is typically a pressure-sensitive adhesive. The active agent is located between the release liner and backing layer, usually solubilized or dispersed in a solvent or carrier composition. In some embodiments, the outer surface of the transdermal device (e.g., patch) is adapted to associate with a second component, such as a heating compartment (e.g., electrical or chemical means for providing controlled and consistent increase in temperature).

In some embodiments, the present invention provides a kit comprising, consisting essentially of or consisting of a compound or pharmaceutical composition of the present invention and instructions for using the compound or pharmaceutical composition to prevent, monitor and/or treat a disorder. In some embodiments, the subject is an animal, such as a human. In some embodiments, the kit further comprises at least one other agent for use in the treatment of cancer, for reducing side effects induced by the compound of the application, and/or for enhancing the therapeutic efficacy of the compound of the application.

In some embodiments, the present invention provides a kit comprising, consisting essentially of or consisting of a composition of the present invention, a supplemental composition and instructions for using the composition of the present invention and the supplemental composition to prevent, monitor and/or treat a disorder.

Kits of the present invention may comprise instructions for preventing, monitoring and/or treating any suitable disorder, including, but not limited to, cancer. In some embodiments, the disorder is a gastrointestinal cancer, such as an anal cancer, an esophageal cancer, a stomach cancer, a liver cancer, a gallbladder cancer, a pancreatic cancer, a colon cancer or a rectal cancer. In some embodiments, the disorder is lung cancer.

Kits of the present invention may comprise instructions for preventing, monitoring and/or treating a disorder in any suitable subject, including, but not limited to, human subjects.

Another aspect of the present invention is a kit for preventing, treating and/or supplementing treatment of a disorder in a subject comprising, consisting essentially of or consisting of a compound, pharmaceutical composition or nutraceutical composition of the present invention and instructions for using the compound, the pharmaceutical composition or the nutraceutical composition.

In one aspect, the kit includes a compound of Formula I:

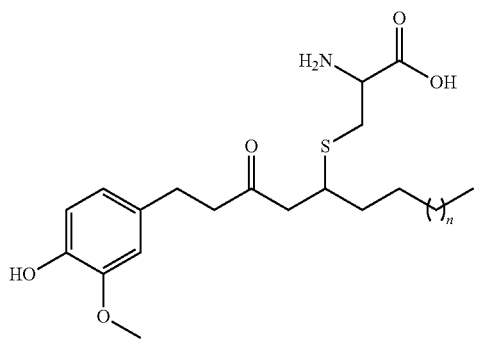

Formula I wherein n is 2, 4 or 6 or a pharmaceutically acceptable salt or hydrate thereof. In one embodiment of the kit comprises a compound of Formula I wherein n is 2; in another embodiment, n is 4 and in yet another embodiment, n is 6. In another embodiment, the kit comprises one or more of the compounds of Formula I, such as a kit comprising a compound where n is 2 and a compound where n is 4, or a compound where n is 2 and a compound where n is 6 or a compound where n is 4 and a compound where n is 6. Alternately, such a kit comprises a compound where n is 2 and a compound where n is 4 and a compound where n is 6. In one variation of any disclosed aspect or embodiment, the compound is in an isolated or purified form; alternately the compound is in a synthetic reaction mixture.

In another aspect, the kit includes a compound of Formula II:

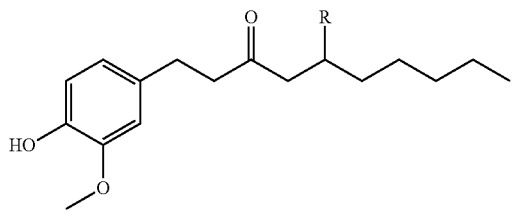

Formula II or a pharmaceutically acceptable salt or hydrate thereof wherein R is

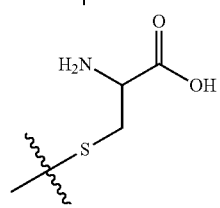

or and any diastereomers thereof. In one variation, the compound is in an isolated or purified form; alternately the compound is in a synthetic reaction mixture.

In one variation, the kit includes:

or a pharmaceutically acceptable salt or hydrate thereof in an isolated or purified form. In another variation, the kit includes:

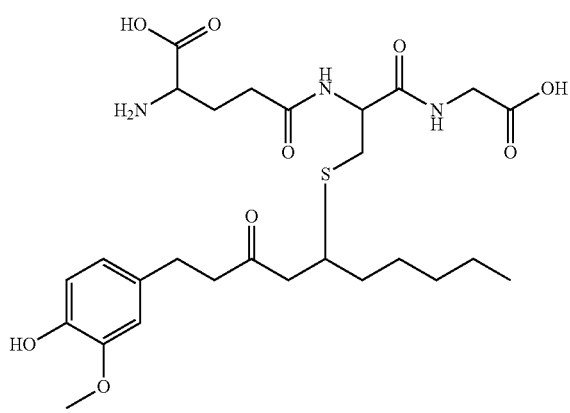 [SMILES: CCCCCC(CC(=O)CCc1ccc(O)c(OC)c1)SCC(NC(=O)CCC(N)C(=O)O)C(=O)NCC(=O)O]

or a pharmaceutically acceptable salt or hydrate thereof in an isolated or purified form.

In another aspect, the kit includes a compound of Formula III:

Formula III

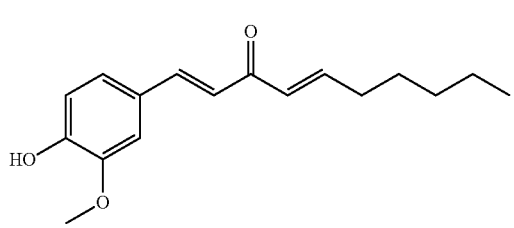

or a pharmaceutically acceptable salt or hydrate thereof. In one variation, the compound is in an isolated or purified form; alternately the compound is in a synthetic reaction mixture.

In one aspect, the kit includes one or more compounds having the formula:

M6

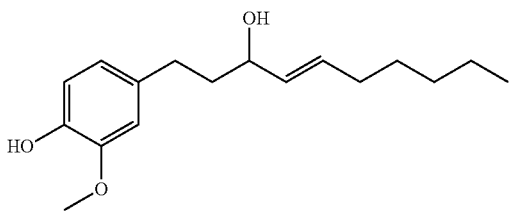

M9

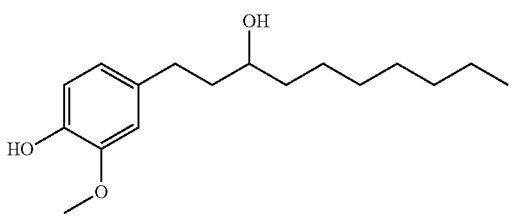

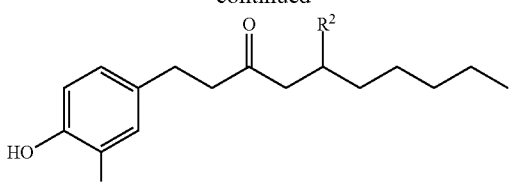

M7: $R^1$ = OMe; R2 = OMe
M8: $R^1$ = OH; R2 = H
M11: $R^1$ = OMe; R2 = H

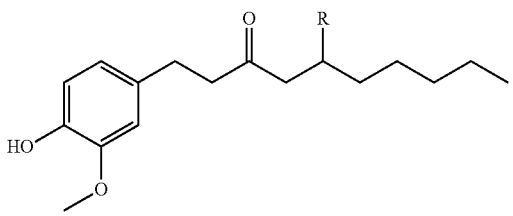

M2: R = cysteinyl
M5: R = N-acetylcysteinyl
M10: R = SMe
M13: R = glutathionyl

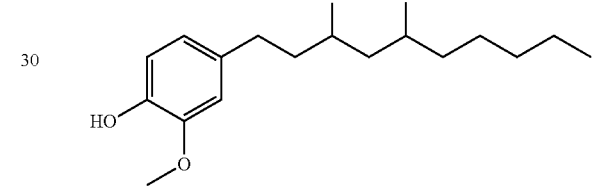

M1: R = cysteinyl
M3: R = Cysteinylglycinyl
M4: R = N-acetylcysteinyl
M12: R = SMe Cysteinyl:

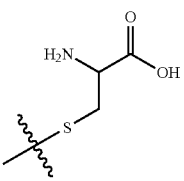

Glutathionyl: 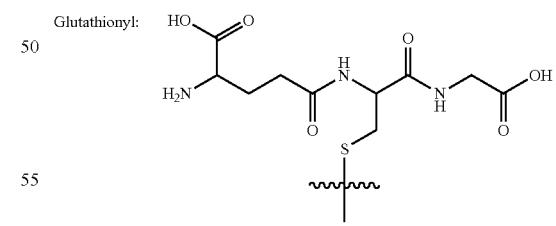

N-acetylcysteinyl: 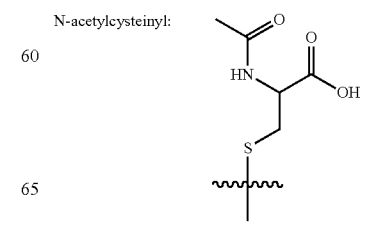

Cysteinylglycinyl:

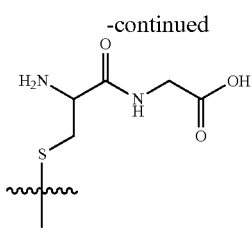

or a pharmaceutically acceptable salt or hydrate thereof. In one variation, the compound is in an isolated or purified form. In another variation, the compound is in a synthetic reaction mixture.

In another aspect, the kit includes M14 or M15:

M14

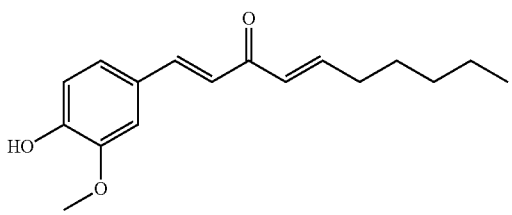

M15

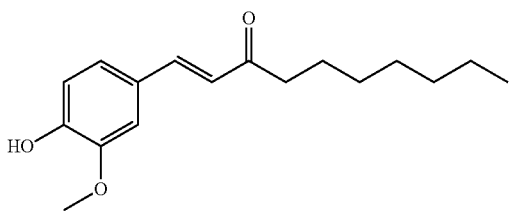

or a pharmaceutically acceptable salt or hydrate thereof. In one variation, the compound is in an isolated or purified form. In another variation, the compound is in a synthetic reaction mixture.

In yet another aspect, the kit includes one or more of:

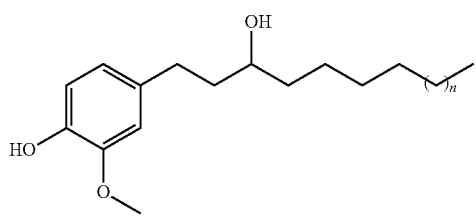

M9: $n = 2$;
M9': $n = 4$;
M9": $n = 6$;

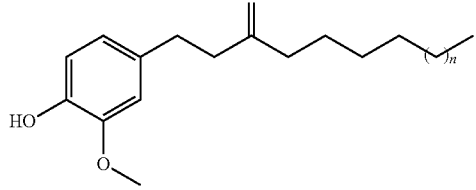

M11: $n = 2$;
M11': $n = 4$;
M11": $n = 6$;

or a pharmaceutically acceptable salt or hydrate thereof. In one embodiment, the kit includes one or more of M9, M9' and M9" or a pharmaceutically acceptable salt or hydrate thereof. In another embodiment, the kit includes one or more of M11, M11' and M11" or a pharmaceutically acceptable salt or hydrate thereof. In one variation of any disclosed aspect or embodiment, the kit does not include M2, M9 or M11. In another variation, the kit includes M2, M2', M2", M9, M9', M9", M11, M11' and M11" or a pharmaceutically acceptable salt. In yet another variation, the kit includes M2', M2", M9', M9", M11' and M11". In one variation of any aspect or embodiment, the compound is in an isolated or purified form. In another variation, the compound is in a synthetic reaction mixture.

Pharmaceutical and Nutraceutical Administration

In some embodiments, the compound is administered parenterally. In some embodiments, the compound is administered orally.

For the purposes of this application, the compounds of the present application or pharmaceutically acceptable salt thereof may be administered by a variety of means including orally, parenterally, by inhalation spray, topically, or rectally in formulations containing pharmaceutically acceptable carriers, adjuvants and vehicles. The compound can also be administered as depot formulations. Pharmaceutical compositions containing the active ingredient may be in any form suitable for the intended method of administration.

The term parenteral as used herein includes subcutaneous, intravenous, intramuscular, and intraarterial injections with a variety of infusion techniques. Intraarterial and intravenous injection as used herein includes administration through catheters.

It will be understood that the specific dose level for any particular patient will depend on a variety of factors including the activity of the specific compound employed; the age, body weight, general health, sex and diet of the individual being treated; the time and route of administration; the rate of excretion; other drugs which have previously been administered, as is well understood by those skilled in the art. Convenient dosing includes, but is not limited to, a once a day or twice a day administration, such as a tablet or capsule, as well as intravenous infusions. The use of time-release preparations to control the rate of release of the active ingredient as well as continuous infusions may also be employed. The dose may be administered in as many divided doses as is convenient.

Unit dosage formulations can be those containing a daily dose or unit, daily sub-dose, or an appropriate fraction thereof, of compound of the present application or a pharmaceutically acceptable salt thereof. The unit dose may be for oral consumption, such as by a tablet or capsule, or for infusion, or administered by other means as disclosed herein. In some embodiments, the dose amount is provided once a day, twice a day, 3 times a day, or 4 or more times a day. In other embodiments, the dose amount is provided twice a week, once a week, twice a month or once a month. For example, a dose can be provided twice a day, 3 times a day, or 4 or more times a day. In some embodiments, such a dose is provided twice a week, once a week, twice a month or once a month. The amount may be provided by oral consumption, infusion, or administered by other means familiar to those of skill in the art, such as transdermal or transmucosal.

In other embodiments, the unit dose may be provided as an infusion. For example, the compositions described herein can be administered intravenously, such as by an IV drip using IV solutions well known in the art (e.g., isotonic saline (0.9% NaCl) or dextrose solution (e.g., 5% dextrose), optionally the intravenous solution further includes preservatives, e.g. sodium metabisulfite). For example, a dose can be provided by infusion, such as by IV drip once a day, twice a week, once a week, twice a month or once a month. Alternately, the unit dose is infused once a day, twice a day, 3 times a day, or 4 or more times a day, for a period of time.

In other embodiments, the unit dose is from about 0.5 to about 500 mg/kg, and all ranges within, of compound of the present application or pharmaceutically acceptable salt thereof.

In some embodiments, the unit dose is at least about 2 µg/kg to 500 mg/kg, and all ranges within of a compound of the present application or pharmaceutically acceptable salt thereof.

Treatment

The present invention provides methods of 1) preventing, diagnosing, monitoring and/or treating a disorder in a subject in need thereof, 2) reducing one or more adverse effects associated with the treatment of a disorder and/or 3) increasing therapeutic efficacy in the treatment of a disorder.

In some embodiments, the method comprises, consists essentially of or consists of preventing and/or treating a disorder in a subject in need thereof, comprising, consisting essentially of or consisting of administering to said subject a therapeutically effective amount of a composition comprising, consisting essentially of or consisting of a compound of Formula I, II, or III.

In some embodiments, the method comprises, consists essentially of or consists of preventing and/or treating a disorder in a subject in need thereof, comprising, consisting essentially of or consisting of administering to said subject a pharmaceutical composition comprising, consisting essentially of or consisting of a compound of Formula I, II, or III and a pharmaceutically acceptable carrier.

In some embodiments, the method comprises, consists essentially of or consists of preventing, treating, and/or supplementing the treatment of a disorder in a subject in need thereof, comprising, consisting essentially of or consisting of administering to said subject a nutraceutical composition comprising, consisting essentially of or consisting of a compound of Formula I, II, or III and an acceptable carrier.

In some embodiments, the method comprises, consists essentially of or consists of administering to said subject a therapeutically effective amount of a composition of the present invention. In some such embodiments, the therapeutically effective amount comprises a prevention effective amount. In some embodiments, the therapeutically effective amount comprises a treatment effective amount.

In some embodiments, the method comprises, consists essentially of or consists of administering to said subject a therapeutically effective amount of a compound of Formula I:

Formula I

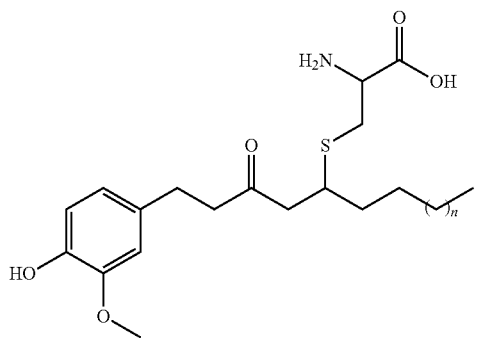

wherein n is 2, 4, 6 or combinations thereof. In one variation the method comprises administering a pharmaceutically acceptable salt or hydrate of said compound. In one embodiment of the compound of Formula I, n is 2; in another embodiment, n is 4 and in yet another embodiment, n is 6. In another embodiment, the kit comprises one or more of the compounds of Formula I, such as a kit comprising a compound where n is 2 and a compound where n is 4, or a compound where n is 2 and a compound where n is 6 or a compound where n is 4 and a compound where n is 6. Alternately, such a kit comprises a compound where n is 2 and a compound where n is 4 and a compound where n is 6. In one variation of any aspect or embodiment, the compound is in an isolated or purified form; alternately the compound is in a synthetic reaction mixture.

In another aspect, the method comprises, consists essentially of or consists of administering to said subject a therapeutically effective amount of a compound of Formula II:

Formula II

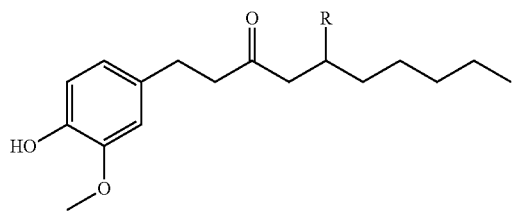

or a pharmaceutically acceptable salt or hydrate thereof wherein R is

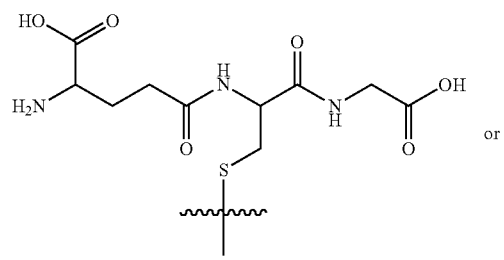 or

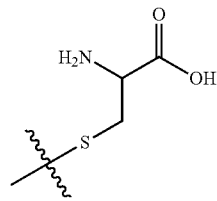

and any diastereomers thereof. In one variation the compound is in an isolated or purified form; alternately the compound is in a synthetic reaction mixture.

In one variation, the method comprises, consists essentially of or consists of administering to said subject a therapeutically effective amount of a compound of the formula:

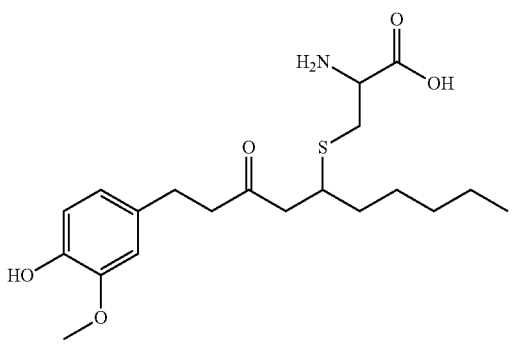 [SMILES: CCCCCC(CC(=O)CCc1ccc(O)c(OC)c1)SCC(N)C(=O)O]

or a pharmaceutically acceptable salt or hydrate thereof. In one variation, the compound is in an isolated or purified form; alternately the compound is in a synthetic reaction mixture. In another variation, the method comprises, consists essentially of or consists of administering to said subject a therapeutically effective amount of a compound of the formula:

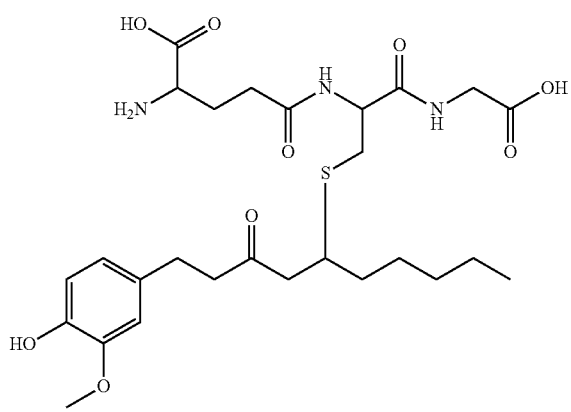 [SMILES: CCCCCC(CC(=O)CCc1ccc(O)c(OC)c1)SCC(NC(=O)CCC(N)C(=O)O)C(=O)NCC(=O)O]

or a pharmaceutically acceptable salt or hydrate thereof. In one variation, the compound is in an isolated or purified form; alternately the compound is in a synthetic reaction mixture.

In one aspect, the method comprises, consists essentially of or consists of administering to said subject a therapeutically effective amount of a compound of Formula III:

Formula III

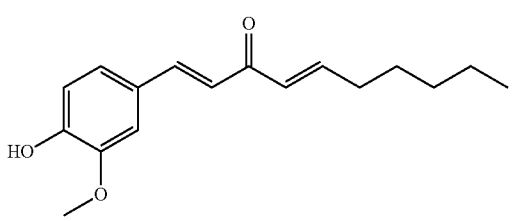

or a pharmaceutically acceptable salt or hydrate thereof. In one variation, the compound is in an isolated or purified form; alternately the compound is in a synthetic reaction mixture.

In one aspect, the method comprises, consists essentially of or consists of administering to said subject a therapeutically effective amount of a compound of the formula:

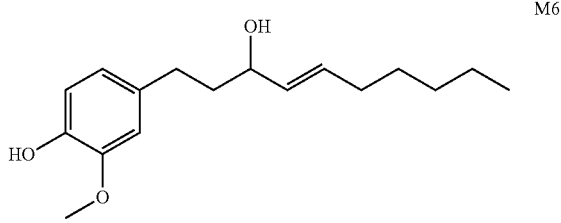
M6

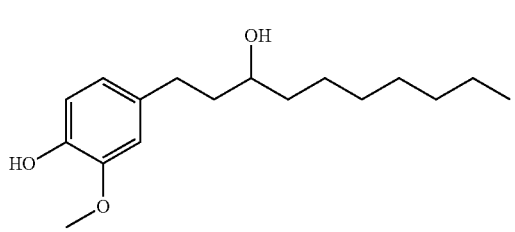
M9

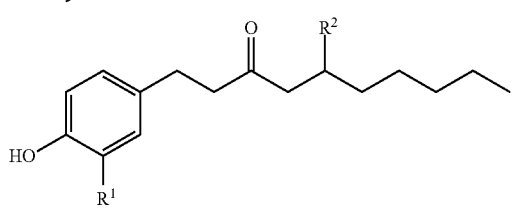

M7: $R^1$ = OMe; R2 = OMe
M8: $R^1$ = OH; R2 = H
M11: $R^1$ = OMe; R2 = H

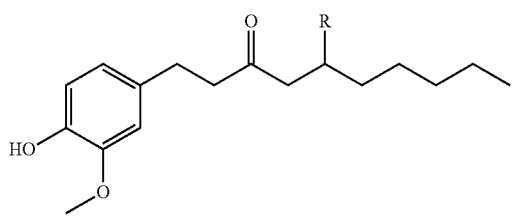

M2: R = cysteinyl
M5: R = N-acetylcysteinyl
M10: R = SMe
M13: R = glutathionyl

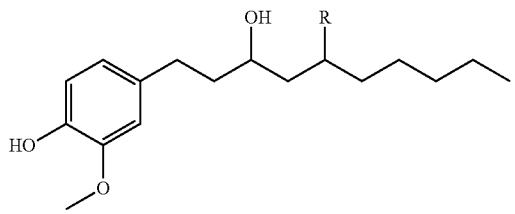

M1: R = cysteinyl
M3: R = Cysteinylglycinyl
M4: R = N-acetylcysteinyl
M12: R = SMe Cysteinyl:

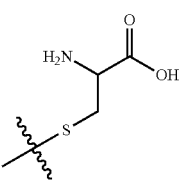

Glutathionyl: 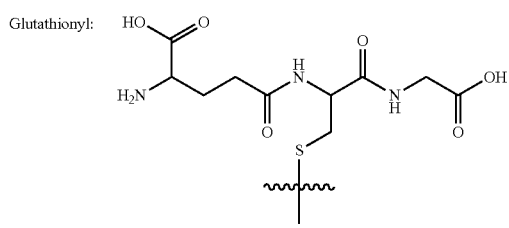

N-acetylcysteinyl: 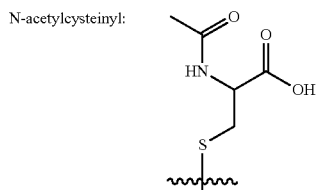

Cysteinylglycinyl: 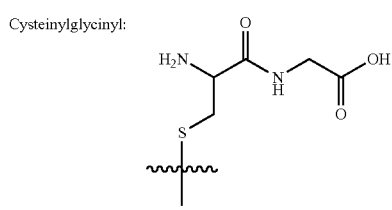

or a pharmaceutically acceptable salt or hydrate thereof. In one variation, the compound is in an isolated or purified form. In another variation, the compound is in a synthetic reaction mixture.

In another aspect, the method comprises, consists essentially of or consists of administering to said subject a therapeutically effective amount of M14 or M15:

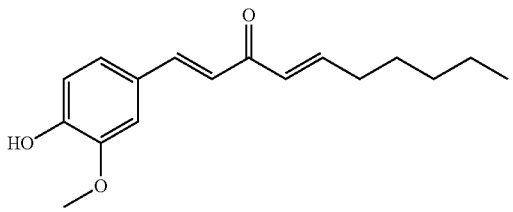

M14

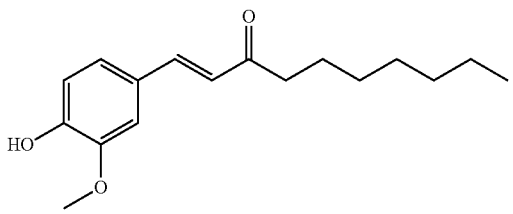

M15 or a pharmaceutically acceptable salt or hydrate thereof. In one variation, the compound is in an isolated or purified form. In another variation, the compound is in a synthetic reaction mixture.

In yet another aspect, the method comprises, consists essentially of or consists of administering to said subject a therapeutically effective amount of a compound of the formula:

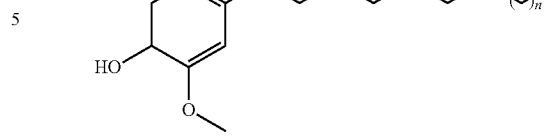

M9: $n = 2$;
M9': $n = 4$;
M9'': $n = 6$;

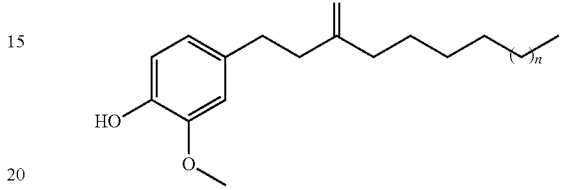

M11: $n = 2$;
M11': $n = 4$;
M11'': $n = 6$;

or a pharmaceutically acceptable salt or hydrate thereof. In one embodiment, the method comprises administering one or more of M9, M9' and M9'' or a pharmaceutically acceptable salt or hydrate thereof. In another embodiment, the method comprises administering one or more of M11, M11' and M11'' or a pharmaceutically acceptable salt or hydrate thereof. In one variation of any disclosed aspect or embodiment, the method comprises administering a composition that does not include M2, M9 or M11. In another variation, the method comprises administering a composition that comprises M2, M2', M2'', M9, M9', M9'', M11, M11' and M11'' or a pharmaceutically acceptable salt. In yet another variation, the method comprises administering a composition that comprises M2', M2'', M9', M9'', M11' and M11''. In one variation of any aspect or embodiment, the compound is in an isolated or purified form. In another variation, the compound is in a synthetic reaction mixture.

In some embodiments, the method comprises, consists essentially of or consists of administering to said subject a therapeutically effective amount of a pharmaceutical composition of the present invention.

In some such embodiments, the composition is a compound of the present invention. In some such embodiments, the composition is a pharmaceutical composition of the present invention. In other such embodiments, the composition is a nutraceutical composition of the present invention.

In some embodiments, administration of the composition results in the prevention and/or treatment of a first disorder and the prevention and/or treatment of a second disorder. For example, administration of the composition may result in the treatment of rectal cancer and the prevention of colon cancer (by preventing metastasis, for example).

In some embodiments, the subject exhibits one or more risk factors associated with the disorder. For example, the subject may have a familial history of cancer, one or more pre-cancerous lesions, premalignant cells, preneoplastic cells or other aberrant phenotypes indicating probably progression to a cancerous state.

In some embodiments, the subject is a human.

Combination Therapy

In certain embodiments of the present application, the compounds of the present application can be used in a combination therapy with at least one other therapeutic agent. The compounds and the therapeutic agent can act additively or, more preferably, synergistically.

In some embodiments, the other therapeutic agent is an antitumor alkylating agent, antitumor antimetabolite, antitumor antibiotics, plant-derived antitumor agent, antitumor organoplatinum compound, antitumor campthotecin derivative, antitumor tyrosine kinase inhibitor, monoclonal antibody, interferon, biological response modifier, hormonal anti-tumor agent, angiogenesis inhibitor, differentiating agent, or a pharmaceutically acceptable salt thereof. In some embodiments, the compound is administered in combination with surgery, radiation therapy, chemotherapy, gene therapy, RNA therapy, adjuvant therapy, immunotherapy, nanotherapy or a combination thereof. In some embodiments, the method further comprises administering to the subject a therapeutically effective amount of a pharmaceutical composition, the composition comprising a compound of the present application and a pharmaceutically acceptable carrier. In some embodiments, the subject is a mammal. In some embodiments, the subject is a human.

Combination therapy includes the administration of a compound or salt of the present application and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). Combination therapy can be carried out either sequentially or substantially simultaneously. In the case of sequential administration of more than one therapeutic agent, each therapeutic agent is administered at a different time. In the case of simultaneous administration, at least two of the therapeutic agents are administered in a substantially simultaneous manner, either in the same pharmaceutical composition or in different pharmaceutical compositions. Substantially simultaneous administration can be accomplished, for example, by administering to the subject a single capsule having a fixed ratio of each therapeutic agent or in multiple, single capsules for each of the therapeutic agents. In one embodiment, a composition comprising a compound of the application is administered concurrently with the administration of another therapeutic agent, which can be part of the same composition as the compound of the application or a different composition.

In another embodiment, a composition comprising a compound of the application is administered prior to, or subsequent to, administration of another therapeutic agent. The therapeutic agents can be administered in a variety of combinations. In some embodiments, the therapeutic agents are administered within about 1 minute, 5 minutes, 10 minutes, 15 minutes, 20 minutes, 25 minutes, 30 minutes, 40 minutes, 50 minutes, 1 hour, 1.5 hours, 2 hours, 2.5 hours, 3 hours, 3.5 hours, 4 hours, 4.5 hours, 5 hours, 5.5 hours, 6 hours, 7 hours, 8 hours, 9 hours, 10 hours, 11 hours, 12 hours, 1 day, 2 days, 3 days, 4 days, 5 days, 6 days, 1 week, 2 weeks, 3 weeks or 4 weeks of one another, or any ranges there between.

Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected can be administered by intravenous injection while the other therapeutic agents of the combination can be administered orally. Alternatively, for example, all therapeutic agents can be administered orally or all therapeutic agents can be administered by intravenous injection. The sequence in which the therapeutic agents are administered is not narrowly critical.

Combination therapy also encompasses the administration of the compound as described above in further combination with other therapies including but not limited to chemotherapy, surgery, radiation therapy, gene therapy, immunotherapy, RNA therapy, adjuvant therapy, nanotherapy or a combination thereof. Where the combination therapy further comprises a non-drug treatment, the non-drug treatment can be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, by a significant period of time. The compound and the other pharmacologically active agent can be administered to a patient simultaneously, sequentially or in combination. It will be appreciated that when using a combination of the application, the compound of the application and the other pharmacologically active agent can be in the same pharmaceutically acceptable carrier and therefore administered simultaneously. They can be in separate pharmaceutical carriers such as conventional oral dosage forms which are taken simultaneously. The term "combination" further refers to the case where the compounds are provided in separate dosage forms and are administered sequentially.

In some embodiments, treatment of cancer with a compound of the present application is accompanied by administration of pharmaceutical agents that can alleviate the side effects produced by the antineoplastic agents.

EXAMPLES

The following examples are for illustrative purposes only and are not intended to be a detailed catalogue of all the different ways in which the present invention may be implemented or of all the features that may be added to the present invention.

Starting materials useful for preparing compounds of the present invention and intermediates thereof are commercially available and/or can be prepared by well-known synthetic methods. Other methods for synthesis of the compounds described herein are either described in the art or will be readily apparent to the skilled artisan in view of the references provided above and can be used to synthesize conjugates of the application. One skilled in the art will therefore appreciate that the following Examples are exemplary and that numerous changes, modifications, and alterations can be employed without departing from the scope of the presently disclosed subject matter.

EXPERIMENTAL PART 1

Materials and Methods

[6]-Shogaol was purified from ginger extract using methods disclosed in Sang S, et al., (2009) J Agric Food Chem 57:10645-10650. Sephadex LH-20, reverse-phase C18 silica gels, analytical and preparative thin-layer chromatography (TLC) plates 250- and 2000-μm thickness, 2-25-μm particle size), and CDCl$_3$ were purchased from Sigma-Aldrich (St. Louis, Mo.). High-performance liquid chromatography (HPLC)-grade solvents and other reagents were obtained from VWR Scientific (South Plainfield, N.J.). All other chemicals were purchased from Sigma (St. Louis, Mo.) or Thermo Fisher Scientific (Waltham, Mass.). Anhydrous reactions were carried out in oven-dried glassware under a nitrogen atmosphere unless otherwise noted. Analytical (250 μm thickness, 2-25 μm particle size) and preparative TLC plates (2000 μm thickness, 2-25 μm particle size) were purchased from Sigma (St. Louis, Mo.) and Sorbent Technologies (Atlanta, Ga.), respectively. Microsomes and NADPH-regenerating systems were procured from BD Biosciences (Bedford, Mass.). 1-Aminobenzotriazole (ABT), 18β-glyccerhetinic acid (18β-GA), and 2,3-dichloro-5,6-dicyano-1,4-benzoquinone (DDQ) were purchased from Sigma Aldrich (St. Louis, Mo.). Liquid chromatography/mass spectrometry (LC/MS)-grade MeOH and water were obtained from Thermo Fisher Scientific (Waltham, Mass.). HCT-116 and HT-29 human colon cancer cells, H-1299 human lung cancer cells, and CL-13 mouse lung cancer cells, CCD-18Co human fibroblast cells derived from colon, IMR-90 human diploid fibroblast cells derived from lung, and Eagle's minimum essential media (EMEM) were obtained from the American Type Culture Collection (Manassas, Va.). McCoy's 5A medium was purchased from Mediatech (Herndon, Va.) or Thermo Fisher Scientific (Waltham, Mass.). Fetal bovine serum (FBS) and penicillin/streptomycin were purchased from Gemini Bio-Products (West Sacramento, Calif.). MTT (3-(4,5-dimethylthiaxol-2-yl)-2,5-diphenyltetrazolium bromide) was procured from Calbiochem-Novabiochem (San Diego, Calif.). Proteinase K was obtained from Ambion (Austin, Tex.). Apoptag Plus Peroxydase In Situ Apoptosis Detection Kit was purchased from Millipore Corporation (Billerica, Mass.). Glutathione, sulfatase from *Aerobacter aerogenes*, and β-glucuronidase from *Helix aspersa* were obtained from Sigma Aldrich (St. Louis, Minn.).

Nuclear Magnetic Resonance.

$^1$H (600 MHz), $^{13}$C (150 MHz), and all two-dimensional (2D) NMR spectra were acquired on a Bruker AVANCE 600 MHz NMR spectrometer (Brucker, Inc., Silberstreifen, Rheinstetten, Germany). Compounds were analyzed in CDCl$_3$ or CD$_3$OD. Multiplicities are indicated by s (singlet), d (doublet), t (triplet), q (quartet), and br (broad). The $^{13}$C NMR spectra are proton decoupled.

HPLC Analysis.

An HPLC ESA electrochemical detector (ECD) (ESA, Chelmsford, Mass.) consisting of an ESA model 584 HPLC pump, an ESA model 542 autosampler, an ESA organizer, and an ESA ECD coupled with two ESA model 6210 four sensor cells was used. A Gemini C18 column 150×4.6 mm, 5 μm; Phenomenex, Torrance, Calif.) was used for chromatographic analysis at a flow rate of 1.0 ml/min. The mobile phases consisted of solvent A (30 mM sodium phosphate buffer containing 1.75% acetonitrile and 0.125% tetrahydrofuran, pH 3.35) and solvent B (15 mM sodium phosphate buffer containing 58.5% acetonitrile and 12.5% tetrahydrofuran, pH 3.45). The gradient elution had the following profile: 20% solvent B from 0 to 3 min; 20 to 55% solvent B from 3 to 11 min; 55 to 60% solvent B from 11 to 12 min; 60 to 65% solvent B from 12 to 13 min; 65 to 100% solvent B from 13 to 40 min; 100% solvent B from 40 to 45 min; and then 20% solvent B from 45.1 to 50 min. The cells were then cleaned at a potential of 1000 mV for 1 min. The injection volume of the sample was 10 μl. The eluent was monitored by the Coulochem electrode array system (ESA) with potential settings at −100, 0, 100, 200, 300, 400, and 500 mV.

Waters preparative HPLC system (Waters, Milford, Mass.) with 2545 binary gradient module, Waters 2767 sample manager, Waters 2487 autopurification flow cell, Waters fraction collector III, dual injector module, and a 2489 UV/visible detector was used to purify metabolites M6 through M8 and M12. A Gemini-NX C18 column (250×30.0 mm i.d., 5 μm; Phenomenex) was used with a flow rate of 20.0 ml/min, and the separation was performed with a mobile phase of MeOH/H2O. The gradient elution had the following profile: 70% solvent B from 0 to 30 min; 70 to 100% solvent B from 30 to 31 min; 100% solvent B from 31 to 36 min; 100 to 70% solvent B from 36 to 37 min; and then 70% solvent B from 37 to 42 min. The wavelength of the UV detector was set at 230 nm. Water and methanol were used as mobile phases A and B, respectively.

Liquid Chromatography/Electrospray Ionization-Mass Spectrometry Method.

LC/MS analysis was performed with a Thermo-Finnigan Spectra System, which consisted of an Accela high-speed mass spectrometry (MS) pump, an Accela refrigerated autosampler, and an LTQ Velos ion trap mass detector (Thermo Fisher Scientific) incorporated with heated electrospray ionization (H-ESI) interfaces. A Gemini C18 column (50×2.0 mm i.d., 3 μm; Phenomenex) was used for separation at a flow rate of 0.2 ml/min. The column was eluted from 100% solvent A (5% aqueous methanol with 0.2% acetic acid) for 3 min, followed by linear increases in solvent B (95% aqueous methanol with 0.2% acetic acid) to 40% from 3 min to 15 min, to 85% from 15 to 45 min, to 100% from 45 to 50 min, and then with 100% solvent B from 50 to 55 min. The column was then re-equilibrated with 100% solvent A for 5 min. The liquid chromatography (LC) eluent was introduced into the H-ESI interface.

The positive ion polarity mode was set for the H-ESI source with the voltage on the H-ESI interface maintained at approximately 4.5 kV. Nitrogen gas was used as the sheath gas and auxiliary gas. Optimized source parameters, including ESI capillary temperature (300° C.), capillary voltage (50 V), ion spray voltage (3.6 kV), sheath gas flow rate (30 units), auxiliary gas flow rate (5 units), and tube lens (120 V), were tuned using authentic [6]-shogaol. The collision-induced dissociation was conducted with an isolation width of 2 Da and normalized collision energy of 35 for MS$^2$ and MS$^3$. Default automated gain control target ion values were used for MS, MS$^2$, and MS$^3$ analyses. The mass range was measured from 50 to 1000 m/z. Data acquisition was performed with Xcalibur 2.0 version (Thermo Fisher Scientific).

Experimental Part 1

Treatment of Mice and Sample Collections

Female C57BL/6J mice and female A/J mice were purchased from The Jackson Laboratory (Bar Harbor, Me.) and were allowed to acclimate for at least 1 week before the start of the experiment. Mice were housed five per cage and maintained in air-conditioned quarters with a room temperature of 20±2° C., relative humidity of 50±10%, and an alternating 12-h light/dark cycle. Mice were fed Purina Rodent Chow number 5001 (Research Diets; Purina, St. Louis, Mo.) and water and were allowed to eat and drink ad libitum.

24-h urinary and fecal samples were collected using metabolic cages for metabolic profile analysis. In brief, [6]-shogaol in corn oil or corn oil only was administered to C57BL/6J mice by oral gavage (200 mg/kg). Fecal and urinary samples were collected in metabolic cages (five mice per cage) for 24 h after administration of vehicle (control group, n=5) or [6]-shogaol (treated group, n=5). In experiment 2, A/J mice were administrated [6]-shogaol by oral gavage (200 mg/kg per day) for 10 days. Fecal samples were collected from mouse cages every 5 days. The combined fecal samples were used to purify the major metabolites of [6]-shogaol. These samples were stored at −80° C. before analysis. In experiment 3, NJ mice were treated with either 200 mg/kg [6]-shogaol in corn oil or corn oil only by oral gavage. Blood was collected from anesthetized mice by cardiac puncture at 2 or 6 h after administration of vehicle or [6]-shogaol (five mice per time point), and plasma was isolated by centrifugation at 5000 rpm for 15 min in a refrigerated centrifuge. Plasma samples were then stored at −80° C. until analysis.

Fecal, Urinary, and Plasma Sample Preparation.

For acquisition of the metabolic profile, six pieces of each fecal sample (control and treated) were chosen and put into 2-ml tubes. Each set was weighted (control, 128 mg; treated, 130 mg), and 1.2 ml of MeOH/H2O (50/50)+0.1% acetic acid was added to each sample. Samples were sonicated for 90 min and then centrifuged at 17,000 rpm for 10 min. The supernatant (250 µl) was collected and diluted five times for analysis. Enzymatic deconjugation was performed as described previously with slight modifications (Shao et al., (2010) Rapid Commun Mass Spectrom 24:1770-1778.). In brief, (250 µl) of supernatant were dried under reduced pressure at 37° C., and the residue was resuspended in sodium phosphate buffer (50 mM, pH 6.8). Samples were then treated with α-glucuronidase (250 units) and sulfatase (3 units) for 24 h at 37° C. and were extracted twice with ethyl acetate. The ethyl acetate fraction was dried under vacuum, and the solid was resuspended in 1.25 ml of 80% aqueous methanol with 0.1% acetic acid for further analysis. For preparation of the urinary and plasma samples, (50 µl) from each group (control group and [6]-shogaol treated group) were added to 1.2 ml of MeOH to precipitate proteins. After centrifugation at 17,000 rpm for 10 min, the supernatants were transferred into vials for analysis. Enzymatic deconjugation of the urinary and plasma samples was performed as described above. In brief, (50 µl) from each group (control group and [6]-shogaol-treated group) were treated with α-glucuronidase (250 units) and sulfatase (3 units) for 24 h at 37° C. and were extracted twice with ethyl acetate. The ethyl acetate fraction was dried under vacuum, and the solid was resuspended in 1.25 ml (for urine) or (250 µl) (for plasma) of 80% aqueous methanol with 0.1% acetic acid for further analysis.

Purification of the Major Mouse Fecal Metabolites of [6]-Shoqaol.

The mouse feces (228.29 g) collected as described above and were extracted with MeOH/H2O (50/50, 1000 ml each time) twice and then were extracted with MeOH five times (1000 ml each time). The extract was dried under reduced pressure at 37° C., and the residue (40.06 g) was dissolved in water (800 ml) and partitioned successively with ethyl acetate (5×500 ml) and 1-butanol (2×600 ml). The ethyl acetate-soluble portion (5.5 g) was subjected to a reverse-phase C18 column eluted with a MeOH/H2O gradient system (3:7, 4:6, 5:5, 6:4, 7:3, 8:2, 9:1; v/v; 800 ml for each gradient), giving 12 fractions. Fraction 7 was separated by preparative HPLC to give fractions 7a and 7b. Fraction 7a was successively separated on a preparative silica gel TLC plate (developed with CHCl3/MeOH, 100:1) and Sephadex LH-20 (eluted with EtOH) column chromatography (CC) to give M11 (17 mg). Fraction 7b was purified on a preparative silica gel TLC plate (developed with CHCl3/MeOH, 100:1) to yield two subfractions (7b1 and 7b2). Fraction 7b1 was first loaded on a preparative silica gel TLC plate (developed with n-hexane/EtOAc, 10:1) and then on Sephadex LH-20 (eluted with EtOH) CC to give M9 (0.5 mg) and M10 (0.8 mg). Fraction 7b2 was subjected to preparative HPLC to give M12 (0.6 mg). Fraction 8 was loaded on a preparative silica gel TLC plate (developed with n-hexane/EtOAc, 10:1) to give fractions 8a through 8c. Fraction 8a was subjected to preparative HPLC to give one major fraction, which was then successively separated on a preparative silica gel TLC plate (developed with CHCl3/MeOH, 100:1) and Sephadex LH-20 (eluted with EtOH) CC to give M6 (0.5 mg). Fraction 8b was subjected to Sephadex LH-20 (eluted with EtOH) CC and then preparative HPLC to give M7 (0.5 mg). Fraction 8c was first loaded on a preparative silica gel TLC plate (developed with n-hexane/EtOAc, 10:1) and then on preparative HPLC to give M8 (4.0 mg). $^1$H and $^{13}$C NMR data of M6 through M12 are listed in Tables 1 and 2.

TABLE 1

$^1$H and $^{13}$C NMR spectroscopic data of M6 through M9 and M11

| No. | M6[a] $\delta_H$ multi (J in Hz) | $\delta_C$ | M7[b] $\delta_H$ multi (J in Hz) | $\delta_C$ | M8[b] $\delta_H$ multi (J in Hz) | $\delta_C$ | M9[b] $\delta_H$ multi (J in Hz) | $\delta_C$ | M11[b] $\delta_H$ multi (J in Hz) | $\delta_C$ |
|---|---|---|---|---|---|---|---|---|---|---|
| 1' | | 133.6 | | 133.0 | | 134.1 | | 134.0 | | 133.1 |
| 2' | 6.77 br s | 111.6 | 6.71 d (1.2) | 111.0 | 6.72 br s | 115.4 | 6.71 d (1.5) | 111.0 | 6.70 br s | 111.0 |
| 3' | | 147.4 | | 146.3 | | 143.6 | | 146.4 | | 146.4 |
| 4' | | 144.0 | | 143.9 | | 141.9 | | 143.7 | | 143.9 |
| 5' | 6.70 br d (7.8) | 114.6 | 6.83 d (7.8) | 114.3 | 6.78 d (7.8) | 115.4 | 6.84 d (7.9) | 114.2 | 6.82 br d (7.9) | 114.3 |
| 6' | 6.63 br d (7.8) | 128.3 | 6.69 dd (7.8, 1.2) | 120.8 | 6.61 d (7.8) | 120.5 | 6.69 dd (8.0, 1.5) | 120.9 | 6.67 br d (7.9) | 120.8 |
| 1 | 2.58 m | 31.1 | 2.85 t (7.8) | 29.2 | 2.79 t (7.2) | 29.2[c] | 2.74 m; 2.62 m | 31.7 | 2.84 t (7.5) | 29.5 |
| 2 | 1.73 | 39.3 | 2.76 m | 45.8 | 2.70 | 43.4 | 1.78; 1.71 m | 39.4 | 2.70 t (7.5) | 44.6 |
| 3 | 3.99 m | 71.6 | | 209.0 | | 211.5 | 3.64 m | 71.4 | | 210.6 |
| 4 | 5.47 dd (15.4, 7.1) | 131.3 | 2.66 dd (16.2, 7.8); 2.42 dd (16.2, 4.8) | 47.6 | 2.38 t (7.4) | 43.2 | 1.48 m | 37.6 | 2.38 t (7.4) | 43.1 |

TABLE 1-continued $^1$H and $^{13}$C NMR spectroscopic data of M6 through M9 and M11

| No. | M6[a] $\delta_H$ multi (J in Hz) | $\delta_C$ | M7[b] $\delta_H$ multi (J in Hz) | $\delta_C$ | M8[b] $\delta_H$ multi (J in Hz) | $\delta_C$ | M9[b] $\delta_H$ multi (J in Hz) | $\delta_C$ | M11[b] $\delta_H$ multi (J in Hz) | $\delta_C$ |
|---|---|---|---|---|---|---|---|---|---|---|
| 5 | 5.64 dt (15.4, 7.1) | 132.9 | 3.67 m | 77.1 | 1.56 m | 23.8 | 1.30 m | 29.4 | 1.56 m | 23.8 |
| 6 | 2.06 m | 31.9 | 1.49 m; 1.43 m | 33.8 | 1.31 m | 29.0[c] | 1.30 m | 29.4 | 1.26 m | 29.0 |
| 7 | 1.29 m | 28.8 | 1.31 m | 24.7 | 1.31 m | 29.1[c] | 1.44 m; 1.32 m | 25.6 | 1.26 m | 29.0 |
| 8 | 1.31 m | 31.2 | 1.31 m | 31.9 | 1.31 m | 31.6 | 1.28 m | 31.7 | 1.26 m | 31.6 |
| 9 | 1.34 m | 22.2 | 1.31 m | 22.6 | 1.31 m | 22.6 | 1.30 | 22.6 | 1.29 m | 22.5 |
| 10 | 0.92 t (7.2) | 13.1 | 0.90 t (7.2) | 13.9 | 0.89 t (7.2) | 14.1 | 0.91 t (7.1) | 14.0 | 0.89 t (7.1) | 14.0 |
| 3'-OMe | 3.84 s | 54.8 | 3.89 s | 55.9 | | | 3.90 s | 55.9 | 3.87 s | 55.9 |
| 5-OMe | | | 3.30 s | 56.9 | | | | | | |
| 4'-OH | | | 5.47 s | | | | 5.47 s | | | |

[a]Data were measured in CD$_3$OD at 600 ($^1$H) and 150 MHz ($^{13}$C).
[b]Data were measured in CDCl$_3$ at 600 ($^1$H) and 150 MHz ($^{13}$C). Chemical shifts (δ) are in ppm being relative to CD$_3$OD and CDCl$_3$.
[c]Data can be exchanged with each other.

TABLE 2

$^1$H and $^{13}$C NMR spectroscopic data of [6]-shogaol, M10, M12, and synthetic 5-N-acetylcysteinyl-[6]-shogaol

| No. | [6]-Shogaol[a] $\delta_H$ multi (J in Hz) | $\delta_C$ | M10[b] $\delta_H$ multi (J in Hz) | $\delta_C$ | M12[b] $\delta_H$ multi (J in Hz) | $\delta_C$ | 5-N-acetylcysteinyl-[6]-shogaol[a] $\delta_H$ multi (J in Hz) | $\delta_C$ |
|---|---|---|---|---|---|---|---|---|
| 1' | | 132.6 | | 132.9 | | 134.0 | | 134.0 |
| 2' | 6.80 d (1.8) | 111.8 | 6.71 d (1.5) | 111.0 | 6.73 d (2.2) | 111.0 | 6.81 d (1.8) | 111.7 |
| 3' | | 147.6 | | 146.4 | | 146.4 | | 149.0 |
| 4' | | 144.5 | | 143.9 | | 143.7 | | 145.9 |
| 5' | 6.71 d (8.0) | 114.7 | 6.84 d (8.0) | 114.3 | 6.84 d (7.9) | 114.2 | 6.71 d (8.0) | 114.6 |
| 6' | 6.63 dd (8.0, 1.8) | 120.4 | 6.69 dd (8.0, 1.5) | 120.8 | 6.71 dd (7.9, 2.2) | 120.9 | 6.65 dd (8.0, 1.8) | 120.2 |
| 1 | 2.88 m | 31.1 | 2.86 t (7.5) | 29.3 | 2.64 m; 2.75 m | 31.7 | 2.80 m | 27.5 |
| 2 | 2.66 m | 41.3 | 2.75 m | 45.5 | 1.79 m; 1.74 m | 39.8 | 2.74 dd (17.1, 6.3); 2.67 dd (17.1, 6.3) | 49.7 |
| 3 | | 201.5 | | 208.4 | 4.00 m | 68.9 | | 211.2 |
| 4 | 6.12 br d (15.9) | 130.0 | 2.59 dd (16.6, 6.5); 2.69 dd (16.6, 6.5) | 48.5 | 1.71 m; 1.62 m | 40.6 | 2.74 m | 46.1 |
| 5 | 6.90 dt (15.9, 7.02) | 148.7 | 3.04 m | 41.6 | 2.75 m | 43.2 | 3.14 m | 42.6 |
| 6 | 2.22 m | 32.1 | 1.50 m | 34.4 | 1.61m | 34.8 | 1.51 m | 33.7 |
| 7 | 1.48 m | 27.6 | 1.42 m; 1.38 m | 26.5 | 1.44 m | 26.6 | 1.34 m | 26.6 |
| 8 | 1.34 m | 29.8 | 1.27 m | 31.6 | 1.31 m | 31.9 | 1.27 m | 30.9 |
| 9 | 1.34 m | 22.1 | 1.31 m | 22.6 | 1.31 m | 22.6 | 1.33 m | 22.2 |
| 10 | 0.93 t (7.1) | 13.0 | 0.90 t (7.1) | 14.0 | 0.91 t (7.1) | 14.1 | 0.92 | 14.4 |
| 3'-OME | 3.84 s | | 3.89 s | 55.9 | 3.90 s | 55.7 | | 56.4 |
| 5-SMe | | | 2.04 s | 13.3 | 2.05 | 12.3 | | |
| 4'-OH | | | 5.45 s | | 5.47 s | | | |
| 3-OH | | | | | 2.25 d (4.9) | | | |
| 1" | | | | | | | 3.00 dd (4.7, 13.7); 2.92 dd (7.1, 13.7) | 30.4 |
| 2" | | | | | | | 4.58 dd (7.1, 4.7) | 54.6 |
| 3" | | | | | | | | 173.1 |
| 4" | | | | | | | | 173.1 |
| 5" | | | | | | | 2.01 s | 22.6 |

[a]Data were measured in CD$_3$OD at 600 ($^1$H) and 150 MHz ($^{13}$C).
[b]Data were measured in CDCl$_3$ at 600 ($^2$H) and 150 MHz ($^{13}$C). Chemical shifts (δ) are in ppm being relative to CD$_3$OD and CDCl$_3$.

Synthesis of 5-N-Acetylcysteinyl-[6]-Shogaol

[6]-Shogaol (235 mg, 0.8 mmol) was dissolved in ethanol (40 ml) and added dropwise to a solution of N-acetylcysteine [1076 mg, 6.6 mmol in 100 ml of phosphate buffered saline (PBS) at pH 7.4] at 37° C. After stirring for 24 h, the reaction mixture was extracted with ethyl acetate. The organic phase was then separated and dried, and the residue (520 mg) was redissolved in MeOH. The reconstituted solution was subjected to a reverse-phase C18 column and was eluted with a mobile phase of MeOH/H$_2$O (70:30, v/v) at a flow rate of 2 ml/min. The samples were combined on the basis of the TLC analysis and were dried to obtain 240 mg (yield 64%) of final product. $^1$H and $^{13}$C NMR data of 5-N-acetylcysteinyl-[6]-shogaol are listed in Table 2.

Metabolism of [6]-Shogaol in Cancer Cells.

Cells (1.0×10$^6$) were plated in six-well culture plates and were allowed to attach for 24 h at 37° C. in 5% CO$_2$ incubator. [6]-Shogaol [in dimethyl sulfoxide (DMSO)] was added to McCoy's 5A medium (containing 10% fetal bovine serum, 1% penicillin/streptomycin, and 1% glutamine) to reach a final concentration of (10 μM) and was incubated with different cancer cell lines (HCT-116, HT-29, H-1299, and CL-13). At different time points (0, 30 min, 1, 2, 4, 6, 8, and 24 h), 190-μl samples of supernatant were taken and transferred to vials containing (10 μl) of 0.2% ascorbic acid to stabilize [6]-shogaol and its metabolites. The metabolites were extracted from media by addition of equal volume of acetonitrile and centrifugation, in which the supernatant was harvested. The samples were then diluted 5-fold in acetonitrile and were analyzed by HPLC ECD.

Growth Inhibition of Human Cancer Cells.

Cell growth inhibition was determined by a 3-(4,5-dimethylthiazol-2-yl)-2,5-diphenyltetrazolium bromide (MTT) colorimetric assay (Mosmann T (1983) J Immunol Methods 65:55-63.). Human colon cancer (HCT-116) and human lung cancer (H-1299) cells (3000 cells/well) were plated in 96-well microtiter plates and were allowed to attach for 24 h at 37° C. The test compounds (in DMSO) were added to cell culture medium to desired final concentrations (0-80 µM) final DMSO concentrations for control and treatments were 0.1%). After the cells were cultured for 24 h, the medium was aspirated, and the cells were treated with (200 µl) of fresh medium containing 2.41 mM MTT. After incubation for 3 h at 37° C., the medium containing MTT was aspirated, 100 µl of DMSO was added to solubilize the formazan precipitate, and the plates were shaken gently for an hour at room temperature.

Absorbance values were derived from the plate reading at 550 nm on a microtiter plate reader. The reading reflected the number of viable cells and was expressed as a percentage of viable cells in the control. Both HCT-116 and H-1299 cells were cultured in McCoy's 5A medium. All of the above media were supplemented with 10% fetal bovine serum, 1% penicillin/streptomycin, and 1% glutamine, and the cells were kept in a 37° C. incubator with 95% humidity and 5% $CO_2$.

Terminal Deoxynucleotidyl Transferase Deoxyuridine Triphosphate Nick-End Labeling Assay.

HCT-116 and H-1299 cells were seeded in six-well plates at $1.0 \times 10^5$ cells/well and were incubated at 37° C. in a 5% $CO_2$ incubator. After 24 h, fresh media supplemented with DMSO (control), [6]-shogaol (10 or 20 µM), M9 (40 or 80 µM), or M11 (40 or 80 µM) were added to the wells. After 24-h incubation, cells were washed and pretreated for 15 min at room temperature with a solution of 20 µg/ml proteinase K. Cells were then washed twice with PBS pH 7.4 and were fixed for 10 min at room temperature using 10% neutral formaldehyde solution. After two washes in distilled $H_2O$, cells were resuspended in 100 µl of distilled $H_2O$ and were applied on silanized microscope slides. Slides were incubated overnight at 37° C. and were washed twice with PBS. Terminal deoxynucleotidyl transferase deoxyuridine triphosphate nick-end labeling (TUNEL) assay was then performed according to the manufacturer's protocol. Cells were observed under 400× power using a Zeiss A1 microscope (Carl Zeiss, Inc., Thornwood, N.Y.).

Ten fields per slide were evaluated, and TUNEL-positive cells (with brown coloration in the nucleus) were expressed as a percentage of the total number of cells contained in a field. Statistical Analysis. For simple comparisons between two groups, twotailed Student's t test was used. A p value of less than 0.05 was considered statistically significant in all the tests.

Experimental Part 2

General Procedure A for Michael Addition Reaction

A catalyst amount of $NaHCO_3$ (0.05 eq) was added to a mixture of [6]-shogaol (1.0 eq) and amino acid (3.0 eq) in methanol/water (1:1, v/v). The mixture was stirred at room temperature (rt) for 3-48 h, adjusted pH until 6 with a diluted HOAc solution (0.1 M), and extracted with n-butanol (BuOH) (5 mL×3). Combined organic layers were concentrated under reduced pressure at 20° C. The residue was subjected to column chromatography (CC) on Sephadex LH-20, and eluted with 90% ethanol in water, producing the desired thiol conjugates M2, M5, or M13.

General Procedure B for the Synthesis of Ketone Reduced Metabolites using $NaBH_4$.

$NaBH_4$ (2.5-4.0 eq) was added to a solution of M2, M5 or [6]-shogaol (1.0 eq) in methanol at 0° C. After stirring at 0° C. for 2 h, the reaction media was neutralized with a diluted HOAc solution (0.1 M) and extracted with n-BuOH (5 mL×3). Combined organic layers were concentrated under reduced pressure. The residue was purified by CC on Sephadex LH-20 or preparative TLC to produce the required compounds M1, M4, or M9.

Synthesis of 5-Cysteinyl-[6]-Shogaol (M2)

General procedure A was followed using [6]-shogaol (200 mg, 0.72 mmol), L-cysteine (263 mg, 2.17 mmol), and $NaHCO_3$ (3 mg, 0.036 mmol) in methanol/water (10 mL, 1:1, v/v). The mixture was stirred at rt for 24 h. The final residue was purified by CC on Sephadex LH-20 with 90% ethanol in water to give the title compound M2 as a white solid (170 mg, yield 60%). M2 (a mixture of diastereomers): $^1H$ NMR (600 MHz, $CD_3OD$) δ 6.77 (1H, d, J=1.5 Hz, H-2'), 6.67 (1H, d, J=8.0 Hz, H-5'), 6.61 (1H, dd, J=8.0, 1.5 Hz, H-6'), 2.77 (2H, m, H-1), 2.74 (2H, m, H-2), 2.71 (1H, m, H-4a), 2.63 (1H, m, H-4b), 3.12 (1H, m, Hminor-5) and 3.08 (1H, m, Hmajor-5), 1.53 (2H, m, H-6), 1.39 (2H, m, H7), 1.28 (2H, m, H-8), 1.33 (2H, m, H-9), 0.89 (3H, t, J=7.0 Hz, H-10), 3.82 (3H, s, OMe-3'), 3.62 (1H, dd, J=9.3, 3.7 Hz, HCys-α, major) and 3.59 (1H, dd, J=9.3, 3.7 Hz, HCys-α, minor), 3.18 (1H, dd, J=14.5, 3.7 Hz, HCys-βa), and 2.84 (1H, dd, J=14.5, 9.3 Hz, HCys-βb); 13C NMR (150 MHz, CD3OD) δ 133.8 (s, C-1'), 113.1 (d, C-2'), 148.9 (s, C-3'), 145.8 (s, C-4'), 116.2 (d, C-5'), 121.7 (d, C-6'), 30.3 (t, C-1), 47.5 (t, C-2), 211.8 (s, C=O, C-3), 49.6 (t, C-4), 42.3 (2d, C-5), 36.8 (2t, C-6), 27.4 (2t, C-7), 32.6 (2t, C-8), 23.6 (t, C-9), 14.4 (2q, C-10), 56.4 (q, OMe-3'), 56.3 (d, CCys-α), 32.8 (2t, CCys-β), and 172.5 (s, Cys α-COOH); positive APCIMS: m/z 398 [M+H]$^+$.

Synthesis of 5-cysteinyl-M6 (M1)

General procedure B was followed using M2 (74 mg, 0.19 mmol) and $NaBH_4$ (28 mg, 0.75 mmol) in methanol (3 mL). The resulting solution was extracted with n-BuOH (5 mL×3). Combined organic layers were evaporated under reduced pressure at 20° C. The final residue was purified by CC on Sephadex LH-20 with 90% ethanol in water to give the title compound M1 as a white solid (68 mg, yield 90%); M1 (a mixture of diastereomers): $^1H$ NMR (600 MHz, $CD_3OD$) δ 6.77 (1H, d, J=1.7 Hz, H-2'), 6.69 (1H, d, J=8.0 Hz, H-5'), 6.62 (1H, dd, J=8.0, 1.7 Hz, H-6'), 2.68 (1H, m, H-1a), 2.58 (1H, m, H-1b), 1.72 (2H, m, H-2), 3.90 (1H, m, Hminor-3) and 3.66 (1H, m, Hmajor-3), 1.71 (2H, m, H-4), 2.94 (1H, m, H-5), 1.66 (1H, m, H-6a), 1.52 (1H, m, H-6b), 1.44 (2H, m, H-7), 1.28 (2H, m, H-8), 1.33 (2H, m, H-9), 0.89 (3H, t, J=7.0 Hz, H-10), 3.82 (3H, s, OMe-3'), 3.64 (1H, m, HCys-α), 3.15 (1H, m, HCys-βa), and 2.85 (1H, m, HCys-βb); 13C NMR (150 MHz, CD3OD) δ 135.1 (s, C-1'), 113.2 (d, C-2'), 148.8 (s, C-3'), 145.5 (s, C-4'), 116.1 (d, C-5'), 121.8 (d, C-6'), 32.5 (2t, C-1), 41.1 (2t, C-2), 69.3 (2d, C-3), 43.9 (t, C-4), 43.8 (2d, C-5), 35.0 (2t, C-6), 27.1 (2t, C-7), 33.0 (t, C-8), 23.6 (t, C-9), 14.4 (q, C-10), 56.4 (q, OMe-3'), 55.8 (2d, CCys-α), 32.8 (4t, CCys-β), and 172.8 (s, Cys α-COOH); positive APCIMS: m/z 400 [M+H]$^+$.

Synthesis of 5-N-acetylcysteinyl-[6]-shogaol (M5)

General procedure A was followed using [6]-shogaol (200 mg, 0.72 mmol), N-acetyl-L-cysteine (354 mg, 2.17 mmol), and NaHCO$_3$ (3 mg, 0.036 mmol) in methanol/water (10 mL, 1:1, v/v). The mixture was stirred at rt for 72 h. The final residue was purified by CC on Sephadex LH-20 with 90% ethanol in water to give title compound M5 as a white solid (252 mg, yield 80%); M5 (a mixture of diastereomers): $^1$H NMR (600 MHz, CD$_3$OD) 6.77 (1H, d, J=1.7 Hz, H-2'), δ 6.67 (1H, d, J=8.0 Hz, H-5'), 6.61 (1H, dd, J=8.0, 1.7 Hz, H-6'), 2.78 (2H, m, H-1), 2.77 (2H, m, H-2), 2.70 (1H, dd, J=16.8, 8.1 Hz, H-4a), 2.64 (1H, dd, J=16.8, 6.3 Hz, H-4b), 3.10 (1H, m, H-5), 1.48 (2H, m, H-6), 1.38 (2H, m, H-7), 1.25 (2H, m, H-8), 1.28 (2H, m, H-9), 0.89 (3H, t, J=7.0 Hz, H-10), 3.82 (3H, s, OMe-3'), 4.58 (1H, dd, J=8.1, 4.8 Hz, HCys-α, major) and 4.53 (1H, dd, J=8.1, 4.8 Hz, HCys-α, minor), 3.02 (1H, dd, J=13.6, 4.8 Hz, HCys-βa, minor) and 2.96 (1H, dd, J=13.6, 4.8 Hz, HCys-βa, major), 2.89 (1H, dd, J=13.6, 7.2 Hz, HCys-βb, major) and 2.76 (1H, dd, J=13.6, 7.2 Hz, HCys-βb, minor), and 2.01 (3H, s, CH3CO, major) and 1.98 (3H, s, CH3CO, minor); positive APCIMS: m/z 440 [M+H]$^+$.

Synthesis of 5-N-acetylcysteinyl-M6 (M4)

General procedure B was followed using M5 (151 mg, 0.34 mmol) and NaBH$_4$ (53 mg, 1.38 mmol) in methanol (10 mL). The resulting solution was extracted with n-BuOH (10 mL×3). Combined organic layers were evaporated under reduced pressure at 20° C. The final residue was purified by CC on Sephadex LH-20 with 90% ethanol in water to give the title compound M4 as a white solid (100 mg, yield 66%); M4 (a mixture of diastereomers): $^1$H NMR (600 MHz, CD$_3$OD) δ 6.77 (1H, brs, H-2'), 6.68 (1H, d, J=8.0 Hz, H-5'), 6.62 (1H, dd, J=8.0 Hz, H-6'), 2.67 (1H, m, H-1a), 2.58 (1H, m, H-1 b), 1.72 (2H, m, H-2), 3.88 (1H, m, Hminor-3) and 3.70 (1H, m, Hmajor-3), 1.68 (2H, m, H-4), 2.83 (1H, m, H-5), 1.60 (1H, m, H-6a), 1.44 (1H, m, H-6b), 1.45 (2H, m, H-7), 1.28 (2H, m, H-8), 1.33 (2H, m, H9), 0.89 (3H, t, J=7.0 Hz, H-10), 3.83 (3H, s, OMe-3'), 4.54 (1H, m, HCys-α), 3.00 (1H, m, HCys-βa), 2.80 (1H, m, HCys-βb), and 1.98 (3H, s, CH3CO); 13C NMR (150 MHz, CD3OD) δ 135.1 (2s, C-1'), 113.2 (d, C-2'), 148.8 (s, C-3'), 145.5 (s, C-4'), 116.1 (d, C-5'), 121.8 (d, C-6'), 32.5 (t, C-1), 41.0 (2t, C-2), 69.3 (4d, C-3), 44.3 (4t, C-4), 43.8 (2d, C-5), 35.2 (t, C-6), 27.2 (4t, C-7), 32.9 (t, C-8), 23.6 (t, C-9), 14.4 (2q, C-10), 56.4 (q, OMe-3'), 54.2 (2d, CCys-α), 32.7 (2t, CCys-β), 173.2 (s, Cys α-COOH), 174.0 (s, CH3CO), and 22.4 (q, CH3CO); positive APCIMS: m/z 442 [M+H]$^+$.

Synthesis of 1-(4'-hydroxy-3'-methoxyphenyl)-4-decen-3-ol (M6)

A solution of [6]-shogaol (138 mg, 0.5 mmol) in methanol (10 mL) was cooled to −78° C., CeCl$_3$.7H$_2$O (745 mg, 2.0 mmol) was added and the mixture was stirred at −78° C. for 10 min. Then, NaBH4 (48 mg, 1.25 mmol) was added to the mixture and allowed to react at −78° C. for 30 min. The reaction was quenched by saturated aqueous NH$_4$Cl solution (20 mL) and extracted with ethyl acetate (20 mL×3). The organic phases were separated, pooled, washed with water (10 mL×2) and brine (10 mL×1), dried over Na$_2$SO$_4$, and evaporated in vacuo. The residue was subjected to preparative TLC (hexane/EtOAc=3:1) to produce the title compound M6 as a colorless oil (139 mg, yield 100%); $^1$H NMR (600 MHz, CDCl$_3$) δ 6.70 (1H, d, J=1.7 Hz, H-2'), 6.82 (1H, d, J=8.0 Hz, H-5'), 6.68 (1H, dd, J=8.0, 1.7 Hz, H-6'), 2.62 (2H, m, H-1), 1.85 (1H, m, H-2a), 1.78 (1H, m, H-2b), 4.07 (1H, m, H-3), 5.49 (1H, dd, J=15.3, 6.7 Hz, H-4), 5.65 (1H, dt, J=15.3, 6.7 Hz, H-5), 2.03 (2H, m, H-6), 1.38 (2H, m, H-7), 1.32-1.25 (4H, m, H-8 and H-9), 0.89 (3H, t, J=6.9 Hz, H-10), and 3.87 (3H, s, OMe-3'); positive APCIMS: m/z 279 [M+H]$^+$.

Synthesis of 5-methoxy-1-(4'-hydroxy-3'-methoxyphenyl)-decan-3-one (M7)

A solution of [6]-shogaol (100 mg, 0.36 mmol) in methanol (5 mL) at 0° C. was treated with a solution of sodium (21 mg, 0.91 mmol) in methanol (1 mL). After 4.0 h, glacial acetic acid (0.5 mL) was added, and the solution was concentrated under reduced pressure. The residue was dissolved in water (5 mL), and extracted with ethyl acetate (5 mL×3). The organic phases were pooled, washed with water (5 mL×2) and brine (5 mL×1), dried over Na$_2$SO$_4$, and evaporated in vacuo. The residue was subjected to preparative TLC (hexane/EtOAc=4:1) to give the title compound M7 as a yellow oil (100 mg, yield 90%); $^1$H NMR (600 MHz, CDCl$_3$) δ 6.69 (1H, d, J=1.6 Hz, H-2'), 6.82 (1H, d, J=8.1 Hz, H-5'), 6.66 (1H, dd, J=8.1, 1.6 Hz, H-6'), 2.75 (2H, m, H-1), 2.83 (2H, t, J=7.5 Hz, H-2), 2.64 (1H, dd, J=15.7, 7.6 Hz, H-4a), 2.40 (1H, dd, J=15.7, 4.7 Hz, H-4b), 3.66 (1H, m, H-5), 1.48 (1H, m, H-6a), 1.42 (1H, m, H-6b), 1.31-1.25 (6H, m, ranged from H-7 to H-9), 0.88 (3H, t, J=7.1 Hz, H-10), and 3.87 (3H, s, OMe-3'); positive APCIMS, m/z 309 [M+H]$^+$.

Synthesis of 5-methylthio-1-(4'-hydroxy-3'-methoxyphenyl)-decan-3-one (M10)

A solution of NaSCH$_3$ in water (15% w/w, 1.5 mL, 3.19 mmol) was added to a solution of [6]-shogaol (100 mg, 0.36 mmol) in THF (10 mL) at rt in portions. After stirring for 6.0 h, 10 mL of water was added, followed by extraction with ethyl acetate (10 mL×3). The organic phases were separated, pooled, washed with water (10 mL×2) and brine (10 mL×1), dried over Na$_2$SO$_4$, and evaporated in vacuo. The residue was loaded to preparative HPLC (methanol in water: 70%-100% in 50 min) to give the title compound M10 as a yellow oil (70 mg, yield 60%); $^1$H NMR (600 MHz, CDCl$_3$) δ 6.69 (1H, d, J=1.6 Hz, H-2'), 6.82 (1H, d, J=8.0 Hz, H-5'), 6.67 (1H, dd, J=8.0, 1.6 Hz, H-6'), 2.73 (2H, m, H-1), 2.84 (2H, t, J=7.6 Hz, H-2), 2.67 (1H, dd, J=16.6, 7.5 Hz, H-4a), 2.57 (1H, dd, J=16.6, 6.4 Hz, H-4b), 3.02 (1H, m, H-5), 1.49 (2H, m, H-6), 1.42 (1H, m, H-7a), 1.36 (1H, m, H-7b), 1.32-1.24 (4H, m, H-8 and H-9), 0.88 (3H, t, J=6.9 Hz, H-10), 3.87 (3H, s, OMe-3'), and 2.03 (3H, s, SCH3-5); positive APCIMS: m/z 325 [M+H]$^+$.

Synthesis of 1-(4'-hydroxy-3'-methoxyphenyl)-decan-3-one (M11)

A solution of [6]-shogaol (276 mg, 1.0 mmol) in THF (2 mL) at rt was treated with 10% Pd/C (30 mg, 10% w/w) under H$_2$. The mixture was stirred at rt overnight and filtered. The filtrate was concentrated under reduced pressure. The residue was loaded to preparative TLC (hexane/EtOAc=8:1) to give the title compound M11 as a yellow oil (272 mg, yield 98%); $^1$H NMR (600 MHz, CDCl$_3$) δ 6.69 (1H, d, J=1.6 Hz, H-2'), 6.82 (1H, d, J=8.0 Hz, H-5'), 6.66

(1H, dd, J=8.0, 1.7 Hz, H-6'), 2.69 (2H, t, J=7.4 Hz, H-1), 2.82 (2H, t, J=7.4 Hz, H-2), 2.37 (1H, t, J=7.4 Hz, H-4), 1.54 (2H, m, H-5), 1.30-1.24 (8H, m, ranged from H-6 to H-9), 0.87 (3H, t, J=6.8 Hz, H-10), and 3.87 (3H, s, OMe-3'); positive APCIMS, m/z 279 [M+H]$^+$.

Synthesis of 1-(3',4'-dihydroxyphenyl)-decan-3-one (M8)

A solution of BBr$_3$ in dichloromethane (DCM) (1.0 M, 0.67 mL, 0.67 mmol) was added dropwise to a solution of M11 (74 mg, 0.27 mmol) in DCM (3 mL) at −78° C. The reaction was allowed to warm up to rt for 2.0 h, quenched with water (10 mL), and extracted with ethyl acetate (10 mL×3). The organic phases were separated, pooled, washed with water (10 mL×2) and brine (10 mL×1), dried over Na$_2$SO$_4$, and evaporated in vacuo. The residue was subjected to preparative TLC (DCM/Methanol=20:1) to give the title compound M8 as a red solid (50 mg, yield 70%); $^1$H NMR (600 MHz, CDCl$_3$) δ 6.70 (1H, d, J=1.9 Hz, H-2'), 6.76 (1H, d, J=8.0 Hz, H-5'), 6.59 (1H, dd, J=8.0, 1.9 Hz, H-6'), 2.69 (2H, t, J=7.4 Hz, H-1), 2.78 (2H, t, J=7.4 Hz, H-2), 2.37 (2H, t, J=7.4 Hz, H-4), 1.54 (2H, m, H-5), 1.30-1.24 (8H, m, ranged from H-6 to H-9), and 0.87 (3H, t, J=6.8 Hz, H-10); positive APCIMS: m/z 265 [M+H]$^+$.

Synthesis of 1-(4'-hydroxy-3'-methoxyphenyl)-decan-3-ol (M9)

General procedure B was followed using M11 (100 mg, 0.36 mmol) and NaBH$_4$ (34 mg, 0.90 mmol) in methanol (2 mL). The resulting solution was extracted with ethyl acetate (5 mL×3). Combined organic layers were concentrated under reduced pressure. The final residue was purified by preparative TLC (DCM/Methanol=40:1) to produce the title compound M9 as a white solid (90 mg, yield 90%); $^1$H NMR (600 MHz, CDCl$_3$) δ 6.71 (1H, d, J=1.6 Hz, H-2'), 6.83 (1H, d, J=8.0 Hz, H-5'), 6.69 (1H, dd, J=8.0, 1.6 Hz, H-6'), 2.72 (1H, m, H-1a), 2.60 (1H, m, H-1 b), 1.76 (1H, m, H-2a), 1.71 (1H, m, H-2b), 3.62 (1H, m, H-3), 1.48 (2H, m, H-4), 1.44 (2H, m, H-5), 1.32-1.26 (8H, m, ranged from H-6 to H-9), 0.88 (3H, t, J=6.8 Hz, H-10), and 3.88 (3H, s, OMe-3'); positive APCIMS: m/z 281 [M+H]$^+$.

Synthesis of 5-methylthio-1-(4'-Hydroxy-3'-methoxyphenyl)-decan-3-ol (M12)

General procedure B was followed using M10 (39 mg, 0.12 mmol) and NaBH$_4$ (11 mg, 0.30 mmol) in methanol (3 mL). The resulting solution was extracted with ethyl acetate (5 mL×3). The combined organic layers were concentrated under reduced pressure. The final residue was purified by preparative TLC (DCM/Methanol=50:1) to produce the title compound M12 as a yellow oil (39 mg, yield 100%); Mixture of diastereomers: $^1$H NMR (600 MHz, CDCl$_3$) δ 6.71 (1H, d, J=1.5 Hz, H-2'), 6.82 (1H, d, J=8.0 Hz, H-5'), 6.68 (1H, dd, J=8.0, 1.5 Hz, H-6'), 2.74 (1H, m, H-1a), 2.61 (1H, m, H-1 b), 1.75 (2H, m, H-2), 3.98 (1H, m, Hminor-3) and 3.80 (1H, m, Hmajor-3), 1.70 (1H, m, H-4a), 1.65 (1H, m, H-4b), 2.75 (1H, m, H-5), 1.61 (2H, m, H-6), 1.44 (2H, m, H-7), 1.32-1.23 (4H, m, H-8 and H-9), 0.88 (3H, t, J=7.0 Hz, H-10), 3.86 (3H, s, OMe-3'), and 2.02 (3H, s, SMe-5); positive APCIMS, m/z 327 [M+H]$^+$.

Synthesis of 5-glutathiol[6]-shociaol (M13)

General procedure A was followed using [6]-shogaol (100 mg, 0.36 mmol), reduced L-glutathione (333 mg, 1.09 mmol), and NaHCO$_3$ (1.5 mg, 0.018 mmol) in methanol/water (8 mL, 1:1, v/v). The mixture was stirred at rt for 3 h. The final residue was purified by CC on Sephadex with 90% ethanol in water to give the title compound M13 as a white solid (168 mg, yield 80%); M13 (a mixture of diastereomers): $^1$H NMR (600 MHz, CD$_3$OD) δ 6.77 (1H, d, J=1.6 Hz, H-2'), 6.68 (1H, d, J=8.0 Hz, H-5'), 6.61 (1H, dd, J=8.0, 1.6 Hz, H-6'), 2.78-2.75 (4H, m, H-1 and H-2), 2.74-2.61 (2H, m, H-4), 3.10 (1H, m, H-5), 1.51-1.45 (2H, m, H-6), 1.42-1.33 (2H, m, H-7), 1.25 (2H, m, H-8), 1.28 (2H, m, H-9), 0.88 (3H, t, J=7.3 Hz, H-10), 3.82 (3H, s, OMe-3'), 3.65 (1H, m, HGlu-α), 2.13 (2H, m, HGlu-β), 2.55 (1H, m, HGlu-γa), 2.51 (1H, m, HGlu-γb), 4.50 (1H, dd, J=8.5, 5.1 Hz, HCys-α), 3.05-2.95 (1H, m, HCys-βa), 2.84-2.80 (1H, m, HCys-βb), and 3.80 (2H, brs, HGly-α); 13C NMR (150 MHz, CD3OD) δ 133.9 (s, C-1'), 113.2 (d, C-2'), 148.9 (s, C-3'), 145.7 (s, C-4'), 116.2 (d, C-5'), 121.8 (d, C-6'), 30.4 (t, C-1), 46.0 (2t, C-2), 211.2 (s, C=O, C-3), 49.8 (2t, C-4), 42.2 (2d, C-5), 36.2 (2t, C-6), 27.5 (2t, C-7), 32.8 (t, C-8), 23.6 (t, C-9), 14.4 (q, C-10), 56.4 (q, OMe-3'), 55.4 (d, CGlu-α), 27.8 (t, CGlu-β), 33.0 (t, CGlu-γ), 174.0 (s, Glu α-COOH), 175.2 (s, Glu γ-CON), 55.0 (2d, CCys-α), 33.3 (2t, CCys-β), 172.9 (s, Cys α-CON), 45.0 (t, CGly-α), and 175.2 (s, Gly α-COOH); positive APCIMS: m/z 584 [M+H]$^+$.

Separation of the M13 Isomers Using Preparative HPLC.

Waters preparative HPLC systems with 2545 binary gradient module, Waters 2767 sample manager, Waters 2487 autopurification flow cell, Waters fraction collector III, dual injector module, and 2489 UV/Visible detector, were used to separate M13 isomers. A Phenomenex Gemini-NX C18 column (250 mm×30.0 mm i.d., 5 μm) was used with a flow rate of 20.0 mL/min. The wavelength of UV detector was set at 280 nm. The injection volume was 1.0 mL for each run. The mobile phase consisted of solvent A (H$_2$O+0.1% formic acid) and solvent B (MeOH+0.1% formic acid).

M13 (5 mg/mL) was injected to the preparative column and eluted with a gradient solvent system (0% B from 0 to 5 min; 0 to 50% B from 5 to 15 min; 50 to 60% B from 15 to 25 min; 60 to 80% B from 25 to 45 min; then 0% B from 45 to 50 min). The fractions were checked by a HPLC-APCI-MS system and then combined. A total of 7 runs resulted in 10 mg of M13-1 ($t_R$ 16.5 min) and 22 mg of M13-2 ($t_R$ 16.8 min).

M13-1: white solid; 1H NMR (700 MHz, CD3OD) δ 6.77 (1H, d, J=1.8 Hz, H-2'), 6.69 (1H, d, J=8.1 Hz, H-5'), 6.61 (1H, dd, J=8.1, 1.8 Hz, H-6'), 2.78 (2H, m, H-1), 2.77 (2H, m, H-2), 2.76 (1H, dd, J=17.1, 7.2 Hz, H-4a), 2.65 (1H, dd, J=17.1, 6.4 Hz, H-4b), 3.10 (1H, m, H-5), 1.49 (2H, m, H-6), 1.42 (1H, m, H-7a), 1.31 (1H, m, H-7b), 1.25 (2H, m, H-8), 1.28 (2H, m, H-9), 0.88 (3H, t, J=7.1 Hz, H-10), 3.82 (3H, s, OMe-3'), 3.62 (1H, t, J=6.0 Hz, HGlu-α), 2.13 (2H, m, HGlu-β), 2.55 (1H, m, HGlu-γa), 2.50 (1H, m, HGlu-γb), 4.49 (1H, dd, J=8.7, 5.0 Hz, HCys-α), 3.00 (1H, dd, J=13.7, 5.0 Hz, HCys-βa), 2.73 (1H, dd, J=13.7, 8.7 Hz, HCys-βb), and 3.74 (2H, AB, J=17.2 Hz, HGly-α); 13C NMR (175 MHz, CD3OD) δ 134.0 (s, C-1'), 113.2 (d, C-2'), 148.9 (s, C-3'), 145.7 (s, C-4'), 116.2 (d, C-5'), 121.8 (d, C-6'), 30.4 (t, C-1), 46.1 (t, C-2), 211.3 (s, C=O, C-3), 49.9 (t, C-4), 42.0 (d, C-5), 36.2 (t, C-6), 27.6 (t, C-7), 32.8 (t, C-8), 23.6 (t, C-9), 14.4 (q, C-10), 56.4 (q, OMe-3'), 55.6 (d, CGlu-α), 27.9 (t, CGlu-β), 33.1 (t, CGlu-γ), 174.3 (s, Glu α-COOH), 175.2 (s, Glu γ-CON), 55.0 (d, CCys-α), 33.2 (t, CCys-β), 172.4 (s, Cys α-CON), 44.5 (t, CGly-α), and 175.9 (s, Gly α-COOH); positive APCIMS: m/z 584 [M+H]$^+$.

M13-2: white solid; $^1$H NMR (700 MHz, CD$_3$OD) δ 6.77 (1H, d, J=1.8 Hz, H-2'), 6.69 (1H, d, J=8.1 Hz, H-5'), 6.61

(1H, dd, J=8.1, 1.8 Hz, H-6'), 2.77 (2H, m, H-1), 2.76 (2H, m, H-2), 2.70 (1H, dd, J=17.1, 7.2 Hz, H-4a), 2.64 (1H, dd, J=17.1, 6.4 Hz, H-4b), 3.10 (1H, m, H-5), 1.48 (2H, m, H-6), 1.38 (2H, m, H-7), 1.25 (2H, m, H-8), 1.28 (2H, m, H-9), 0.88 (3H, t, J=7.1 Hz, H-10), 3.82 (3H, s, OMe-3'), 3.64 (1H, t, J=6.0 Hz, HGlu-α), 2.14 (2H, m, HGlu-β), 2.56 (1H, m, HGlu-γa), 2.50 (1H, m, HGlu-γb), 4.49 (1H, dd, J=8.7, 5.0 Hz, HCys-α), 2.97 (1H, dd, J=13.7, 5.0 Hz, HCys-βa), 2.81 (1H, dd, J=13.7, 8.7 Hz, HCys-βb), and 3.74 (2H, AB, J=17.2 Hz, HGly-α); 13C NMR (175 MHz, CD3OD) δ 133.9 (s, C-1'), 113.2 (d, C-2'), 148.8 (s, C-3'), 145.7 (s, C-4'), 116.2 (d, C-5'), 121.8 (d, C-6'), 30.4 (t, C-1), 46.0 (t, C-2), 211.3 (s, C=O, C-3), 49.6 (t, C-4), 42.4 (d, C-5), 36.3 (t, C-6), 27.5 (t, C-7), 32.8 (t, C-8), 23.6 (t, C-9), 14.4 (q, C-10), 56.4 (q, OMe-3'), 55.5 (d, CGlu-α), 27.9 (t, CGlu-β), 33.1 (t, CGlu-γ), 174.3 (s, Glu α-COOH), 175.3 (s, Glu γ-CON), 55.1 (d, CCys-α), 33.3 (t, CCys-β), 172.4 (s, Cys α-CON), 44.3 (t, CGly-α), and 175.9 (s, Gly α-COOH); positive APCIMS: m/z 584 [M+H]+.

Growth inhibition of human cancer and normal cells. Cell growth inhibition was determined by a MTT colorimetric assay. Human colon cancer cells HCT-116, human lung cancer cells H-1299, human colon fibroblast cells CCD-18Co, and human lung fibroblast cells IMR-90 were plated in 96-well microtiter plates with 3000 cells/well and allowed to attach for 24 h at 37° C. The test compounds (in DMSO) were added to cell culture medium to the desired final concentrations (final DMSO concentrations for control and treatments were 0.1%). After the cells were cultured for 48 h, the medium was aspirated and cells were treated with 200 μL fresh medium containing 2.41 mmol/L MTT. After incubation for 3 h at 37° C., the medium containing MTT was aspirated, 100 μL of DMSO was added to solubilize the formazan precipitate, and plates were shaken gently for an hour at room temperature. Absorbance values were derived from the plate reading at 550 nm on a Biotek microtiter plate reader (Winooski, Vt.). The reading reflected the number of viable cells and was expressed as a percentage of viable cells in the control. Both HCT-116 and H-1299 cells were cultured in McCoy's 5A medium. CCD-18Co and IMR-90 cells were cultured in Eagle's modified essential medium (EMEM). All of the above media were supplemented with 10% fetal bovine serum, 1% penicillin/streptomycin, and 1% glutamine, and the cells were kept in a 37° C. incubator with 95% humidity and 5% $CO_2$.

TUNEL (Terminal Deoxynucleotidyl Transferase dUTP Nick End labeling) assay.

HCT-116 and H1299 cells were seeded in 6-well plates at $1 \times 10^5$ cells/well and incubated at 37° C. in 5% $CO_2$ incubator. After 24 hours, fresh media supplemented with DMSO (control), [6]-shogaol, M2, M6, or M13 metabolites (20 μM or 40 μM) were added to the wells. After 6 or 24 hours incubation at 37° C. in 5% $CO_2$ incubator, cells were washed and pre-treated for 15 min at room temperature with a solution of 20 μg/ml proteinase K. Cells were then washed twice with phosphate buffer saline pH 7.4 (PBS) and fixed for 10 min at room temperature using 10% neutral formaldehyde solution. After 2 washes in $ddH_2O$, cells were resuspended in 100 μL $ddH_2O$ and applied on silanized microscope slides. Slides were incubated overnight at 37° C., and washed twice with PBS. TUNEL assay was then carried out according to the manufacturer's protocol. Cells were observed under 400× power using a Zeiss microscope A1 (Thornwood, N.Y.). 10 fields per slide were evaluated, and TUNEL+ cells (with brown coloration in the nucleus) were expressed as a percentage of the total number of cells contained in a field.

Statistical Analysis.

For simple comparisons between two groups, two-tailed Student's test was used. A p-value of less than 0.05 was considered statistically significant in all the tests.

Experimental Part 3

Incubation with Liver Microsomes

Experiment 1

Human liver microsomes (HLM) (either 0.1 mg/mL or 0.5 mg/mL final concentration) were incubated with [6]-shogaol (50 μM) for several time points. The experimental incubation mixture consisted of 100 mM potassium phosphate buffer, a prepared NADPH-regenerating system, and human liver microsomes. In all experiments, [6]-shogaol was dissolved in dimethylsulfoxide (DMSO) with a final concentration not exceeding 1% (v/v). After 5 min preincubation in a 37° C. water bath, the reaction was initiated by the addition of [6]-shogaol and was further incubated at 37° C. The reaction was terminated at 0, 30, 45, and 60 minutes by the addition of ice-cold acetonitrile (equal volume) containing 2% acetic acid. The mixture was vortexed and underwent centrifugation at 13,000 g for 10 minutes. Aliquots of supernatant were stored at −20° C. until analysis. Control incubations without NADPH-regenerating system, without substrate, or without microsomes were performed to ensure that metabolite formation was microsome- and NADPH-dependent.

Experiment 2

Based upon the optimized conditions in experiment 1, mouse liver microsomes (MLM), rat liver microsomes (RLM), dog liver microsomes (DLM), monkey liver microsomes (CyLM) and human liver microsomes (HLM) (each 0.5 mg/mL, respectively), were mixed with aforementioned incubation mixture and were held in 37° C. water bath for 5 minutes before the reactions were initiated by the addition of [6]-shogaol (50 μM). Reactions were terminated after 30 minutes incubation in a 37° C. water bath by the addition of ice-cold acetonitrile (equal volume) containing 2% acetic acid. The mixture was vortexed and underwent centrifugation at 13,000 g for 10 minutes. Aliquots of supernatant were stored at −20° C. until analysis.

Chemical Inhibition Studies:

Inhibitors ABT (500 μM) and 18β-GA (500 μM) or DMSO controls were pre-incubated with microsomes in experimental incubation mixture at 37° C. for 20 minutes before initiating the reaction by the addition of [6]-shogaol (50 μM). Reactions were terminated 30 minutes after substrate addition and incubation in a 37° C. water bath by equal volume of ice-cold acetonitrile with 2% acetic acid. The mixture was vortexed and underwent centrifugation at 13,000 g for 10 minutes. Aliquots of supernatant were stored at −20° C. until analysis.

Sample Preparation for LC/MS Analysis:

To elucidate the structures of the two previously uncharacterized metabolites of [6]-shogaol, samples from monkey liver microsomes (CyLM) incubations were enriched by partitioning with EtOAc. Briefly, a large-scale reaction (1.0 mL) of CyLM incubated with [6]-shogaol was performed in which enzyme concentration was 0.5 mg/mL and [6]-shogaol concentration was 50 μM. All other reagent relative concentrations were kept constant. After 30 minutes incubation in a 37° C. water bath, samples were treated in an identical fashion as described above to stabilize metabolites and precipitate proteins from solution. The supernatant was then extracted three times with ice-cold EtOAc (5× volumes each time). The pooled supernatant was dried under reduced pressure at 30° C., and the residue was resuspended in MeOH with 0.2% acetic acid for LC/MS analysis.

Synthesis of (1E, 4E)-1-(4'-hydroxy-3'-methoxyphenyl)-deca-1,4-dien-3-one (M14)

[6]-Shogaol (276 mg, 1.0 mmol) was dissolved in tetrahydrofuran (THF) and cooled down to 0° C. To this mixture, a solution of DDQ (181 mg, 0.8 mmol) in THF was added. The mixture was stirred at 0° C. for 30 minutes and then warmed to room temperature (RT) for 3 hours. Then water was added and the resulting mixture was extracted with EtOAc (×3). The organic phase was washed with water (×1) and brine (×1), dried over anhydrous $NaSO_4$, and filtered. The filtration was evaporated and the residue was purified by chromatography column (CC) (hexane/ethyl acetate=8:1 and 6:1) to give the desired compound as a yellow oil (170 mg, yield: 62%); $^1H$ NMR (600 MHz, $CDCl_3$) δ 7.59 (1H, d, J=15.9 Hz, H-1), 6.82 (1H, d, J=15.9 Hz, H-2), 6.44 (1H, d, J=15.6 Hz, H-4), 6.99 (1H, dt, J=15.6, 7.0 Hz, H-5), 2.27 (2H, q, J=7.0 Hz, H-6), 1.51 (2H, m, H-7), 1.34-1.29 (4H, m, H-8 and H-9), 0.90 (3H, t, J=6.8 Hz, H-10), 7.07 (1H, d, J=1.4 Hz, H-2'), 6.93 (1H, d, J=8.2 Hz, H-5'), 7.14 (1H, dd, J=8.2, 1.4 Hz, H-6'), and 3.93 (3H, s, OMe-3'); $^{13}C$ NMR (150 MHz, $CDCl_3$) δ 143.3 (d, C-1), 123.3 (d, C-2), 189.3 (s, C-3, 0=0), 129.1 (d, C-4), 148.0 (d, C-5), 32.7 (t, C-6), 27.9 (t, C-7), 31.4 (t, C-8), 22.4 (t, C-9), 14.0 (q, C-10), 127.4 (s, C-1'), 109.7 (d, C-2'), 148.1 (s, C-3'), 146.8 (s, C-4'), 114.8 (d, C-5'), 122.9 (d, C-6'), and 56.0 (q, OMe-3'); positive ESI-MS, m/z 275 $[M+H]^+$.

Synthesis of (E)-1-(4'-hydroxy-3'-methoxyphenyl)-dec-1-en-3-one (M15)

The general procedure disclosed herein was followed by using M11 (45 mg, 0.16 mmol), prepared previously as disclosed, and DDQ (29 mg, 0.13 mmol) in THF (6 mL). The mixture was stirred at RT for 2 hours. The resulting residue was purified by preparative TLC (hexane/ethyl acetate=5:1) to give the desired compound as a yellow oil (34 mg, yield: 77%); $^1H$ NMR (600 MHz, $CDCl_3$) δ 7.47 (1H, d, J=16.1 Hz, H-1), 6.59 (1H, d, J=16.1 Hz, H-2), 2.63 (2H, t, J=7.5 Hz, H-4), 1.66 (2H, m, H-5), 1.33-1.25 (8H, m, ranged from H-6 to H-9), 0.87 (3H, t, J=6.7 Hz, H-10), 7.08 (1H, d, J=1.6 Hz, H-2'), 6.91 (1H, d, J=8.2 Hz, H-5'), 7.09 (1H, dd, J=8.2, 1.6 Hz, H-6'), and 3.92 (3H, s, OMe-3'); $^{13}C$ NMR (150 MHz, $CDCl_3$) δ 142.6 (d, C-1), 124.2 (d, C-2), 200.8 (s, C-3, C=O), 40.7 (t, C-4), 24.6 (t, C-5), 29.3 (t, C-6), 29.1 (t, C-7), 31.7 (t, C-8), 22.6 (t, C-9), 14.1 (q, C-10), 127.1 (s, C-1'), 109.4 (d, C-2'), 148.1 (s, C-3'), 146.8 (s, C-4'), 114.8 (d, C-5'), 123.4 (d, C-6'), and 56.0 (q, OMe-3'); positive ESI-MS, m/z 277 $[M+H]^+$.

HPLC Analysis:

The mobile phases consisted of solvent A (30 mM sodium phosphate buffer containing 1.75% acetonitrile and 0.125% tetrahydrofuran, pH 3.35) and solvent B (15 mM sodium phosphate buffer containing 58.5% acetonitrile and 12.5% tetrahydrofuran, pH 3.45). The gradient elution had the following profile: 20-62% B from 0 to 13 min; 62% B from 13 to 39 min; 62-100% B from 39 to 48 min; 100% B from 48 to 53 min; and 20% B from 53.1 to 58 min. The cells were then cleaned at a potential of 1000 mV for 1 minute. The injection volume of the sample was 10 μL. The eluent was monitored by the Coulochem electrode array system (CEAS) with potential settings at 0, 200, 250, 300, 350, 400 and 500 mV.

LC/MS Analysis:

LC/MS analysis was carried out with a Thermo-Finnigan Spectra System, which consisted of an Accela high-speed MS pump, an Accela refrigerated autosampler, and an LTQ Velos ion trap mass detector (Thermo Electron, San Jose, Calif., USA) incorporated with heated electrospray ionization (H-ESI) interfaces. A Gemini C18 column (50×2.0 mm i.d., 3 μm; Phenomenex, Torrance, Calif., USA) was used for separation at a flow rate of 0.2 mL/min. The column was eluted with 100% solvent A (5% aqueous methanol with 0.2% acetic acid) for 3 minutes, followed by linear increases in B (95% aqueous methanol with 0.2% acetic acid) to 40% from 3 to 15 minutes, to 85% from 15 to 45 minutes, to 100% from 45 to 50 minutes, and then with 100% B from 50 to 55 minutes. The column was then re-equilibrated with 100% A for 5 minutes. The LC eluent was introduced into the H-ESI interface. The positive ion polarity mode was set for the H-ESI source with the voltage on the H-ESI interface maintained at approximately 4.5 kV. Nitrogen gas was used as the sheath gas and auxiliary gas. Optimized source parameters, including ESI capillary temperature (300° C.), capillary voltage (50 V), ion spray voltage (3.6 kV), sheath gas flow rate (30 units), auxiliary gas flow rate (5 units), and tube lens (120 V), were tuned using authentic [6]-shogaol. The collision-induced dissociation (CID) was conducted with an isolation width of 2 Da and normalized collision energy of 35 for $MS^2$ and $MS^3$. Default automated gain control target ion values were used for MS-$MS^3$ analyses. The mass range was measured from 50 to 1000 m/z. Data acquisition was performed with Xcalibur 2.0 version (Thermo Electron, San Jose, Calif., USA).

Kinetic Study:

To estimate kinetic parameters of metabolism of [6]-shogoal to major product M6 in liver microsomes from human and other species, the incubation conditions were optimized to ensure that formation rate of M6 was in the linear range in relation to incubation time and protein concentration. [6]-Shogaol (7.81, 15.63, 31.25, 62.5, 125, 250, 500, 1000, and 2000 μM) was incubated with liver microsomes from mouse (MLM), rat (RLM), dog (DLM), monkey (CyLM), and human (HLM) (0.1 mg/mL each, respectively) for 30 minutes. All incubations were performed in triplicate. The apparent $K_m$ and $V_{max}$ values were calculated from analysis of experimental data according to the Michaelis-Menten equation, and the results were graphically represented (for HLM) by an Eadie-Hofstee plot. Kinetic constants were reported as the value+/−S.E. of the parameter estimate.

Growth Inhibitory Effects of M14 and M15 Against Human Colon and Lung Cancer Cells:

Cell growth inhibition was determined by a MTT colorimetric assay. Human colon cancer cells HCT-116 and human lung cancer cells H-1299 were plated in 96-well microtiter plates with 3000 cells/well and allowed to attach for 24 hours at 37° C. The test compounds (in DMSO) were added to cell culture medium to the desired final concentrations (final DMSO concentrations for control and treatments were 0.1%). After the cells were cultured for 24 hours, the medium was aspirated and cells were treated with 200 μL fresh medium containing 2.41 mmol/L MTT. After incubation for 3 hours at 37° C., the medium containing MTT was aspirated, 100 μL of DMSO was added to solubilize the formazan precipitate, and plates were shaken gently for an hour at room temperature. Absorbance values were derived from the plate reading at 550 nm on a Biotek microtiter plate reader (Winooski, Vt.). The reading reflected the number of viable cells and was expressed as a percentage of viable cells in the control. Both HCT-116 and H-1299 cells were cultured in McCoy's 5A medium. All of the above media were supplemented with 10% fetal bovine serum, 1% penicillin/streptomycin, and 1% glutamine, and the cells were kept in a 37° C. incubator with 95% humidity and 5% $CO_2$.

Measurement of Induction of Apoptosis in Human Cancer Cells by M14, M15, and [6]-Shogaol:

Human colon cancer cells HCT-116 and human lung cancer cells H-1299 were plated in 96-well plates at a density of 5000 cells/well and allowed to attach overnight at 37° C. M14, M15, or [6]-shogaol in DMSO, or DMSO control, diluted in media, were added to cells and incubated for an additional 24 hours at 37° C. After 24 hours, media containing compound was removed and cells were lysed in their respective wells with reagents from a Cell Death Detection ELISA$^{PLUS}$ kit from Roche Applied Science (Mannheim, Germany). Samples were harvested after cell lysates were spun down at 300 g for 10 minutes. To streptavidin coated microplates, 20 µL samples were added, and mixed with 80 µL Immunoreagent, which consisted of anti-histone-biotin, and anti-DNA-POD, and incubated with gentle shaking for 2 hours at room temperature. After incubation, Immunoreagent was removed and samples were washed 3 times with 250 µL incubation buffer. Substrate solution, ABTS, was added to each well and color was developed for 15 minutes before stopping the reaction with ABTS stop solution and reading absorbance on a microplate reader at 430 nm. Experiments were performed in triplicate and the average is given in comparison to DMSO control with standard deviation.

Experimental Part 4

A549 Culture and Reagents

A549 cells were cultured in FK12 media (Corning, Corning, N.Y.) supplemented with 10% Fetal Bovine Serum and 1% penicillin/streptomycin (Gemini Bio-Products, West Sacramento, Calif.). Protease and phosphatase inhibitor mix was from Thermo Scientific (Waltham, Mass.). Antibodies for Western blotting were from Cell Signaling (Danvers, Mass.). Protein concentrations were determined from cell lysates using a Pierce BCA kit (Thermo Fisher Scientific, Rockford, Ill.). BrdU (5-bromo-2-deoxyuridine) was from Sigma-Aldrich (St Louis, Mo.). Apoptag plus Peroxydase In Situ Apoptosis Detection Kit was from Millipore (Billerica, Mass.), and the BrdU Immunohistochemistry Kit was from Chemicon International (Temecula, Calif.).

Metabolism of 6S and M2 in A549 and IMR90 Cells

A549 or IMR90 cells ($1.0 \times 10^6$) were plated in 6-well culture plates and allowed to attach for 24 hours at 37° C. in 5% $CO_2$ incubator. 6S or M2 (in DMSO) was then added to culture media to reach a final concentration of 10 or 20 µM, respectively. At different time points (0, 30 minutes, 1, 2, 4, 8, and 24 hours), 190 µL samples of supernatant were taken and transferred to vials containing 10 µL of 0.2% acetic acid to stabilize 6S, M2, and their respective metabolites. To extract compounds from the culture media, an equal volume of acetonitrile was added to the supernatant samples and these mixtures were centrifuged. The supernatant was harvested and the samples were analyzed by HPLC-ECD.

Determination of Cell Viability

A549 cell viability was determined by a 3-(4,5-dimethylthiazol-2-yl)-2,5-diphenyltetrazolium bromide (MTT) colorimetric assay. A549 cells (6000 cells/well) were plated in 96-well microtiter plates and allowed to attach for 24 hours at 37° C. and 5% $CO_2$. 6S or M2 (in DMSO) were added to cell culture medium to desired final concentrations (0-80 µM; final DMSO concentrations for control and treatments were 0.1%). After the cells were cultured for 24 hours, the medium was aspirated and the cells were treated with 2.41 mM MTT in fresh media. After incubation for 3 hours at 37° C., the medium containing MTT was removed, 100 µL of DMSO was added to the wells, and the plates were shaken gently for an hour at room temperature. Absorbance values were derived from the plate reading at 550 nm on a Biotek Synergy 2 plate reader (Winooski, Vt.). The experiment was repeated independently to confirm the results.

Determination of Apoptosis

The Cell Death Detection ELISA (Enzyme-linked immunoabsorbant assay) Plus kit from Roche (Mannheim, Germany) was used. A549 cells (10000 cells/well) were plated in 96-well microtiter plates and allowed to attach for 24 hours at 37° C. and 5% $CO_2$. 6S or M2 (in DMSO) was added to cell culture medium to desired final concentrations (10 and 20 µM; final DMSO concentrations for control and treatments were 0.1%). After 24 hours, the microplate was centrifuged for 10 minutes at 1200 rpm, and the supernatant was removed. 200 µl of the lysis buffer was added in each well and incubated for 30 minutes at room temperature. The plate was then centrifuged for 10 minutes at 1200 rpm and 20 µl of the supernatant was transferred to streptavidin-coated micro-wells. ELISA assay was performed according to manufacturer's instruction. Absorbance in each well was measured at 405 nm in absorbance units (AU), and the enrichment factor (EF) in small nucleosomes was calculated with the formula EF=AU treated/AU DMSO. The experiment was repeated independently to confirm the results.

Intracellular Glutathione (GSH) Measurement

The total GSH content was measured using a HT Glutathione Assay kit (Trevigen, Galthersburg, Md.). Briefly A549 cells were plated in 60×15 mm culture plates and were allowed to attach overnight at 37° C. Cells were treated with 10 µM M2 and incubated for 0, 2, 4, 8, or 24 hours. Cells were harvested and proteins were precipitated with 5% (w/v) metaphosphoric acid. Samples were then processed following the manufacturer's instructions. The measurement of the absorbance of 5-thio-2-nitrobenzoic acid (TNB) at 405 nm was used to quantify glutathione levels in each sample, which was then compared to the standard curve and corrected for protein concentration. The experiment was repeated independently to confirm the results.

For measurement of oxidized glutathione (Glutathione Disulfide or GSSG), samples and GSSG standards were treated with 2M 4-vinylpyridine (1 µL/50 µL sample) at room temperature for one hour. 4-Vinylpyridine (Sigma Aldrich, St. Louis, Mo.) blocks free thiols present in the reaction, consequentially blocking the formation of new GSSG by GSH. The 2M solution was freshly prepared by diluting 4-vinylpyridine in ethanol in a ratio of approximately 1:3.6. After incubation, samples were processed using the Trevigen kit's protocol and absorbance was measured at 405 nm as described herein.

The quantity of reduced cellular glutathione (or GSH) is obtained by subtracting the oxidized samples values from the total glutathione values or: $GSH_{(reduced)} = GSH_{(total)} - GSSG_{(oxidized)}$. Ratios of reduced to oxidized glutathione are shown to further represent cellular redox status after treatment with 6S or M2. The experiment was repeated independently to confirm the results.

Western Blotting

Cell extracts were prepared by incubating cells for 5 minutes on ice with RIPA (Radio-Immunoprecipitation Assay) buffer (Thermo Fisher Scientific, Rockford, Ill.) supplemented with a protease and phosphatase inhibitor mix. Cell lysate was then centrifuged at 13,000 rpm at 4° C. for 20 minutes, and supernatant was harvested for Western blot analysis. Briefly, 30-60 µg of protein extract were separated on a 10-16% polyacrylamide gel and transferred on PVDF (polyvinylidene difluoride) membrane (Biorad, Hercules, Calif.). Membrane was blocked using a 1% casein solution in TBS-Tween 20. Primary rabbit antibodies were diluted in blocking solution and incubated with the membrane overnight at 4° C. After washing the membrane with 3 changes of TBS-T, secondary Horse Radish Peroxydase (HRP)-conjugated anti-rabbit antibody was diluted 1:3000 in blocking solution and incubated with PVDF membrane for 1 hour at room temperature. Signal was then revealed using FEMTO chemoluminescent substrate (Thermo Scientific, Waltham, Mass.) and by exposing the membrane to photosensitive photographic films for various times. Films were developed using a SRX-101A Konica Minolta developer (Tokyo, Japan). The experiment was repeated independently twice to confirm the results. Fold-induction of proteins calculated by normalizing the band of interest to the loading control (β-actin), and this adjusted intensity what compared to the control (DMSO) sample.

GSH Rescue Assay

A549 cells were plated on 60 mm culture dishes, at $0.5\times10^6$ density. After 24 hours, DMSO, 6S or M2 (10, 20, 40, 80, 120 µM) were added to the cells and incubated with or without the addition of 5 mM GSH in the culture media. After 24 hours, toxicity was assessed using the MTT assay and using the method described above. The experiment was repeated independently to confirm the results.

Animal Experiments

Nu/J nude mice were obtained from Jackson Laboratories (Bar Harbor, Me.). Animals were randomized into 4 groups. A549 cells ($5\times10^6$ cells) were implanted in both flanks of 8-weeks old Nu/J mice. One week after implantation, animals were given 100 µl of the following treatments through oral gavage 5 times/week: DMSO 0.25 ml/kg (control; n=4); 6S 10 mg/kg (n=4); 6S 30 mg/kg (n=4) or M2 30 mg/kg (n=5). Compounds were diluted in a solution of 5% DMSO in corn oil. Animal body weight and tumor volume were recorded for the duration of the experiment. Tumor volume was calculated by measuring the length and width of the tumors using a digital caliper and using the formula (Length×Width$^2$)/2. One hour before sacrifice, mice were given one last treatment dose as well as one intra-peritoneal injection of BrdU (7.5 mg/kg in 100 µl PBS). After 7 weeks, tumor tissues were harvested and weighed. A portion of the tumors was snap frozen in liquid nitrogen and another portion was placed in a histology cassette and immersed in formalin solution.

Immunohistochemistry

Paraffin-fixed tissues were sent to Precision Histology Lab (Oklahoma City, Okla.) for embedding in paraffin blocks. Then paraffin blocks were processed into 3-4 µm sections that were then put on microscope slides. Sections were then deparaffinized by using a succession of 3 baths of xylene (5 minutes each), 2 baths of absolute ethanol (5 minutes each), 95% ethanol for 3 minutes, 70% ethanol for 3 minutes, and rinsed in PBS. Immunostaining with TUNEL (terminal deoxynucleotidyl transferase dUTP nick end labeling) and BrdU staining kits was performed following manufacturer's recommendation. For staining quantification, sequential high-power field pictures of tumors were taken (10 pictures per tumor) using an A1 Zeiss microscope (Oberkochen, Germany). Images were processed using the Image J software, which was used to count positive, brown-colored cells in each field. Average number per tumor was calculated by averaging the number obtained for each field, and the average number of positive cells per group was obtained by averaging the values of each tumor belonging to the experimental group.

Statistical Analysis

Statistics were calculated using either a two-tailed Student t-test, or ANOVA followed by Bonferroni's post-test. Results were considered significant when $p<0.05$.

Experimental Part 5

Chemical Synthesis of M2' and M2"

The experimental procedure to synthesize M2' and M2" was similar to that of M2, as described herein. In brief, a catalyst amount of $NaHCO_3$ (1.3 mg, 0.015 mmol) was added to a mixture of 8S (91.2 mg, 0.3 mmol) and cysteine (54 mg, 0.45 mmol) in methanol/water (6 mL, 1:1, v/v). The mixture was stirred at room temperature for 24 hours, adjusted to pH 6 with a diluted acetic acid solution (0.1 M). The mixture was then purified by preparative HPLC to give a white solid M2' (70 mg, yield 55%). In the preparation of M2", 10S (100 mg, 0.3 mmol) was used in place of 8S in the above reaction: M2" (73 mg, yield 54%).

Purification of M2' or M2" Using Preparative HPLC

Waters preparative HPLC systems with 2545 binary gradient module, Waters 2767 sample manager, Waters 2487 auto-purification flow cell, Waters fraction collector III, dual injector module, and 2489 UV/Visible detector, were used to separate M2' or M2" from the reaction mixture. A Phenomenex Gemini-NX $C_{18}$ column (250 mm×30.0 mm i.d., 5 µm) was used with a flow rate of 20.0 mL/min. The wavelength of UV detector was set at 280 nm. The injection volume was 1.0 mL for each run. The mobile phase consisted of solvent A ($H_2O+0.1\%$ formic acid) and solvent B (MeOH+0.1% formic acid). Reaction mixture of M2' was injected to the preparative column and eluted with a gradient solvent system (75 to 87% B from 0 to 12 min; to 75% B from 12 to 12.5 min; then with 75% B from 12.5 to 15 min). A total of 6 runs resulted in 70 mg of M2' ($t_R$ 9.45 min). Similarly, the reaction mixture of M2" was injected to the preparative column and eluted with a gradient solvent system (85 to 100% B from 0 to 15 min; then with 100% B from 15 to 16 min; to 85% B from 16 to 16.5 min; then with 85% B from 16.5 to 20 min). A total of 7 runs resulted in 73 mg of M2" ($t_R$ 8.13 min).

Metabolism of 8S, 10S, M2' and M2" in Human Colon Cancer Cells

Cells ($1.0\times10^6$) were plated in six-well culture plates and were allowed to attach for 24 hours at 37° C. in 5% $CO_2$ incubator. 8S or 10S in DMSO, or the corresponding cysteine-conjugated metabolites M2' and M2" were diluted in McCoy's 5A medium (containing 10% fetal bovine serum, 1% penicillin/streptomycin, and 1% glutamine) to reach a final concentration of 10 µM and were incubated with different colon cancer cell lines (HCT-116 or HT-29). At different time points (0, 2, 4, 8, 24, and 48 hours), 190 µL samples of supernatant were taken and transferred to vials containing 10 µL of 2% acetic acid to stabilize these compounds and their respective metabolites. An equal volume of acetonitrile was added to the samples before centrifugation. The supernatant was harvested and the samples were then analyzed by HPLC-ECD.

Evaluation of Toxicity in Human Colon Cancer and Normal Colon Cells

Cell viability was determined by an MTT colorimetric assay. Briefly, human colon fibroblast cells CCD-18Co or human colon cancer cells HCT-116 or HT-29, were plated in 96-well microtiter plates with 3000 cells/well and allowed to attach for 24 hours at 37° C. and 5% $CO_2$. The test compounds (in DMSO) were added to cell culture medium to desired final concentrations (final DMSO concentrations for control and treatments were 0.1%). After the cells were cultured for 24 hours, the medium was aspirated and cells were treated with 200 µL fresh medium containing 2.41 mmol/L MTT. After incubation for 3 hours at 37° C., the medium containing MTT was aspirated, 100 µL of DMSO was added to solubilize the formazan precipitate, and the plates were shaken gently for an hour at room temperature. Absorbance values were derived from the plate reading at 550 nm on a Biotek (Winooski, Vt.) microtiter plate reader. The reading reflected the number of viable cells and was expressed as a percentage of viable cells in the control. CCD-18Co cells were grown in EMEM. Both HCT-116 and HT-29 cells were cultured in McCoy's 5A medium. All of the above media were supplemented with 10% fetal bovine serum, 1% penicillin/streptomycin, and 1% glutamine, and the cells were kept in a 37° C. incubator with 95% humidity and 5% $CO_2$.

Apoptosis Analysis

Apoptosis was determined by FACS analysis of propidium iodide (PI)-stained cells. In brief, cells were trypsinized, washed with cold phosphate-buffered saline (PBS), fixed in ice-cold 70% ethanol for 1 hour, and then resuspended in 2 mL PBS supplemented with 10 µL RNase (100 mg/ml) and incubated at 37° C. for 30 min. After incubation, DNA was stained with 1 mg/mL PI in PBS. Cell staining was analyzed using a Cell Lab Quanta™ SC flow cytometer (Beckman Coulter, Danvers, Mass.) and data were processed using FCS Express software (DeNovo Software, Los Angeles, Calif.). The percentage of apoptotic cells in each sample was determined based on the sub $G_0$ peaks detected in monoparametric histograms.

Measurement of Reactive Oxygen Species

The assay employed the cell-permeable fluorogenic probe 2',7'-dichlorodihydrofluorescin diacetate [DCFH-DA] (Sigma Aldrich, St. Louis, Mo.) to measure the relative changes in $O^-_2$ and $H_2O_2$ levels in HCT-116 or HT-29 cells after treatment with 5, 10, and 20 µM 6S or M2 (or DMSO) over 0, 2, 4, 8, and 24 hours. In brief, DCFH-DA is diffused into cells and is deacetylated by cellular esterases to non-fluorescent 2',7'-dichlorodihydrofluorescin (DCFH), which is rapidly oxidized to highly fluorescent 2',7'-dichlorodihydrofluorescein (DCF) by intracellular hydrogen peroxide, or other low molecular weight peroxides. Measured fluorescence intensity is thus proportional to the amount of such peroxides in the cell at a given time. Human colon cancer cells HCT-116 or HT-29 were seeded in 96-well black-sided, clear-bottomed culture plates, with 5000 cells/well and were allowed to adhere for 24 hours in a 37° C. incubator with 5% $CO_2$. Media was aspirated and 5, 10, or 20 µM M2, 6S, or DMSO diluted in media were added to designated wells, which were run in triplicate. After desired incubation times of 0, 2, 4, 8, or 24 hours, media and test compounds were aspirated. Cells were washed three times with 200 µL PBS before addition of 100 µL 1 mM DCF-DA. The fluorogenic probe permeated cell membranes and was processed to DCF for one hour at 37° C. After incubation, plates were immediately placed in a Biotek microplate reader to measure fluorescence at wavelengths of 485 (excitation) and 528 (emission). Raw values were normalized to DMSO control for each time point and are presented as fold induction versus 0 hour time point (n=3).

Western Blot Analysis

Cell lysates were prepared in ice-cold RIPA lysis buffer [25 mM Tris-HCl (pH 7.6), 150 mM NaCl, 1% NP-40, 1% sodium deoxycholate, 0.1% SDS, Thermo Fisher Scientific] supplemented with a protease inhibitor cocktail (AEBSF, aprotinin, bestatin, E-64, leupeptin and pepstatin A in DMSO with EDTA, Thermo Fisher Scientific). Protein content was measured by a Pierce BCA Assay Kit (Thermo Fisher Scientific). Protein contents of cell lysates (30 µg protein/lane) were resolved by SDS-PAGE. Proteins were then electro-transferred onto PVDF membranes and blots were blocked for one hour at room temperature in 1×TBS with 1% Casein (Bio-Rad Laboratories, Berkeley, Calif.). Blots were then incubated overnight at 4° C. with the desired primary antibody diluted in TBS with 0.5% Tween-20. Blots were then washed with TBS-Tween 20 and probed for 1 hour with the appropriate secondary antibody (1:1000). Protein bands were visualized with chemiluminescence using West Femto maximum detection substrate (Thermo Fisher Scientific). To confirm equal protein loading in each lane, immunoblots were stripped and re-probed for β-actin. Protein fold-induction was calculated by normalizing the intensity of the band of interest to β-actin first, and then to DMSO control lanes.

Colony Formation Assay

Human colon cancer cells HCT-116 or HT-29 (1,000 cells per well) were seeded in 6-well culture plates for 24 hours and then incubated with M2 (0, 1, 5, 10, 20, or 40 µM) in DMSO in a 37° C. incubator with 5% CO2. After 2 weeks, colonies were washed with phosphate-buffered saline (PBS), then stained with a mixture of 6.0% glutaradehyde and 0.5% crystal violet for 30 min at room temperature, rinsed in water, air-dried and then photographed.

Statistical Analysis

Student's t-test or two-way analysis of variance (ANOVA) with the Bonferroni post-test were used to determine the statistical significance of data, which was performed on GraphPad Prism version 5.00 for Windows (GraphPad Software, San Diego, Calif.).

Results

Metabolism of [6]-Shogaol in Mice.

In the study, HPLCECD and LC/ESI-MS were used to analyze the major metabolites of [6]-shogaol in the collected samples. Compared with the samples collected from control mice, 12 major metabolites (M1-M12) were observed in fecal samples collected from [6]-shogaol-treated mice. These metabolites were numbered according to their chromatographic retention times. Incubation of the fecal sample extracts with glucuronidase and sulfatase did not change the peak areas of all the metabolites, suggesting these compounds do not exist in glucuronidated and/or sulfated forms, whereas in urinary and plasma samples, most of the metabolites were not detectable without incubation with glucuronidase and sulfatase. These results suggest that the metabolites in the urine and plasma were in the glucuronidated and/or sulfated forms. After hydrolysis, the plasma samples and urine samples showed similar metabolic profiles to those of fecal samples, as confirmed by LC/MS analysis. Seven major metabolites (M6-M12) were purified from fecal samples collected from mice treated with 200 mg/kg [6]-shogaol using oral gavage. Their structures were elucidated on the basis of analysis of their $^1H$, $^{13}C$, and $^2D$ NMR spectra. For the metabolites not purified from mouse fecal samples (M1-M5), structures were determined using LC/ESI tandem mass spectrometry (MS/MS) by analyzing the MS' (n=1-3) spectra as well as by comparison with authentic standards. Among all the metabolites, M1 through M5, M10, and M12 are the thiol conjugates of [6]-shogaol and its metabolite M6.

Structure Elucidation of Non-Thiol-Conjugated Metabolites (M6 Through M9 and M11).

Metabolite M6.

M6 had the molecular formula $C_{17}H_{26}O_3$ according to ESI-MS at m/z 261 [M+H–H$_2$O] and its $^1$H and $^{13}$C NMR data. The molecular weight of M6 was 2 mass units higher than that of [6]-shogaol. In addition to the distinguishable resonance for a methoxyl group (δH 3.84, 3H, s), the $^1$H NMR spectrum of M6 (Table 1) also indicated the presence of a 1,3,4-tri-substituted phenyl group [δH 6.77 (1H, br s); 6.70 (1H, br d, J=7.8 Hz); and 6.63 (I H, br d, J=7.8 Hz)], and a double bond [δH 5.47 (1H, dd, J=15.4, 7.1 Hz) and 5.64 (I H, dt, J=15.4, 7.1 Hz)], and a methyl group (δH 0.92, 3 H, t, J=7.2 Hz). Its $^{13}$C NMR spectrum displayed 17 carbon resonances, which were classified by heteronuclear single quantum correlation experiments as two methyls, six methylenes, six methines, and three quaternary carbons. The aforementioned NMR data implied the structure of M6 was closely related to that of [6]-shogaol. The only difference was that C-3 of M6 was assigned as an oxymethine (δH 3.99, 1 H, m; δC 71.6) instead of the expected ketone carbonyl in [6]-shogaol (δC 201.5). This was confirmed by the heteronuclear multiple-bond correlations (HMBC) of H-3/C-1, H-3/C-2, H-4/C-3, and H-5/C-3. Therefore, the structure of M6 was determined as shown in FIG. 1.

Metabolite M7.

M7 showed the molecular formula $C_{18}H_{28}O_4$ on the basis of ESI-MS at m/z 291 [M+H–H$_2$O] and its $^1$H and $^{13}$C NMR data. The molecular weight of M7 was 32 mass units higher than that of [6]-shogaol. Compared with [6]-shogaol, the NMR spectra of M7 gave the appearance of an oxygenated methine (δH 3.67, 1 H, m; δC 77.1) a methylene (δH 2.66, dd, J=16.2, 7.8 Hz; 2.42, dd, J=16.2, 4.8 Hz), and a methoxyl (δH 3.30, 3 H, s; δC 56.9) groups instead of the expected double bond at C-4 and C-5 of [6]-shogaol, which indicated that the α,β-unsaturated keto-structure of [6]-shogaol was reduced to a saturated ketone. This was further confirmed by the observation of the HMBCs δH 2.66 and 2.42 (the methylene group) and C-2 (δC 45.8), C-3 (δC 209.0), and C-6 (δC 33.8), indicating that the methylene group was located at position C-4. The oxygenated methine was located at C-5 by the observation of the HMBCs between H-4 and δC 77.1. The HMBC between δH 3.30 (the methoxyl group) and C-5 (δC 77.1) suggested that the methoxyl group was directly linked with C-5. Thus, M7 was identified as shown in FIG. 1.

Metabolite M8.

M8 showed the molecular formula $C_{16}H_{24}O_3$ on the basis of ESI-MS at m/z 265 [M+H]$^+$ and its $^1$H and $^{13}$C NMR data. Compared with [6]-shogaol, the NMR spectra of M8 showed the disappearance of the double bond at C-4 and C-5, as well as the methoxyl group at C-3" (Table 1), which indicated M8 was 3",4"-dihydroxyphenyl-decan-3-one (FIG. 1).

Metabolite M9.

M9 was obtained as a white amorphous powder. M9 was shown to have the molecular formula $C_{17}H_{28}O_3$ on the basis of ESI-MS at m/z 263 [M+H–H$_2$O] and its $^1$H and $^{13}$C NMR data. The molecular weight of M9 was 2 mass units higher than that of M6, indicating that M9 was the double-bond-reduced product of M6. This was further confirmed by the observation of the appearance of two methene groups (δH 1.48, 2 H and δC 37.6 and δH 1.30, 2 H and δC 29.4) and the disappearance of the double-bond signals in M9 (Table 1). Therefore, the structure of M9 was determined as 1-(4"-hydroxy-3"-methoxyphenyl)-decan-3-ol (FIG. 1).

Metabolite M11.

M11 was obtained as a white amorphous powder. It showed a protonated molecular ion at m/z 279 [M+H]$^+$, which was 2 mass units higher than that of [6]-shogaol. The $^1$H and $^{13}$C NMR data of M11 were very similar to those of [6]-shogaol, and the major difference was that M11 had two methene groups (δH 2.38, 2 H; δH 1.56, 2 H) (Table 1) instead of the double bond in [6]-shogaol, clearly indicating that M11 was the double-bond-reduced metabolite of [6]-shogaol. This was further confirmed by the key correlations observed in the HMBC spectrum. Therefore, M11 was identified as 1-(4"-hydroxy-3"-methoxyphenyl)-decan-3-one, also known as [6]-paradol, which is one of the components reportedly found in ginger.

Structure Elucidation of Thiol-Conjugated Metabolites (M1-M5, M10, and M12).

Metabolite M5.

The mass spectrum of metabolite M5 exhibited [M+H]$^+$ ions at m/z 440 in the positive mode, which was 163 mass units higher than that of [6]-shogaol, indicating that M5 was the N-acetylcysteine conjugated [6]-shogaol (molecular weight of N-acetylcysteine is m/z 163). The MS2 spectrum of M5 showed a major product ion at m/z 277. The MS3 spectrum of this product ion had the same fragment ions as those of the authentic [6]-shogaol, indicating that M5 was an N-acetylcysteine conjugate of [6]-shogaol. To further elucidate the structure of M5, it was synthesized by reacting N-acetylcysteine with 6-shogaol. The structure of the synthesized N-acetylcysteine conjugate (5-N-acetylcysteinyl-[6]-shogaol) was determined using its $^1$H, $^{13}$C, and 2D NMR data. The $^1$H and $^{13}$C NMR spectra showed very similar patterns to those of [6]-shogaol (Table 2). Compared with the $^1$H NMR spectrum of [6]-shogaol, the major differences were the appearance of a methine (δH 2.74, m, 2H) and a methylene (δH 3.14, m, 1H) group in 5-N-acetylcysteinyl-[6]-shogaol in lieu of the expected double bond of [6]-shogaol, as well as four additional proton signals for a N-acetylcysteine group (δH 3.00 dd and 2.92 dd, H-1"; δH 4.58 dd, H-2"; and δH 2.01 s, H-5"). The major differences between the $^{13}$C spectra of 5-N-acetylcysteinyl-[6]-shogaol and [6]-shogaol were the presence of carbons observed at δC 46.1 (C-4) and 42.6 (C-5) instead of the double bond of [6]-shogaol, as well as the presence of five additional carbons at δC 30.4 (C-1"), 54.6 (C-2"), 173.1 (C-3" and C-4"), and 22.6 (C-5") for a N-acetylcysteine group (Table 2). The HMBC spectrum of 5-N-acetylcysteinyl-[6]-shogaol had cross-peaks between H-1"(δH 3.00 and 2.92) and C-5 (δC 42.6), indicating that N-acetylcysteine was conjugated at C-5 of [6]-shogaol. All of these spectral features supported the structure of 5-N-acetylcysteinyl-[6]-shogaol. M5 had almost the same retention time as well as the same molecular mass and fragment ion mass spectra as those of the synthetic 5-Nacetylcysteinyl-[6]-shogaol. Therefore, M5 was identified as 5-Nacetylcysteinyl-[6]-shogaol.

Metabolite M2.

M2 had a molecular weight of 397 as determined by the mass ion at m/z 398 [M+H]$^+$, which was 121 mass units higher than that of [6]-shogaol and 42 mass units lower than that of M5, indicating that M2 was the cysteine conjugated metabolite of [6]-shogaol. The major product ion of M2 showed a fragment ion at m/z 277 and the tandem mass of this product ion was almost identical to the tandem mass of authentic [6]-shogaol. All of these spectral features were consistent with M2 as 5-cysteinyl-[6]-shogaol.

Metabolites M1, M3, and M4.

M1 exhibited [M+H]$^+$ ions at m/z 400 in the ESI-positive mode, which was 2 mass units higher than that of M2 and 121 mass units higher than that of M6, indicating that M1 was the cysteine conjugated metabolite of M6. This was confirmed by the observation of m/z 261 [M-121-H$_2$O+H]$^+$ as one of the major product ions in the MS2 spectrum of M1. The tandem mass spectrum of this product ion (MS3: 261/400) was almost identical to the MS2 spectrum of authentic M6. Thus, M1 was identified as 5-cysteinyl-M6.

M4 showed [M+H]$^+$ ions at m/z 442 in the positive mode, which was 42 mass units higher than that of M1, 163 mass units higher than that of M6, and 2 mass units higher than that of M5, suggesting that M4 was the N-acetylcysteine conjugated metabolite of M6. Its MS2 spectrum also had product ion m/z 261 [M-121-H$_2$O+H]$^+$, and the tandem mass spectrum of this product ion (MS3: 261/442) was almost identical to the MS2 spectrum of authentic M6. All of these spectral features were consistent with M4 as 5-N-acetylcysteinyl-M6.

M3 had a molecular weight of 456 on the basis of the observation of the [M+H]$^+$ ions at m/z 457 in the positive mode, which was 178 mass units higher than that of M6 and 57 mass units higher than that of M1. This corresponded with the predicted molecular weight of the cysteinylglycine-conjugated metabolite of M6. Similar to that of M1 and M4, the MS3 spectrum of the product ion m/z 261 of M3 was almost identical to the MS2 spectrum of authentic M6. Thus, M3 was identified as the cysteinylglycine conjugate of M6 (FIG. 1).

Metabolite M10.

M10 had the molecular formula $C_{18}H_{28}O_3S$ on the basis of ESI-MS at m/z 325 [M+H]$^+$ and its $^1H$ and $^{13}C$ NMR data, which was 48 mass units higher than that of [6]-shogaol. Compared with the NMR spectra of [6]-shogaol, the NMR spectra of M10 showed signals for a methine (δH 3.04, m, 1H; δC 41.6), a methane (δH 2.59, dd and 2.69 dd, 2H; δC 48.5), and a methyl (δH 2.04, 3 H, s; δC 13.3) group group (Table 2) instead of the expected double bond of [6]-shogaol. The chemical shifts of the methine and methane groups were similar to those of positions 4 and 5 of M5, and the chemical shift of the methyl group was similar to that reported for the methylthiol group. In addition, a cross-peak in the HMBC spectrum was observed between δH 2.04 (the methyl group) and δC 41.6 (the methane group). Thus, M10 was identified as the methylthiol-conjugated [6]-shogaol.

Metabolite M12.

The positive ion ESI-MS of M12 displayed a molecular ion peak at m/z 327 [M+H]$^+$, supporting a molecular formula of $C_{18}H_{30}O_3S$. The molecular weight of M12 was 2 mass units higher than that of M10, which was similar to the difference between M6 and [6]-shogaol. Compared with the NMR spectra of M10, M12 showed the signal of an oxygenated methine (δH 4.00, 1H, m; δC 68.9) in lieu of the expected ketone group of M10, which indicated the ketone group at C-3 of M10 was reduced to a hydroxyl group of M12, which was further confirmed by the HMBCs of OH-3/C-3 and OH-3l/C-4. Therefore, M12 was identified as the methylthiol-conjugated M6 (FIG. 1).

Metabolism of [6]-Shogaol in Cancer Cells.

After incubation of [6]-shogaol with four different cancer cell lines (HCT-116, HT-29, H-1299, and CL-13), the culture media were collected at different time points and analyzed by HPLC-ECD. The results indicate that [6]-shogaol was extensively metabolized in all four cancer cell lines. After 24-h incubation, four major metabolites appeared in HCT-116 human colon cancer cells. Three of them were identified as M6, M9, and M11 by comparing their retention times and tandem mass fragments with those of purified authentic standards. The fourth metabolite (M13) was a newly revealed compound at the retention time of 14.50 min. The mass spectrum of metabolite M13 exhibited [M+H]$^+$ ions at m/z 584 in the positive mode, which was 307 mass units higher than that of [6]-shogaol, indicating that M13 was the GSH-conjugated [6]-shogaol (molecular weight of GSH is m/z 307). Its MS$^2$ spectrum showed product ions of m/z 277 (−307 Da, neutral loss of GSH), m/z 455 (−129 Da, neutral loss of pyroglutamic acid), m/z 437 (−147 Da, dehydrolyzation of m/z 455), and m/z 509 (−75 Da, neutral loss of glycine). The MS$^3$ spectrum of its product ion m/z 277 was almost identical to the MS$^2$ spectrum of authentic [6]-shogaol. All of the above evidence indicates M13 is the glutathiol conjugate of [6]-shogaol. Both M9 and M11 were detected as the major metabolites of [6]-shogaol in HT-29 human colon cancer cells, H-1299 human lung cancer cells, and CL-13 mouse lung cancer cells. At 24 h, [6]-shogaol was almost completely converted to M9 and M11 in H-1299 cells and to M9 in CL-13 cells.

M9 and M11 Inhibit the Growth of Human Cancer Cells.

Two cancer cell lines, HCT-116 and H-1299, were treated with [6]-shogaol, M9, or M11, with concentrations ranging from 0 to 80 μM. In HCT-116 cells, [6]-shogaol exhibited the strongest inhibitory activity with an IC$_{50}$ of 18.7 μM. The major metabolites M9 and M11 had decreasing potencies of 82.2 and 84.0 μM, respectively. In H-1299 cells, the IC$_{50}$ values for [6]-shogaol, M9, and M11 were 16.9, 77.7, and 66.5 μM, respectively. These data demonstrate that [6]-shogaol has the greatest inhibitory activity against cancer cell lines but still shows some efficacy after metabolic biotransformation.

M9 and M11 Trigger Apoptosis in Human Cancer Cells.

Apoptosis, or programmed cell death, is a major mechanism of regulation allowing cells to undergo cell death upon activation of specific external and/or internal pathways. The role of [6]-shogaol, M9, and M11 on the induction of apoptosis in human cancer cells was investigated using the TUNEL assay, which detects breaks of DNA strands in early and late apoptotic cells. In HCT-116 and H-1299 cells, exposure to 10 μM [6]-shogaol (FIGS. 2C and 2D) yielded 10.3 and 5.2% of apoptotic cells, respectively, whereas 20 μM [6]-shogaol yielded 31.2 and 31.6%. Exposure to 40 μM metabolite M9 for 24 h led to the observation of 9.6 and 7.4% of apoptotic cells, respectively (16.9 and 15.4% for the 80 μM dose, respectively). Exposure to 40 μM metabolite M11 led to the observation of 12.9 and 8.3% of apoptotic cells in HTC-116 and H-1299 cancer cells (21.1 and 19.4% for the 80 μM dose), respectively). All of these results are different from the DMSO control and show that M9 and M11 are bioactive compounds and can specifically trigger apoptosis in both human colon and lung cancer cells, but that the compounds are not as efficient as [6]-shogaol.

Chemical Synthesis of the Metabolites of [6]-Shogaol.

As generally described herein, twelve metabolites (M1, M2, and M4-M13) were synthesized successfully from [6]-shogaol using simple and easily accessible semisynthetic approaches in the current study (Schemes 1 and 2). In brief, reaction of [6]-shogaol with L-cysteine (Cys), N-acetyl-L-cysteine (N-Cys) or L-glutathione (GSH), generated thiol-conjugates M2, M5, or M13, respectively. Subsequently, reduction of thioconjugates M2 or M5 by NaBH$_4$ led to hydroxylated conjugates M1 or M4, respectively. Selective reduction of [6]-shogaol by a combination of NaBH₄ and CeCl₃·7H₂O resulted in M6 (Scheme 2). Hydrogenation of [6]-shogaol on Pd/C gave M11, followed by treatment with NaBH₄ to produce M9 (Scheme 2). In addition, demethylation of M11 using BBr₃ gave M8 (Scheme 2). Michael reaction of [6]-shogaol with NaOMe or NaSMe produced the methoxy adduct M7 or the methylthio adduct M10, respectively. The methylthio adduct M10 was treated with NaBH₄ to give M12. Since both the reduction of ketone and the Michael reactions used in this study are non-stereoselective, metabolites M1, M2, M4-M7, M9, M10, M12, and M13 are synthesized as mixtures of diasteromers.

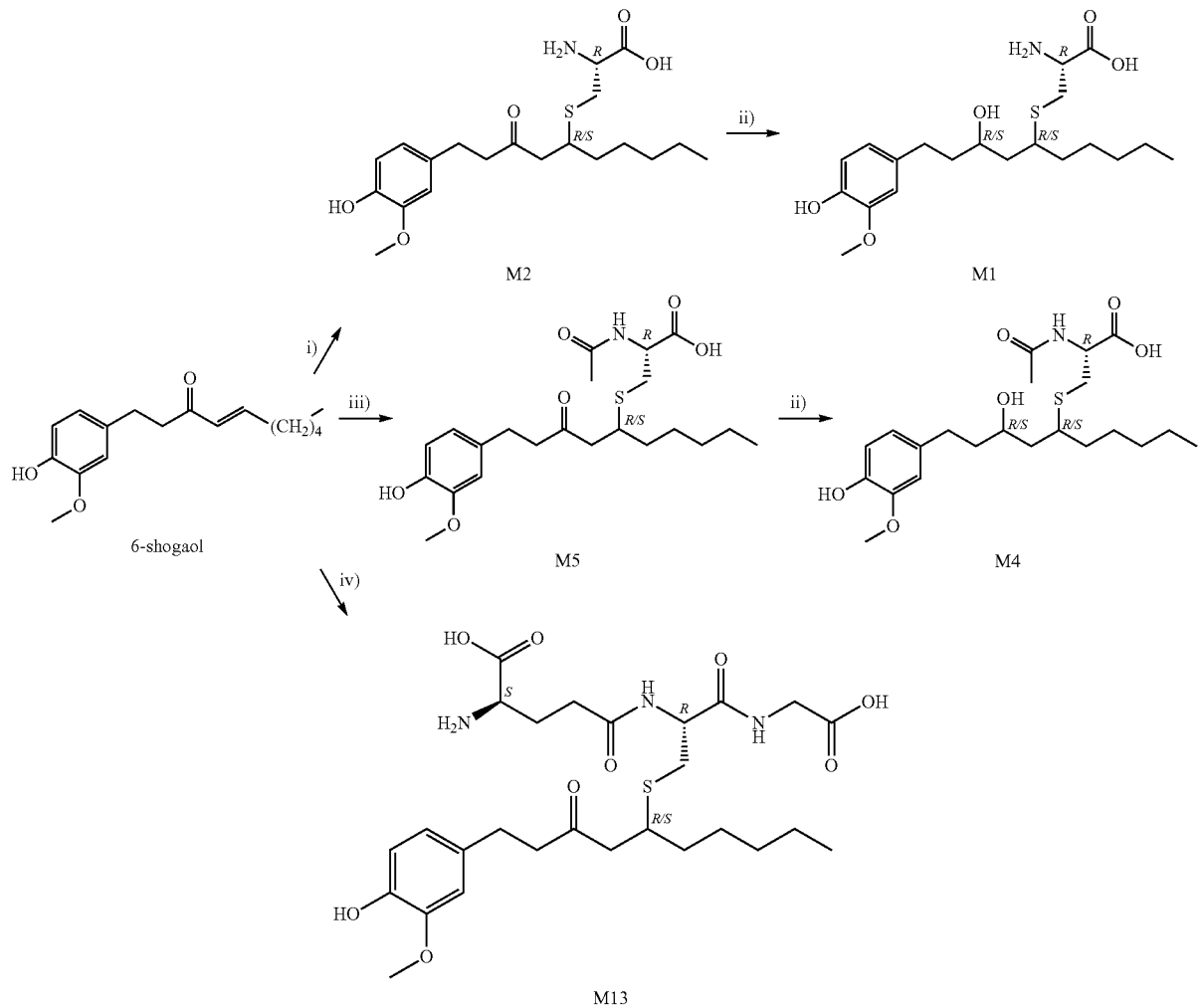

Synthesis of thiol-conjugates M1, M2, M4, M5, and M13. Reagents and conditions:
i) L-cysteine, NaHCO₃ (cat.), MeOH/H₂O, rt, 24 h;
ii) NaBH₄, MeOH, 0° C., 2 h;
iii) N-acetyl-L cysteine, NaHCO₃ (cat.), MeOH/H₂O, rt, 72 h;
iv) L-glutathione reduced, NaHCO3 (cat.), MeOH/H2O, rt, 3 h.

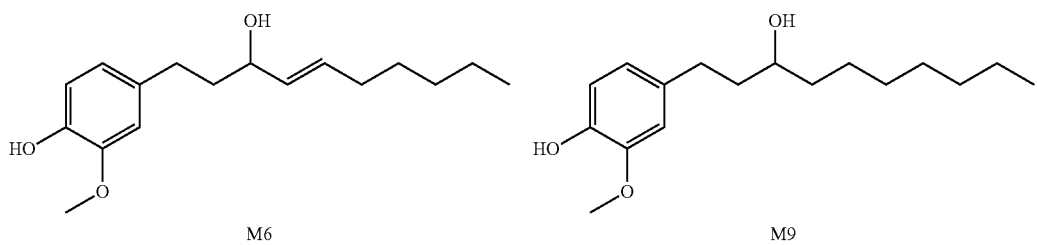

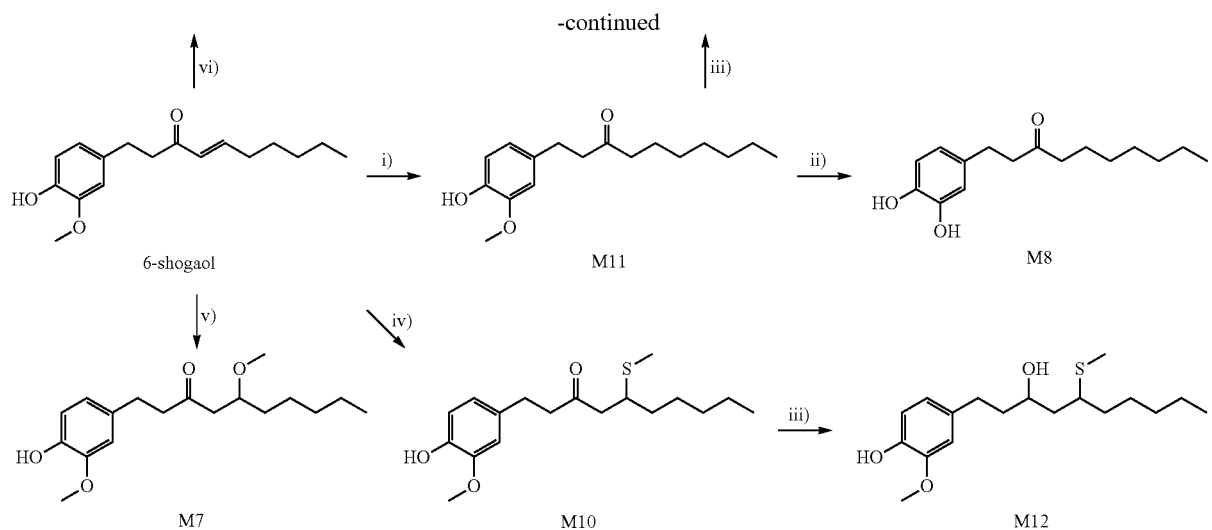

Synthesis of metabolites M6-M12. Reagents and conditions:
i) H₂, Pd/C (10% w/w), THF, rt, 18 h;
ii) BBr3, DCM, -78° C.-rt, 2 h;
iii) NaBH₄, MeOH, 0° C.-rt, 2 h;
iv) aq. 15% NaSCH3, THF, rt, 6 h;
v) Na, MeOH, 0° C.-rt, 4 h;
vi) NaBH4, CeCl₃•7H2O, MeOH, -78° C., 30 min.

The structures of M5-M12 were fully characterized using their 1-D and 2-D NMR and mass spectral data as disclosed herein. The structures of these synthetic compounds were confirmed by comparison of their $^1H$ and $^{13}C$ NMR spectra with those of authentic standards obtained from mouse fecal samples. Structures of the remaining synthetic metabolites (M1, M2, M4, and M13), deduced by multi-stage mass spectrometry techniques, were further confirmed by their 1-D and 2-D NMR spectra data.

Metabolite M2:

M2 showed the molecular formula $C_{20}H_{31}NO_5S$ on the basis of positive APCI-MS at m/z 398 [M+H]+ and its $^1H$ and $^{13}C$ NMR data. The molecular weight of M2 was 42 mass units less than that of N-acetylcysteine conjugated [6]-shogaol (M5) indicating M2 was the cysteine conjugated [6]-shogaol. This was in agreement with the fact that M2 was made by [6]-shogaol and L-cysteine. This was also supported by the observation of the absence of an acetyl group in the $^1H$ and $^{13}C$ NMR spectra of M2. The linkage of an L-cysteinyl moiety to the [6]-shogaol residue at C-5 was established by HMBC cross-peaks between HCys-β (δH 3.18 and 2.84) and C-5 (δC 42.3). Therefore, M2 was confirmed to be 5-cysteinyl-[6]-shogaol.

Metabolite M1:

M1 had the molecular formula of $C_{20}H_{33}NO_5S$ on the basis of positive APCI-MS at m/z 400 [M+H]+ and its $^1H$ and $^{13}C$ NMR data. The molecular weight of M1 was 2 mass units higher than that of M2, matching with the fact that M1 was a ketone-reduced product of M2, and also supported by the appearance of oxygenated methines (two sets of protons for the diasteromers at δH 3.66 and δH 3.90; and δC 69.3) in its $^1H$ and $^{13}C$ NMR spectra. Key HMBC correlations between H-3 (δH 3.66 and δH 3.90) to C-1 (δC 32.5) and C-5 (δC 43.8), as well as H-1 (δH 2.68 and 2.58) to C-3 (δC 69.3) in M1, established a hydroxyl group at C-3 on the alkyl side chain of M1. HMBC cross-peaks between HCys-β (δH 3.15 and 2.85) to C-5 (δC 43.8), and H-5 (δH 2.94) to CCys-β (δC 32.8) provided the linkage of the cysteinyl moiety and C-5 position of M1 through a thioether bond. Thus, M1 was confirmed to be 5-cysteinyl-M6.

Metabolite M4:

M4 showed the molecular formula $C_{22}H_{35}NO_6S$ on the basis of positive APCI-MS at m/z 442 [M+H]+ and its $^1H$ and $^{13}C$ NMR data. The molecular weight of M4 was 2 mass units higher than that of M5 (5-N-acetylcysteinyl-[6]-shogaol), complying with the fact that M4 was a ketone-reduced product of M5. This was further supported by the appearance of oxygenated methines (two sets of protons for the diasteromers at δH 3.70 and δH 3.88; and δC 69.3) in its 1H and 13C NMR spectra, the disappearance of the expected ketone carbonyl group in [6]-shogaol, and the key HMBC correlations observed at H-3 (δH 3.70 and δH 3.88) to C-1 (δC 32.5) and C-5 (δC 43.8), as well as H-1 (δH 2.67 and 2.58) to C-3 (δC 69.3) in its HMBC spectrum. The acetyl group was shown attached to α-NH₂ of the cysteinyl moiety by HMBC correlation detected at HCys-α (δH 4.54) to CH3CO (δC 174.0). In addition, HMBC cross-peaks between HCys-β (δH 3.00 and 2.80) and C-5 (δC 43.8) provided the linkage of an acetylcysteinyl moiety and the C-5 position of M4. M4, thereof, was confirmed to be 5-N-acetylcysteinyl-M6.

Metabolite M13:

M13, having the molecular formula $C_{27}H_{41}N_3O_9S$ on the basis of positive APCI-MS at m/z 584 [M+H]⁺ and its NMR data, was made by [6]-shogaol and reduced L-glutathione (GSH). $^1H$-$^1H$ COSY cross-peaks found at HGlu-α/HGlu-β/HGlu-γ, in combination with key HMBC correlations between HGlu-α (δH 3.65) to Glu α-COOH (δC 174.0) as well as HGlu-γ (δH 2.55 and 2.51) to Glu γ-CON (δC 175.2), recognized the structure of a glutamyl residue (Glu). The structure of the cysteinyl residue (Cys) was established by $^1H$-$^1H$ COSY cross-peaks at HCys-α/HCys-β in combination with HMBC correlation between HCys-β (two sets of protons at δH 3.05-2.95 and 2.84-2.80) to Cys α-CON (δC 175.2). Subsequently, the connection of the glutamyl residue with the cysteinyl moiety was established between Glu γ-COOH and Cys α-NH$^2$ through an amide bond, by HMBC correlations found at HCys-α (δH 4.50) to Glu γ-CON (δC 175.2). The attachment of a glycinyl moiety to the cysteinyl residue was found between Cys α-COOH and Gly α-NH$_2$, by HMBC correlations observed at HGly-α (δH 3.80) to Cys α-CON (δC 175.2). Thus, the GSH residue was undoubtedly identified as α-glutamyl-cysteinylglycine. Consequently, linkage of the GSH moiety to the [6]-shogaol residue was established at C-5 through a thioether bond by HMBC correlations found at HCys-β (two sets of protons at δH 3.05-2.95 and 2.84-2.80) to C-5 (δC 42.2). Therefore, M13 was confirmed to be 5-glutathiol-[6]-shogaol.

Separation of M13 isomers on preparative HPLC resulted in two diastereoisomers, M13-1 and M13-2, which had very similar $^1$H and $^{13}$C NMR spectra. The major differences were the 1H signals for HCys-βb ([H 2.73 in M13-1 vs. 2.81 in M13-2) and H-4a (δH 2.76 in M13-1 vs. 2.70 in M13-2) and the $^{13}$C signals for C-4 (δC 49.9 in M13-1 vs. 49.6 in M13-2) and C-5 (δC 42.0 in M13-1 vs. 42.4 in M13-2). In the NOESY spectra, correlations between HCys-βb (δH 2.73) and H-5 (δH 3.10) were observed for M13-1 and between HCys-βa (δH 2.97) and H-5 (δH 3.10) for M13-2, suggesting that H-5 in M13-1 had the same configuration as that of HCys-βb and H-5 in M13-2 had the same configuration as that of HCys-βa. It is known that HCys-α in GSH residue has the R configuration. The coupling constant (J=5.0 Hz) of HCys-βa (δH 2.97) with HCys-α (δH 4.49) is much smaller than that (J=8.7 Hz) of HCys-βb (δH 2.81) with HCys-α, suggesting that HCys-βa (δH 2.97) has the same R configuration as that of HCys-α and HCys-βb has the S configuration. Therefore, the configurations of H-5 in M13-1 and M13-2 were tentatively assigned as S and R, respectively.

Growth Inhibitory Effects Against Human Cancer and Normal Cells.

Figure 3:
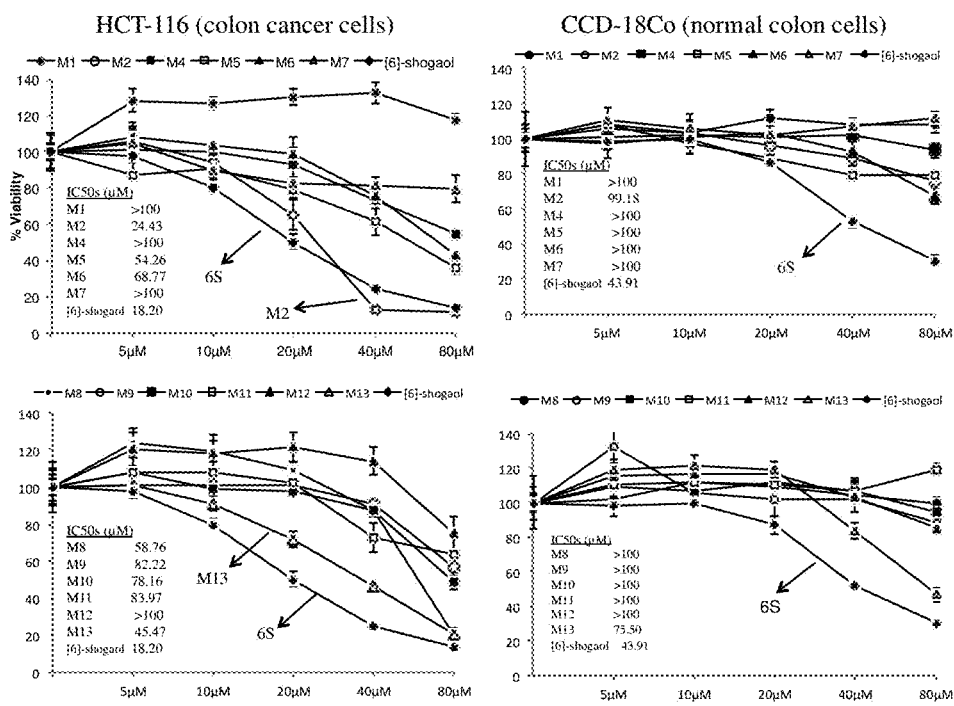
FIG. 3 shows the growth inhibitory effects of [6]-shogaol and its metabolites (M1, M2, and M4-M13) against human colon cancer cells HCT-116 and human normal colon cells CCD-18Co. Bar, standard error (n=6).
Figure 4:
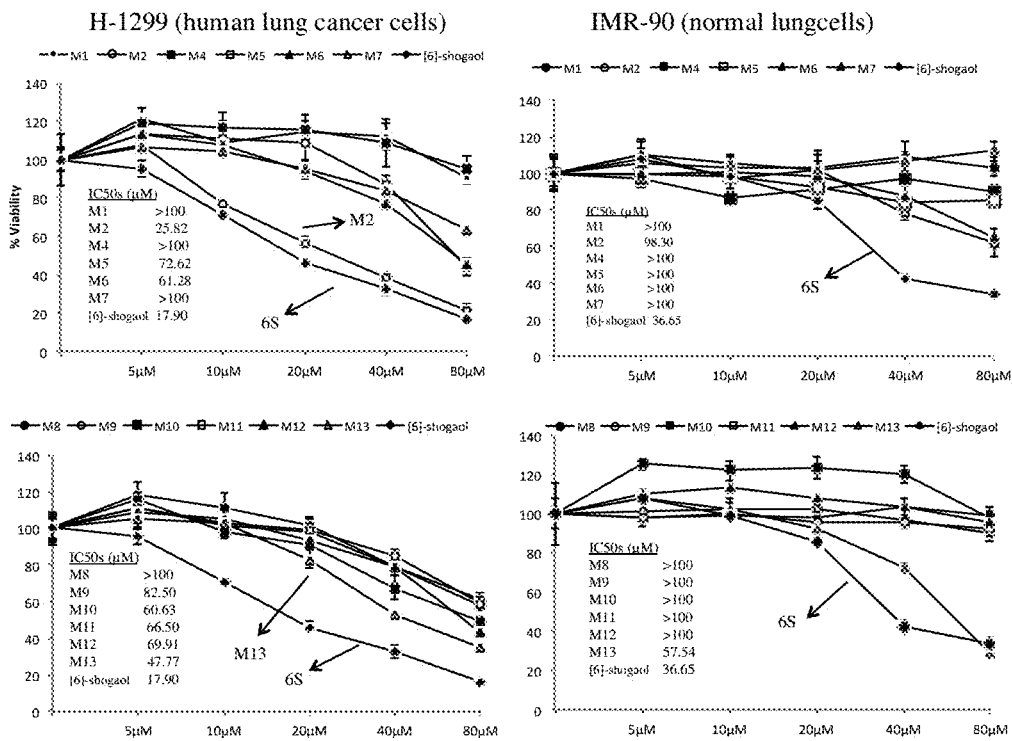
FIG. 4 shows the growth inhibitory effects of [6]-shogaol and its metabolites (M1, M2, and M4-M13) against human colon cancer cells H-1299 and human normal lung cells IMR-90. Bar, standard error (n=6).

Two human cancer cell lines, HCT-116 and H-1299, were treated with [6]-shogaol or its synthetic metabolites M1, M2, and M4-M13, with concentrations ranging from 0 to 80 μM. Cell viability assays utilizing MTT resulted in eight active metabolites, M2, M5, M6, M8-M11, and M13, against colon cancer cells HCT-116, with IC50 values of 24.43, 54.26, 68.77, 58.76, 82.22, 78.16, 83.97, and 45.47 μM, respectively (FIG. 3), and eight active metabolites, M2, M5, M6, and M9-M13, in lung cancer cells H-1299, with IC50 values of 25.82, 72.62, 61.28, 82.50, 60.63, 66.50, 69.91, and 47.77 μM, respectively (FIG. 4). Among them, M2, the cysteine conjugated metabolite of [6]-shogaol, was found to be most potent toward both HCT-116 and H-1299 cells with 1050 values of 24.43 and 25.82 μM, respectively, which was comparable to the parent [6]-shogaol, with an IC$_{50}$ of 18.20 μM in HCT-116 cells and an IC$_{50}$ of 17.90 μM in H-1299 cells. The second most active metabolite was 5-glutathionyl-[6]-shogaol (M13), with IC$_{50}$ values of 45.47 and 47.77 μM in HCT-116 and H-1299 cells, respectively. 5-N-acetylcysteinyl-[6]-shogaol (M5) also exhibited bioactivity with IC$_{50}$ values of 54.26 μM in HCT-116 cells and 72.62 μM in H-1299 cells. This metabolite, however, displayed decreased activity when compared to that of 5-cysteinyl-[6]-shogaol (M2), suggesting the acetylation on α-NH$_2$ of the cysteinyl moiety diminishes the activity of M2. Moreover, the reduction of a ketone group on the alkyl side chain resulted in little to no activity against cancer cells HCT-116 and H-1299, as observed from M1 and M4 versus M2 and M5, as well as M6, M9, and M11 versus [6]-shogaol, suggesting that the reductive biotransformation of [6]-shogaol and its metabolites was primarily inactivating.

Evaluation of cytotoxicity in human normal fibroblast colon cells CCD-18Co and human normal lung cells IMR-90 showed that all synthetic metabolites (M1, M2, and M4-M13) were less toxic than parent [6]-shogaol, and most of them had little to no inhibitory effect, indicating a detoxifying metabolic biotransformation of [6]-shogaol. The metabolite M2, having the greatest potency against both HCT-116 and H-1299 cancer cells, showed almost no toxicity towards normal colon cells CCD-18Co and normal lung cells IMR-90 with IC$_{50}$ values of 99.18 and 98.30 μM, respectively, compared to those of parent [6]-shogaol with an IC$_{50}$ of 43.91 μM toward normal colon cell line CCD-18Co and an IC$_{50}$ of 36.65 μM toward normal lung cell line IMR-90. Moreover, M13, with IC$_{50}$ values of 75.50 μM and 57.54 μM against cells CCD-18Co and IMR-90, respectively, displayed lower toxicity compared to parent [6]-shogaol.

Figure 5:
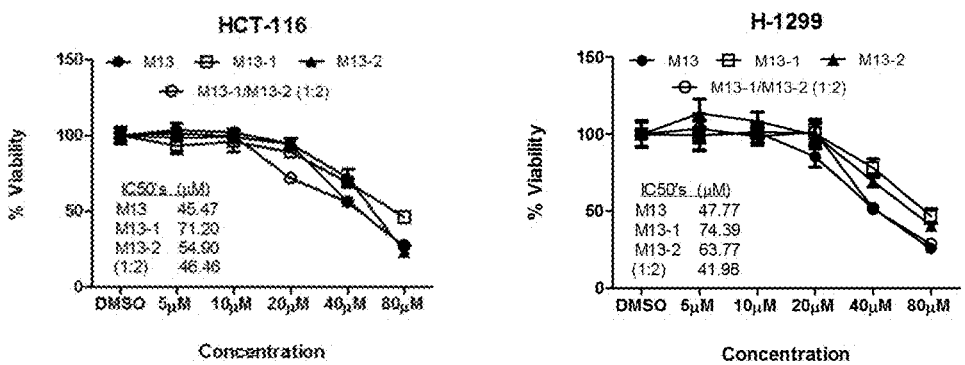
FIG. 5 shows the growth inhibitory effects of [6]-shogaol, M13, M13-1, M13-2, and a physical mixture of M13-1 and M13-2 (molar/molar=1:2) against human colon cancer cells HCT-116. Bar, standard error (n=6).

To investigate the influence of stereochemistry on activity, metabolite M13, as a mixture of diastereomers, was separated by reverse phase prep-HPLC into two individual isomers, M13-1 and M13-2. Cancer cells HCT-116 and H-1299 were treated with M13 or its constituent stereoisomers (M13-1 and M13-2) individually, with concentrations ranging from 0 to 80 μM. Both isomers had similar activity, which was slightly less than M13; M13-2 was slightly more effective than M13-1, with an IC$_{50}$ value of 54.90 μM in HCT-116 cells and 63.77 μM in H-1299 cells, versus 71.20 μM and 74.39 μM in the same respective cell lines (FIG. 5).

Reconstituted M13 by combining M13-1 and M13-2 in an approximate molar ratio of 1:2, which is similar to the ratio in original M13, displayed the equivalent activity, with IC$_{50}$ values of 46.46 μM in HCT-116 cell and 41.98 μM in H-1299 cell, compared to the original M13 with IC$_{50}$ values of 45.47 μM in HCT-116 cells and 47.77 μM in H-1299 cells, indicating that the observed growth inhibitory effect of M13 is not attributable to one isomer or the other.

M2 and M13 Induce Apoptosis in Human Cancer Cells.

Figure 6:
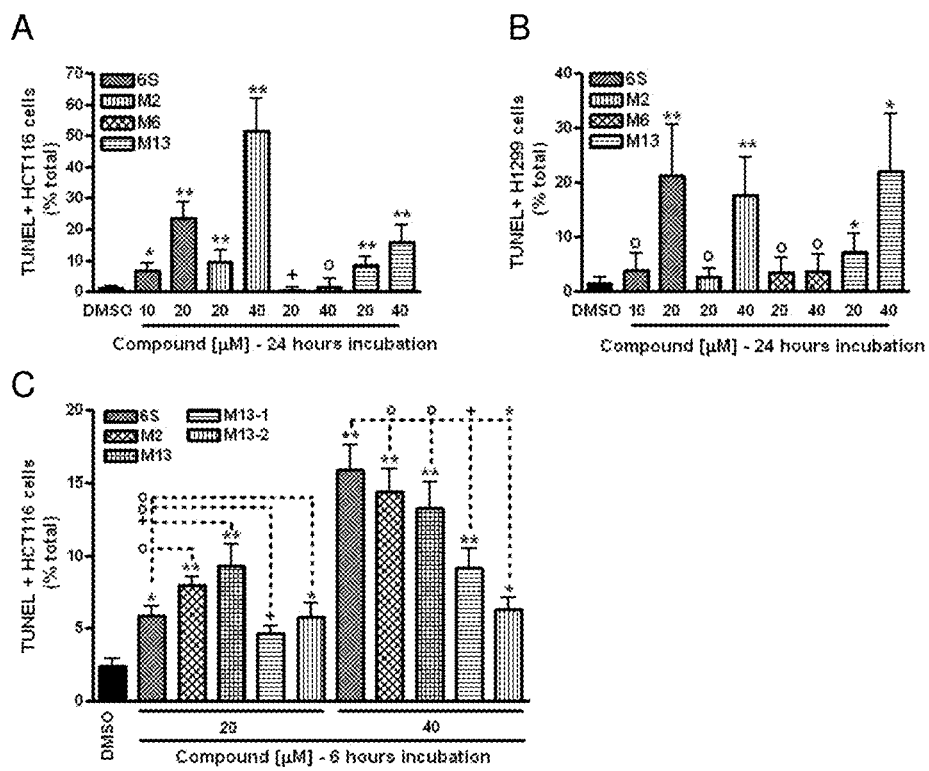
FIG. 6 shows the effects of [6]-shogaol and its metabolites M2, M6, and M13 on the induction of apoptosis in HCT-116 (A) and H-1299 (B) cells after 24 hours of incubation; and effects of [6]-shogaol, M2, M13, M13-1 and M13-2 on the induction of apoptosis in HCT-116 after 6 hours of incubation (C). TUNEL positive cells have been observed at 400× power. 10 fields per slide have been counted and averaged. Bar, standard error; o, not significant; +, $p<0.05$; *, $p<0.01$; **: $P<0.0001$. All statistical tests are unpaired Student t-test, 2 tailed, compared to DMSO or the corresponding [6]-shogaol concentration.

Cells lines H-1299 and HCT-116 were incubated with M2, M13, M6 and [6]-shogaol at various concentrations to determine the active range of these compounds versus DMSO. (FIG. 6). After 24 hours of incubation, metabolite M6 did not display any apoptotic effect in HCT-116 and H-1299 cell lines. Apoptosis was observed for M2 and M13 in both cell lines, except for M2 in H-1299 cells for the 20 μM concentration. The induction of apoptosis by [6]-shogaol was superior to that of both M2 and M13 at the same concentration (20 μM). In H-1299 cells, an equivalent apoptotic effect to [6]-shogaol could be obtained if the concentration of M2 and M13 was twice (40 μM) that of [6]-shogaol. Similar results were obtained in HCT-116 cells, except that the M2 apoptotic induction was higher at 40 μM. In all cell lines, an increase in the concentration of [6]-shogaol, M2, M13, M13-1, M13-2 or M6 yielded a corresponding increase in apoptotic level in cancer cells (FIG. 6).

Each of [6]-shogaol, M2 and M13 were incubated in HCT-116 cells for only 6 hours (FIG. 6). After 6 hours of incubation with [6]-shogaol or metabolites M2 or M13, higher levels of apoptosis for all 3 compounds were detected compared to DMSO in HCT-116 cells. Interestingly there was no significant difference between the apoptotic effect of [6]-shogaol and the effects of M2 at 20 and 40 μM and M13 at 40 μM. M13 was more potent than [6]-shogaol at 20 μM. Exposure of HCT-116 cells to M13 isomers M13-1 and M13-2 also showed a higher level of apoptosis, but the isomers' apoptotic effect was inferior compared to [6]-shogaol for both concentrations used. These results show that apoptosis is triggered by [6]-shogaol metabolites M2, M13, M13-1 and M13-2, and is one mechanism at least partially responsible for the cell death observed previously.

Incubation Conditions of [6]-Shogaol with Human Liver Microsomes

Transformation of [6]-shogaol in liver microsomes occurred more rapidly in the condition containing 0.5 mg/mL human liver microsomes than in the condition with 0.1 mg/mL microsomes. The profiles were comparable, with no noticeable difference besides the aforementioned metabolic velocity. After examining the profiles from different conditions, the incubation parameters were optimized for metabolite identification and interspecies comparison with hepatic microsomes at 0.5 mg/mL along with NADPH-regenerating system for 30 minutes.

Structure Elucidation of [6]-Shogaol Metabolites

Five major product peaks were observed in LC chromatograms after [6]-shogaol (50 µM) was incubated for 30 minutes with the hepatic microsomes from mouse, rat, dog, monkey, and humans. All of the peaks were identified by comparing their $MS^2$ spectra with those of authentic standards.

Metabolites M6, M9 and M11:

Metabolites at the retention time of 29.3, 33.9, and 41.8 min were identified as 1-(4'-hydroxy-3'-methoxyphenyl)-4-decen-3-ol (M6), 1-(4'-hydroxy-3'-methoxyphenyl)-decan-3-ol (M9), and 1-(4'-hydroxy-3'-methoxyphenyl)-decan-3-one (M11), respectively, by comparing their mass spectra with those of authentic standards that were purified from mouse feces as described before.

Metabolite M14

To identify the other two unknown peaks (M14 and M15), the sample obtained from CyLM was run on LC/MS, which indicated that M14 had a molecular weight of m/z 274 as determined by the mass ions at m/z 275 [M+H]$^+$, 297 [M+Na]$^+$, and 571 [2M+Na]$^+$, which was 2 mass units less than that of [6]-shogaol. This metabolite showed m/z 177 but not 137 (product ion of [6]-shogaol) as a major product ion, leading to a conclusion that the compound was a 1,2-dehydrogenated product of [6]-shogaol. To confirm, the compound was independently synthesized. The synthetic compound had a molecular formula $C_{17}H_{22}O_3$ on the basis of positive ESI-MS at m/z 275 [M+H]$^+$ and its $^1$H and $^{13}$C NMR data. The molecular weight of this compound (m/z: 274) was 2 mass units less than that of [6]-shogaol (m/z: 276) indicating it was dehydrogenated [6]-shogaol. This was also supported by the observation of the absence of two methenes and the presence of two more olefinic methines ($\delta_H$ 7.59 and $\delta_H$ 6.82; and $\delta_C$ 143.1 and $\delta_C$ 123.3) in its $^1$H and $^{13}$C NMR spectra. Additionally, geometry of the double bond between C-1 and C-2 was determined as E-configuration by the coupling constant $J_{1,2}=15.9$ Hz. Therefore, this compound was confirmed as (1E,4E)-1-(4-hydroxy-3-methoxyphenyl)deca-1,4-dien-3-one. M14 had almost the same retention time as well as the same mass fragment as those of the synthetic (1E, 4E)-1-(4'-hydroxy-3'-methoxyphenyl)-deca-1,4-dien-3-one and was assigned as that compound (FIG. 1).

Metabolite M15

In the same way, another peak showed a molecular weight of m/z 276 as determined by the mass ions at m/z 277 [M+H]$^+$, 299 [M+Na]$^+$, and 575 [2M+Na]$^+$. M15 had the same molecular weight as that of [6]-shogaol, suggesting that it was a double bond transferred metabolite of [6]-shogaol. To confirm, this compound was synthesized using M11 as described in the experimental section. The synthetic compound had a molecular formula $C_{17}H_{24}O_3$ on the basis of positive ESI-MS and its $^1$H and $^{13}$C NMR data. The molecular weight of this compound was 2 mass units less than that of M11, coinciding with the fact that it was a dehydrogenated product of M11, and also supported by the appearance of two olefinic methines ($\delta_H$ 7.47 and $\delta_H$ 6.59; and $\delta_C$ 142.6 and $\delta_C$ 124.2) in its $^1$H and $^{13}$C NMR spectra. Additionally, the E-configuration between C-1 and C-2 was determined by the coupling constant $J_{1,2}=16.1$ Hz. Therefore, this compound was confirmed to be (E)-1-(4'-hydroxy-3'-methoxyphenyl)-dec-1-en-3-one. M15 had almost the same retention time as well as the same mass fragment as those of the synthetic (E)-1-(4'-hydroxy-3'-methoxyphenyl)-dec-1-en-3-one, and was assigned as that compound (FIG. 1).

Metabolism of [6]-Shogaol by Liver Microsomes from Different Species

The metabolic profiles of [6]-shogaol in liver microsomes from mouse (MLM), rat (RLM), dog (DLM), and monkey (CyLM) were similar to those in human (HLM) as the five major metabolites, M6, M9, M11, M14, and M15 were detected in all five species. Monkey liver microsomes gave the highest abundance of oxidized metabolites after 30 minutes incubation, in stark contrast to human liver microsomes, which gave the least. These results suggest stronger interspecies differentiation in the enzymes responsible for [6]-shogaol oxidative metabolism than its reductive metabolism, which is seemingly conserved.

Chemical Inhibition Studies

To determine the inclusion of CYP-450 enzymes in [6]-shogaol metabolism, ABT, a broad-specificity P450 inactivator, was applied to incubations of liver microsomes with [6]-shogaol. In humans the oxidative metabolism was abrogated yet reductive metabolism still occurred. This result was similar in mouse, rat, dog, and monkey. Without being bound by theory, CYP-450 enzymes were implicated in oxidative metabolism of [6]-shogaol. As the broad-specificity P450 suicide substrate ABT did not inhibit reductive metabolism in all species, it was clear that non-P450 enzymes were implicated. Application of 18β-glycyrrhetinic acid, a known aldo-keto reductase inhibitor to the reaction mixture of HLM decimated the reductive metabolism of [6]-shogaol.

Kinetics

Figure 7:
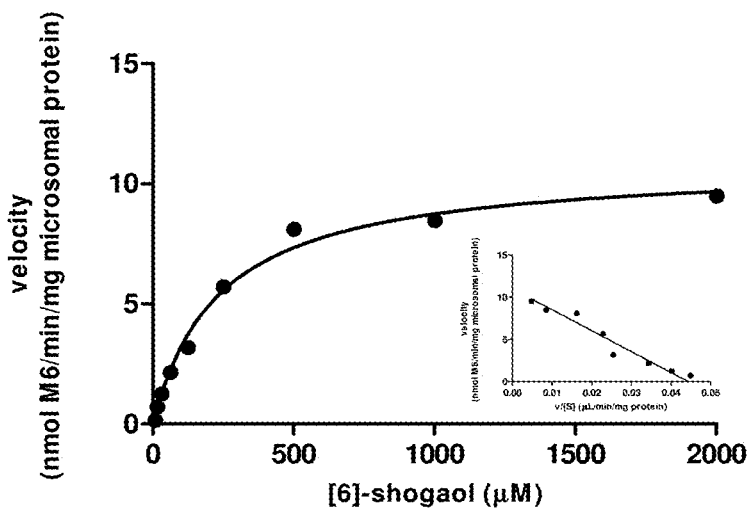
FIG. 7 shows Michaelis-Menten plot of [6]-shogaol metabolism to M6 in human liver microsomes. [6]-Shogaol was incubated with HLM at 37° C. for 30 minutes with an NADPH-regenerating system. An Eadie-Hofstee plot is shown as an insert to illustrate monophase kinetics. Data points represent the mean of triplicate determinations.

Over the concentration range tested, metabolism of [6]-shogaol to M6 in liver microsomes from humans and four animal species obeyed Michaelis-Menten kinetics, as evidenced by the Eadie-Hofstee plot (FIG. 7). The kinetic parameters, including $K_m$, $V_{max}$, and the intrinsic clearance ($V_{max}/K_m$), were determined and are listed in Table 3. In human liver microsomes, the $K_m$ value for M6 formation was 45.6 µM and the $V_{max}$ was 10.82+/−0.47 nmoles per minute per milligram microsomal protein. In liver microsomes from four experimental animals, the $K_m$ values for M6 formation ranged from 75.7 µM (mouse) to 424.2 µM (monkey), displaying vast interspecies variation. The $V_{max}$ values for the remaining four species varied as well, with 2.99+/−0.28 (monkey) to 8.19+/−0.48 (rat) nmoles per minute per milligram enzyme, a kinetic trend that was consistent with the perceived relative formation rates of M6 across five species in the HPLC-ECD chromatogram. Intrinsic clearance values varied across all five species, from 7.0 µL per minute per milligram protein (monkey) to 80.5 µL per minute per milligram protein (rat), indicating the relative affinities of M6 formation from lowest to highest in CyLM and RLM, respectively.

TABLE 3

Kinetic parameters of M6 metabolism in liver microsomes: $K_m$ values are in micromolar values. $V_{max}$ values are nanomoles per minute per milligram liver microsomes. The range of substrate concentrations was 7.8 to 2000 μM. Each value is the mean +/- S.D. of three independent experiments.

| Species | $V_{max}$ | $K_m$ | $V_{max}/K_m$ |
|---|---|---|---|
| Human | 10.82 +/- 0.47 | 237.2 +/- 32.7 | 45.6 |
| Monkey | 2.99 +/- 0.28 | 424.2 +/- 108.3 | 7.0 |
| Dog | 7.33 +/- 0.43 | 251.1 +/- 42.99 | 29.2 |
| Rat | 8.19 +/- 0.48 | 101.7 +/- 22.62 | 80.5 |
| Mouse | 4.10 +/- 0.19 | 75.7 +/- 12.17 | 54.2 |

Growth Inhibitory Effects Against Human Cancer and Normal Cells

Figure 8:
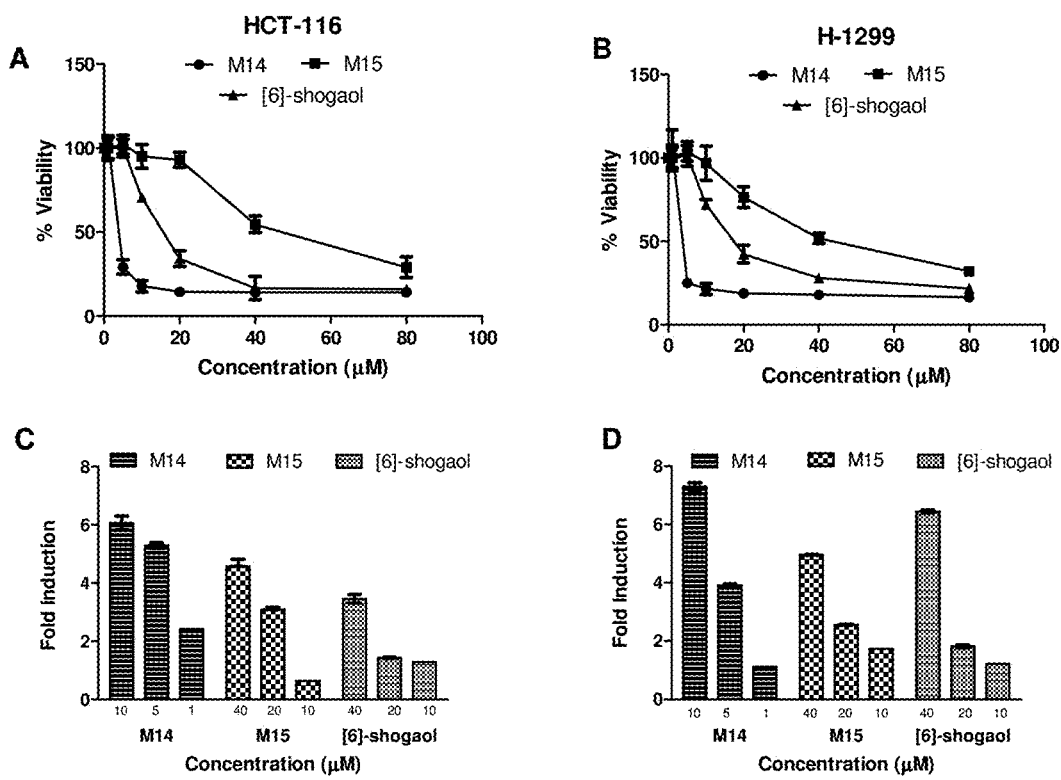
FIG. 8 shows growth inhibition and induction of apoptosis by M14, M15 and [6]-shogaol against human cancer cells. Human colon cancer (HCT-116) (A) and human lung cancer (H-1299) (B) cells were incubated with respective metabolites or [6]-shogaol for 24 hours and tested for cell viability. Values are given as percent of positive control, where n=6. Induction of apoptosis by of M14 and M15. Human colon cancer cells (HCT-116) (C) and human lung cancer cells (H-1299) (D) were incubated with respective metabolites or [6]-shogaol for 24 hours and tested for induction of apoptosis. Values are given as fold induction against DMSO control, where n=3.

Two human cancer cell lines, HCT-116 and H-1299, were treated with [6]-shogaol or its synthetic metabolites M14 and M15, with concentrations ranging from 0 to 80 μM. Cell viability assays utilizing MTT resulted in high potency of M14 and moderate potency of M15, relative to [6]-shogaol, with $IC_{50}$ values of 3.22, 43.02, and 19.94 μM, respectively, against colon cancer cells HCT-116 (FIG. 8A). In lung cancer cells H-1299, a similar trend was observed with M14, M15, and [6]-shogaol, with $IC_{50}$ values of 3.04, 41.59, and 17.32 μM, respectively (FIG. 8B).

Induction of Apoptosis in Human Cancer Cells by M14, M15, and [6]-Shogaol

Following the implications of cytotoxicity in cancer cells induced by M14, M15, and [6]-shogaol, the pro-apoptotic properties of these compounds were measured (FIGS. 8C and 8D). M14 was the most potent compound, with induction of apoptosis of about 6-fold in HCT-116 cells and about 7-8 fold in H-1299 cells, compared to DMSO control after administration of 10 μM compound and 24 hours incubation. Treatment of 1 μM M14 gave a 2-fold induction of apoptosis in HCT-116 cells and 1-fold induction in H-1299 cells, compared to DMSO control. Metabolite M15 gave similar, if somewhat greater apoptotic effects against both cancer cell lines after treatment for 24 hours, as parent compound [6]-shogaol. Administration of 10 μM M15 or [6]-shogaol was sufficient in both cell lines to induce apoptosis, by 1-fold in HCT-116 and almost 2-fold in H-1299. The similarities in pro-apoptotic potencies between [6]-shogaol and M15 was not entirely expected, as [6]-shogaol was more than twice as toxic in the previous MTT assays. However, as apoptosis is a specific form of cell death, the results are not unreasonable.

Figure 9:
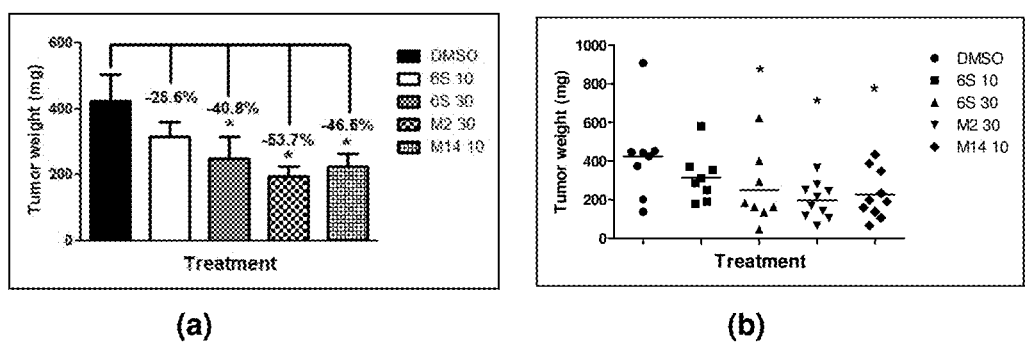
FIG. 9 shows the change in tumor weight upon treatment of 6S, M2 and M14.

Xenograft Study 8 week-old nude mice (Jackson Laboratory, Maine) were randomized into 5 groups based on treatment (DMSO: n=4; 6S 10 mg/kg: n=4 ("6S 10"); 6S 30 mg/kg: n=4 ("6S 30"); M2 30 mg/kg: n=5 ("M2 30"); M14 10 mg/kg: n=4 ("M14 10")). Animals were implanted with $5 \times 10^6$ A549 lung cancer cells (adenocarcinomic human alveolar basal epithelial cells) on each flank. The mice had access to food and water ad libitum. One week post implantation, the animals started receiving their respecting treatments through oral gavage (100 μl in corn oil and 5% DMSO), 5×/week. After 7 weeks of treatment, the tumor tissues were harvested. Reduction in tumor size was observed between the control group and the 6S 30, M2 30 and M14 10 groups (FIG. 9). Additionally, the M2 group showed a 12.9% lower tumor burden than the equivalent 6S group compared to DMSO, equivalent to a 21.8% decrease. Based on the results of this xenograft study, 6S inhibits lung tumor growth in a dose-dependent manner.

6S and M2 are Similarly Metabolized by IMR90 and A549 Cells 6S is metabolized by IMR90 or A549 cells, with an initial conversion into mostly metabolites identified as M2, M13 and M11, while in later time points most of 6S has been metabolized into M9. The structures of all metabolites were confirmed using LC/MS analysis. As reported in HCT-116 and H-1299 cells, M2 metabolism in IMR90 or A549 cells was characterized by an initial conversion of this cysteine-conjugated metabolite back into 6S, which is then metabolized in a similar pattern. Thus, normal lung IMR90 and lung cancer A549 cells quickly metabolize 6S and M2 in a similar pattern.

6S and M2 Influence GSH Levels in A549 Cells

Figure 10:
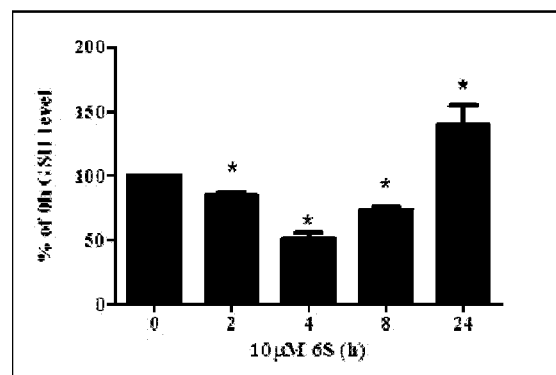
FIG. 10 shows: (A) Intracellular total GSH levels and (C) GSH/GSSG ratio in A549 treated with 10 µM of 6S for 0, 2, 4, 8 and 24 hours. $[GSH]_{DMSO\ 0hr}$=43.37±5.85 nmole/mg. (B) Intracellular total GSH levels and (D) GSH/GSSG ratio in A549 treated with 10 µM of M2 for 0, 2, 4, 8 and 24 hours. $[GSh]_{DMSO\ 0hr}$=44.46±5.16 nmole/mg. bars, SEM. *, p<0.05 by Student t-test.
Figure 10:
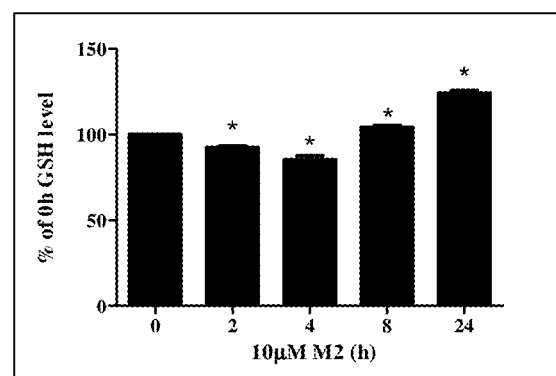
Figure 10:
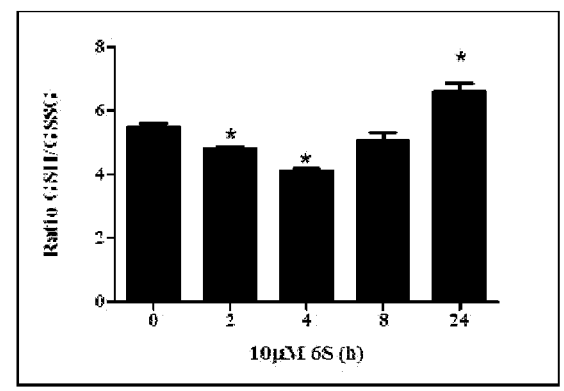
Figure 10:
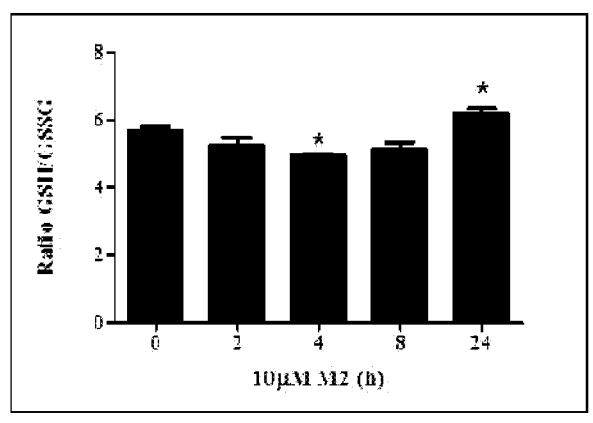

FIGS. 10A and 10B show that GSH levels are significantly depleted as early as 2 hours after exposure to 10 μM of 6S or M2; this depletion continues after 4 hours. After 8 hours, GSH levels were still significantly lower in 6S treated cells, and significantly higher in M2 treated cells. After 24 hours, GSH levels were significantly increased after exposure to both compounds compared to baseline. While changes of GSH levels is not as large as those of 6S in the case of M2, it is nonetheless significant for all tested time points.

The results of the GSH/GSSG assay are presented in FIG. 10C (6S) and 10D (M2) and show that after 2 hours the GSH/GSSG ratio is significantly lower for 6S-treated (10 μM) cells but not for M2-treated (10 μM) cells. After 4 hours of exposure to 6S or M2, the GSH/GSSG ratio is significantly lower and after 24 hours of exposure it is significantly higher. Without being bound by theory, these results show that both 6S and M2 can deplete GSH levels and induce oxidative stress in A549 cells in a similar fashion.

M2 Toxicity can Selectively Discriminate Between Normal and Cancer Cells Compared to 6S The bioactivity of 6S and M2 in A549 cells as well as in IMR90 normal human lung cells were compared in an MTT assay (FIG. 11A). When treated with increased concentration of 6S or M2, an increase in toxicity in A549 cells with $IC_{50}$'s of 25.2 and 30.4 μM, respectively, was observed. In normal IMR90 cells, the $IC_{50}$ was 36.6 and 98.3 μM for 6S and M2, respectively. Thus, in normal cells the $IC_{50}$ value was 45.6% higher for 6S and 223.2% higher for M2 when compared to A549 cells, suggesting that 6S and M2 exert similar toxicity towards A549 cells. However, M2 toxicity is greatly diminished against normal cells compared to that of 6S.

| Cell/Compound | IC50's (μM) |
|---|---|
| A549 6S | 25.17 |
| IMR90 6S | 36.65 |
| A549 M2 | 30.41 |
| IMR90 M2 | 98.3 |

6S and M2 Activate Apoptosis and p53 Pathways

Figure 11:
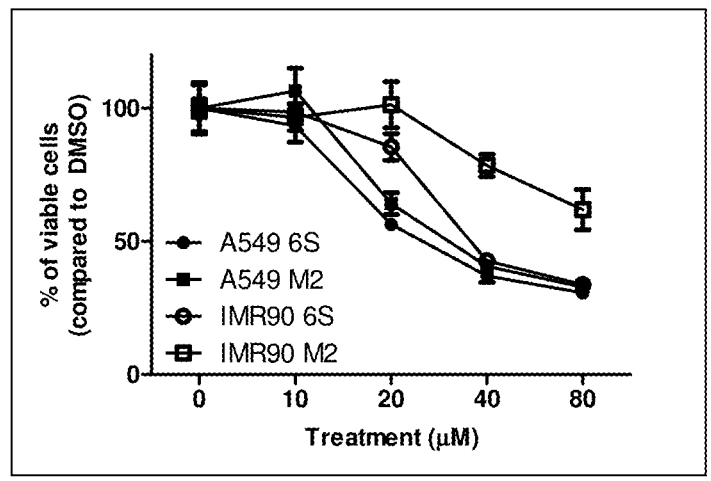
FIG. 11 shows (A) 6S and M2 toxicity in A549 cancer cells and IMR90 normal lung cells using MTT assay, with the corresponding $IC_{50}$ values on the right side table. (B) Apoptosis measured by ELISA assay in A549 cells after 24 hour treatment with 10 or 20 µM of 6S. (C) Apoptosis measured by ELISA assay in A549 cells after 24 hour treatment with 10 or 20 µM of M2. bars, SEM. ‡, p<0.05, ‡‡, p<0.01 using one-way ANOVA followed by Bonferroni's post-test.
Figure 11:
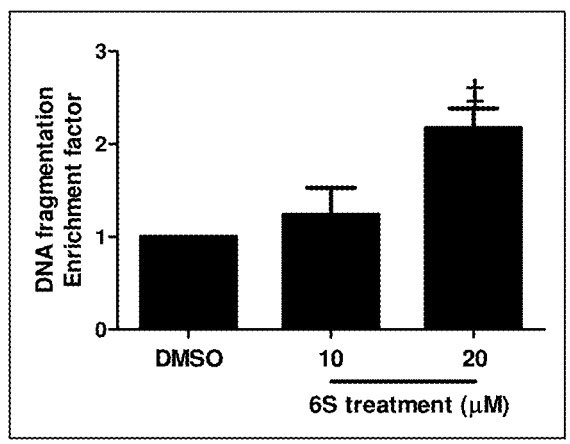
Figure 11:
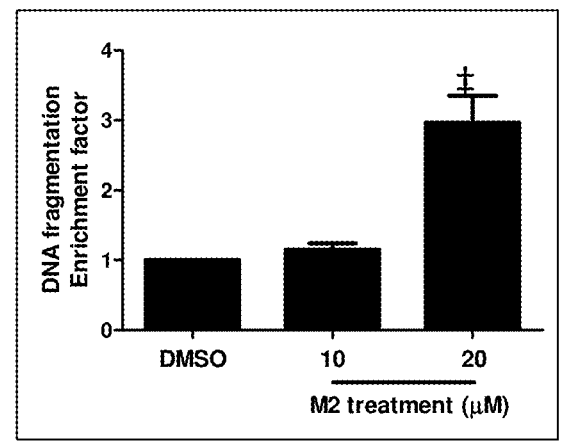

An ELISA assay quantified the release of cytoplasmic histone-associated DNA fragments in A549 cells exposed to 6S and M2 for 24 hours (FIG. 11). FIG. 11B shows that after 24 hours these apoptotic markers were higher (enrichment factor of 2.2) for cells treated with 20 μM of 6S. For M2 (FIG. 11O) an increase in apoptotic markers (about 3-fold enrichment) for the 20 μM concentration was observed.

Western blot analyses were conducted on extracts of A549 cells treated with 20 or 40 μM of 6S or M2 for 2 or 24 hours. For both concentrations of 6S and M2, the pro-apoptotic markers cytochrome C, cleaved caspase 3 and 9 were elevated after 2 hours. Only cleaved caspases 3 and 9 levels remained elevated after 24 hours, especially at the 40 μM concentration. A small increase of caspases 3 and 9 after 2 hours of exposure was also noted, and these levels were lower after 24 hours. Markers of the mitochondrial apoptotic pathway Bax, Bak and Bcl-2 were all slightly elevated after 2 hours of exposure to the test compound but their levels were close to that of DMSO-treated cells after 24 hours.

An investigation of the p53 pathway, which is responsive to oxidative stress and capable of triggering apoptosis, showed an increase in p53 levels after 2 and 24 hours for both 6S and M2, correlated to an increase of one of its downstream effectors PUMA (p53 upregulated modulator of apoptosis), which was most evident after 24 hours. Thus, both 6S and M2 activate the p53 and apoptosis pathway.

Figure 12:
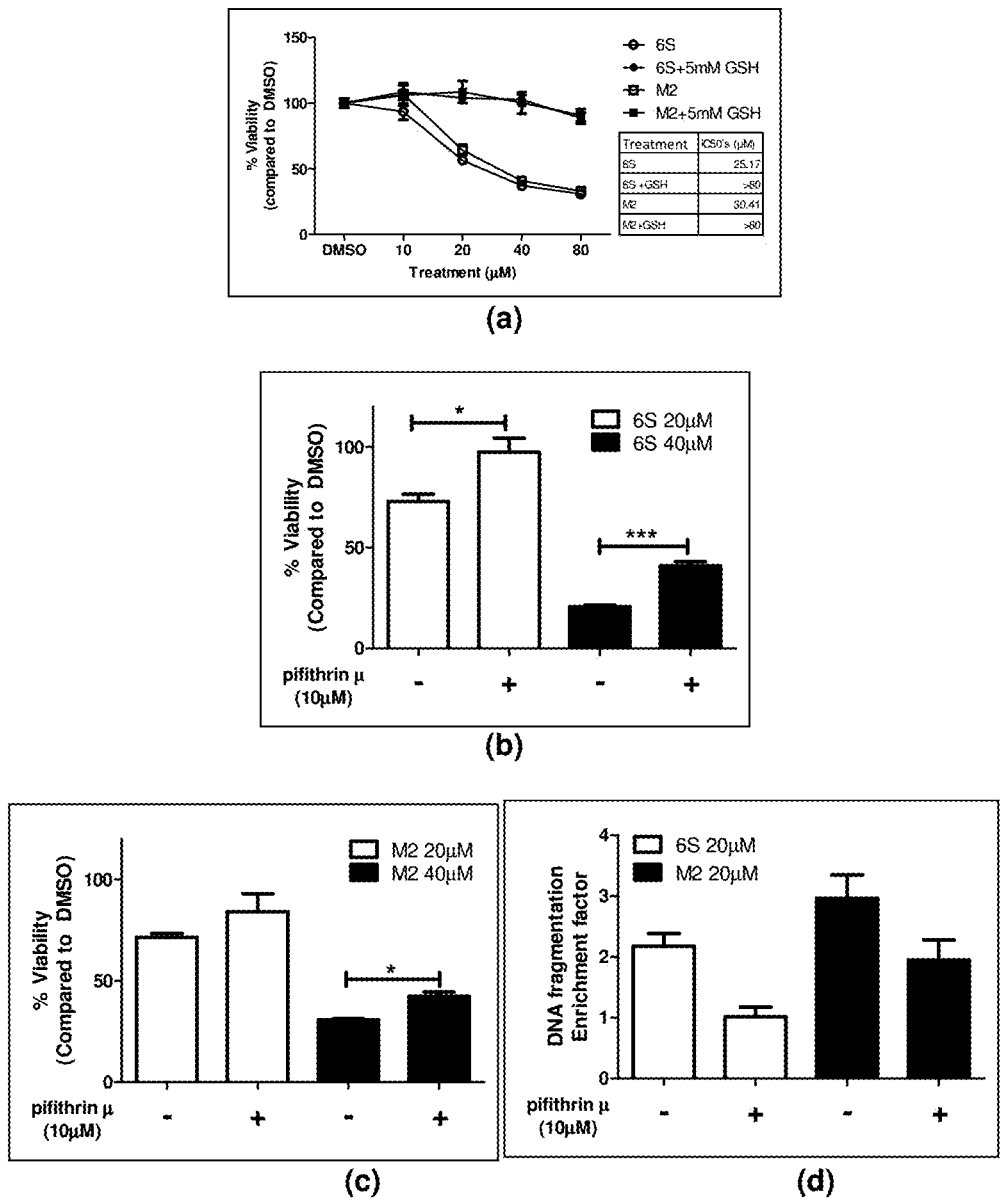
FIG. 12 shows (A) GSH rescue assay in A549 cells. Cells were treated for 24 hours with 0, 10, 20, 40 or 80 µM of 6S or M2 in the presence or absence of 5 mM GSH. The associated table indicates the $IC_{50}$ values for each treatment. (B) Effect of pft treatment on A549 cell death after treatment with 20 or 40 µM of 6S for 24 hours. (C) Effect of pft treatment on A549 cell death after treatment with 20 or 40 µM of M2 for 24 hours. (D) Effect of pft treatment on A549 cell apoptosis after treatment with 20 µM of 6S or M2 for 24 hours. bars, SEM. * p<0.05; *** p<0.001 using a paired Student's t-test; ‡: p<0.05 using one-way ANOVA followed by Bonferroni's post-test.

Excess GSH can Rescue A549 Cells from 6S and M2 Toxicity and Suppress p53 Activation Excess GSH in the culture media rescued A549 cells from both 6S and M2 toxicity, with modified $IC_{50}$'s over 80 μM (FIG. 12A). Western blot analysis showed that in the presence of excess GSH, there was no change in p53 expression in the 24 hours extracts of cells treated with 40 μM 6S or M2. Changes in GSH levels induced by both 6S and M2 in A549 cells are necessary to induce toxicity and the p53 pathway.

The Transcription-Independent Mitochondrial p53 Pathway is Involved in 6S and M2-Induced Toxicity and Apoptosis After determining the p53 involvement in A549 apoptosis and the weak modulation of the Bcl-2 family members (such as Bax), the p53-specific inhibitor pifithrin μ (pft), which specifically blocks the direct interaction and mitochondrial relocation of p53 with members of the Bcl-2 family, was investigated. Treatment of A549 cells with pft in addition to 6S was effective in reducing the toxic effect of both 6S (FIG. 12B) and M2 (FIG. 12C). When treated with 20 μM of 6S or M2 for 24 hours, the percentage of viable cells was close to 100% for 6S and 84.2% for M2. Without pft to block p53 interaction with Bcl-2 family members, the percentage of viable cells was around 72% in both cases. This effect was also observed at a higher dose of compound (40 μM). In the case of 6S, the percentage of viable cells was higher (20.6% of viable cells without pft and 41% of viable cells with pft). For 40 μM M2 the effect was similar, with 30.6% of viable cells without pft and 42.4% of viable cells with pft. Interference with p53 signaling can at least partially rescue cells from 6S and M2-induced toxicity.

Since pft directly interferes with p53 signaling towards the mitochondria, the effect of pft on apoptosis induction in A549 cells was studied. For this experiment, a 20 μM dose was used. Treatment with pft reduced the enrichment factor in small nucleosomes by a factor of 1 for both 6S and M2 (FIG. 12D): in the case of 6S the presence of pft returned the enrichment factor to baseline (about 1), while in the case of M2 the enrichment factor is down to 2 with pft from 3 without pft.

6S and M2 induce cell apoptosis through the modulation of GSH levels and the activation of the transcription-independent mitochondrial p53 pathway.

6S and M2 can Reduce A549 Cells Tumor Burden in Nu/J Mice

Figure 13:
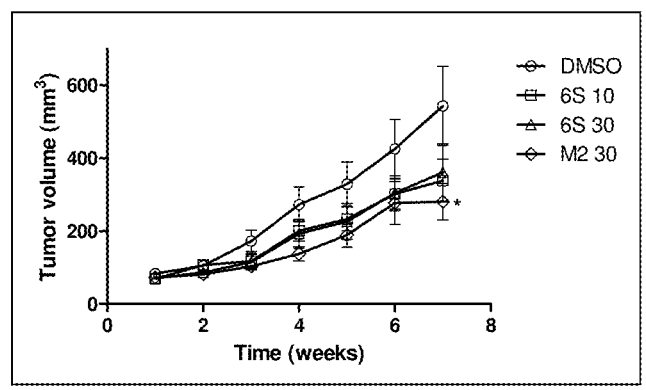
FIG. 13 shows a xenograft experiment using A549 cells in nude mice. Animals were oral-gavaged 5×/week for 7 weeks with DMSO (control), 10 mg 6S per kg body weight (6S 10), 30 mg 6S per kg body weight (6S 30), or 30 mg M2 per kg body weight (M2 30). (A) Changes in tumor volume (in $mm^3$) after 1, 2, 3, 4, 5, 6 and 7 week treatment with test compounds. (B) Wet tumor weight after 7 week treatment. * p<0.05; ** p<0.01 using unpaired Student's t-test.
Figure 13:
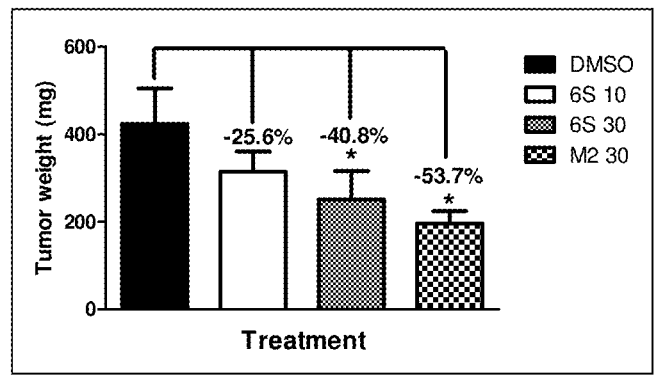

The effect of 6S and M2 on the development of A549 tumors in a mouse xenograft model was investigated. Exposure to a daily oral gavage of animals for up to 7 weeks did not induce any significant changes in body weight between groups. Tumor volume in the control group grew exponentially, tumors from the groups receiving 6S 10 mg/kg, 6S 30 mg/kg or M2 30 mg/kg grew slower, with tumors from the M2 group being different by week 7 (FIG. 13A). After 7 weeks, tumor weight was lower in both 6S 30 mg/kg (minus 40.8% compared to DMSO-treated control) and M2 30 mg/kg (minus 53.7% compared to DMSO-treated control). Tumor weight was also lower in the 6S 10 mg/kg group (minus 25.6%), albeit not significantly (FIG. 13B). Taken altogether, these results show that 6S and M2 exposure does not induce toxicity in animal. Both treatments were sufficient to lower the tumor burden of A549 engrafted cells at a 30 mg/kg body weight.

6S and M2 Induce Apoptosis and Reduce Cell Proliferation in A549 Xenografts

TUNEL staining of tumor tissues showed a marked increase of apoptotic bodies in the animals treated with 6S 10 mg/kg body weight (27.8 $TUNEL_+$ cells/field) compared to control (about 15.5 $TUNEL_+$ cells/field). This trend became significant in the tumors from animals treated with 6S 30 mg/kg, with an average of 32.6 $TUNEL_+$ cells/field. In the case of the animals treated with M2 30 mg/kg, the same trend (28.6 $TUNEL_+$ cells/field) was observed (p=0.0669). BrdU staining of tumor tissues showed a reduction of cell proliferation in the animals treated with 6S 30 mg/kg body weight (3.4 $BrdU_+$ cells/field) compared to control (about 6.3 $BrdU_+$ cells/field). A marked reduction of cell proliferation in both the 6S 10 mg/kg group (4.7 $BrdU_+$ cells/field) was also observed (p=0.0678 by unpaired t-test compared to control). While there was also a slight decrease in the M2 30 mg/kg group (5.7 $BrdU_+$ cells/field), it was also very close to significance (p=0.0558 by unpaired t-test compared to control). Thus, generally the reduction in tumor burden in vivo can be correlated to the induction of apoptosis for 6S and M2 and in the case of 6S it can be associated to other molecular mechanisms, such as cell proliferation.

Cysteine Conjugation of a Ginger Extract with High Shogaols".

Concentration of Shogaols in Ginger Extract

One gram ginger extract with high shogaols typically contains 259 mg 6S (0.94 mmol), 35.5 mg 8S (0.12 mmol), and 79 mg 10S (0.24 mmol). (Total shogaols: 1.3 mmol).

Procedure for Michael Addition Reaction of Ginger Extract and Cysteine.

A catalyst amount of $NaHCO_3$ (12 mg, 0.14 mmol) was added to a mixture of ginger extract with high shogaols (1 g including 1.3 mmol shogaols) and L-cysteine (173 mg, 1.1 eq) in methanol/water (20 mL; 10:10, v/v). The mixture was stirred at room temperature (rt) for 24 h. Then 1 mL HOAc solution (1 M) was added to the reaction mixture. The reaction mixture was then dried out by rotary evaporator. The residue was chromatographed on a silica gel column eluted with a mixture of $CHCl_3$/MeOH (3:1 and 100% MeOH). The MeOH eluted fraction give cysteine-conjugated shogaols, M2, M2' and M2".

Synthesis and Structure Elucidation of M2' and M2"

A similar experimental procedure was used for the syntheses of M2' and M2" as the previous protocol used for M2. M2' showed the molecular formula $C_{22}H_{35}NO_5S$ on the basis of positive ESI-MS at m/z 426 $[M+H]^+$ and its $^1H$ and $^{13}C$ NMR data. The molecular weight of M2' was 121 mass units more than that of 8S (M. W.: 304), indicating M2' was the cysteine-conjugated 8S, which is an expected result from the reaction between 8S and L-cysteine. This was also supported by the observation of the absence of a double bond in the $^1H$ and $^{13}C$ NMR spectra of M2'. Therefore, M2' was confirmed to be 5-cysteinyl-8S. In the same way, M2"

was identified as 5-cysteinyl-10S, based on its positive ESI-MS at m/z 454 [M+H]$^+$ and its $^1$H and $^{13}$C NMR data (Table 4).

TABLE 4

$\delta_H$ (600 MHz) and $\delta_C$ (150 MHz) NMR spectra data of M2' and M2" (CD$_3$OD, δ in ppm and J in Hz).

| | M2' | | M2" | |
|---|---|---|---|---|
| | $\delta_H$ multi (J) | $\delta_C$ | $\delta_H$ multi (J) | $\delta_C$ |
| 1 | 2.81 m | 31.6 | 2.81 m | 31.8 |
| 2 | 2.81 m | 48.1 | 2.81 m | 48.1 |
| 3 | | 210.4 | | 210.4 |
| 4 | 2.88 m | 53.8 | 2.89 m | 53.8 |
| | 2.81 m | | 2.81 m | |
| 5 | 3.11 m | 40.9 | 3.11 m | 40.9 |
| 6 | 1.56 m | 34.9 | 1.56 m | 34.9 |
| 7 | 1.42, m | 27.4 | 1.42, m | |
| 8 | 1.31, m | 31.8 | 1.31, m | 31.8 |
| 9 | 1.31, m | 29.2$^a$ | 1.31, m | 29.3$^a$ |
| 10 | 1.31, m | 28.9$^a$ | 1.31, m | 29.3$^a$ |
| 11 | 1.31, m | 28.9$^a$ | 1.31, m | 29.2$^a$ |
| 12 | 1.31, m | 26.4$^a$ | 1.31, m | 29.1$^a$ |
| 13 | 0.92 t (6.9) | 22.3 | 1.31, m | 28.9$^a$ |
| 14 | | 13.0 | 1.31, m | 26.4$^a$ |
| 15 | | | 1.31, m | 22.3 |
| 16 | | | 0.92 t (6.9) | 13.0 |
| 1' | | 132.4 | | 132.4 |
| 2' | 6.80 d (2.0) | 111.7 | 6.80 d (2.0) | 111.8 |
| 3' | | 147.8 | | 147.7 |
| 4' | | 144.4 | | 144.4 |
| 5' | 6.71 d (7.98) | 115.0 | 6.71 d (7.98) | 115.0 |
| 6' | 6.65 dd (7.98, 2.0) | 120.4 | 6.65 dd (7.98, 2.0) | 120.5 |
| 1" | a: 3.21 m | 32.0 | a: 3.21 m | 32.1 |
| | b: 2.81 m | | b: 2.81 m | |
| 2" | 3.66 m | 54.9 | 3.66 m | 54.9 |
| 3" | | 171.1 | | 171.2 |
| OMe | 3.85 s | 55.1 | 3.85 s | 55.0 |

$^a$Assignments interchangeable.

M2' and M2" Give Similar Metabolic Profiles as Parent Compounds 8S and 10S

Metabolic profiles of 8S and 10S in human colon fibroblast cells CCD18Co, human colon cancer cells HCT-116, and HT-29 correlated to the profiles of M2' and M2" in the same respective cell lines, contributing to the identification of M2' and M2" as carriers of their respective shogaols. Upon removal of the cysteine residue, which occurs after less than two hours of treatment, M2' and M2" are metabolized in an almost identical fashion as their parent shogaols. M9 and M11 are the major metabolites of 6S in cancer cells; M11 is the double bond reduced metabolite of 6S; and M9 is the ketone group reduced metabolite of M11. Reduced products were also identified as the major metabolites of 8S and 10S in human colon fibroblast cells and cancer cells, M9' and M11' for 8S and M9" and M11" for 10S (FIG. 1). Their structures were confirmed by comparing their MS/MS spectra with those of M9 and M11.

M2' and M2" Exert Similar Bioactivities as their Parent Compounds 8S and 10S

Figure 14:
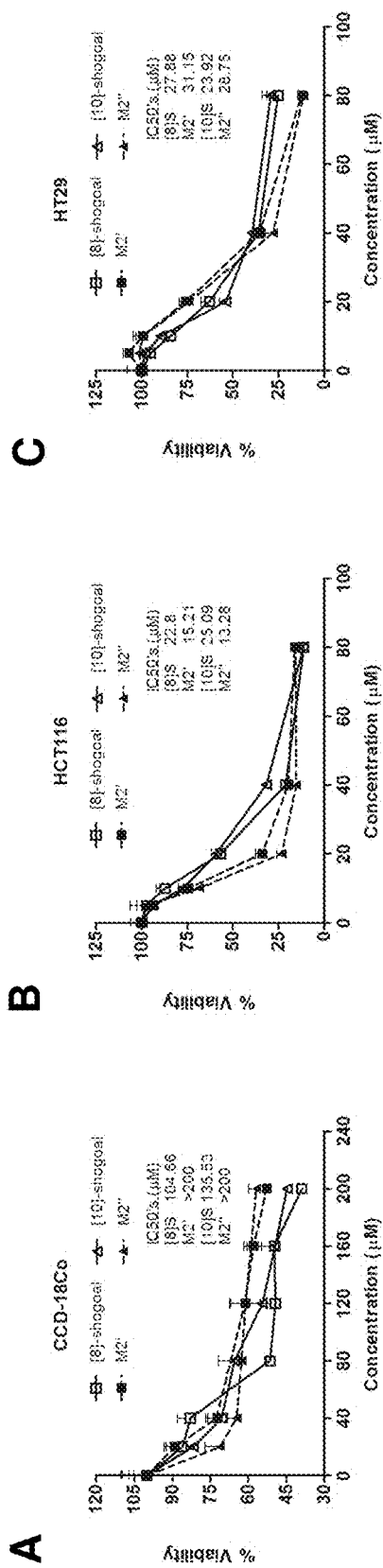
FIG. 14 shows the growth inhibitory effects of 8S, M2', 10S and M2" against human normal colon cells CCD-18Co (A) and human colon cancer cells HCT-116 (B) and HT-29 (C) treated with 8S, M2', 10S or M2" for 24 hours at different doses (n=6) (measured by MTT assay).

The results of the MTT assay show that 8S and 10S and their respective cysteine-conjugated metabolites M2' and M2" have low toxicity in normal colon cells CCD-18Co (FIG. 14A), with IC$_{50}$ values of 104.66 and 135.53 µM for 8S and 10S, respectively, and IC$_{50}$ values greater than 200 µM for M2' and M2". All compounds were highly potent against human colon cancer cells HCT-116 (FIG. 14B) and HT-29 (FIG. 14C), with slightly different efficacy profiles between the two types of cells. M2' and M2" show higher activity against HCT-116 than their parent molecules, with IC$_{50}$ values of 15.21 and 13.28 respectively, versus values of 22.8 and 25.09 for 8S and 10S, respectively. Similar results were observed in the p53 mutant HT-29 cell line, albeit slightly more resistant to treatment from all compounds. The IC$_{50}$ values for 8S and 10S, 27.88 and 23.92 µM, were about 10 to 16% lower than those for M2' and M2", at 31.15 and 28.75 µM, respectively.

M2 Induces Apoptosis in Human Colon Cancer Cells HCT-116 and HT-29

To study the impact of M2 on induction of apoptosis in both HCT-116 and HT-29 colon cancer cells, the percent of apoptotic cells were quantified after 24 hours treatment of increasing doses of M2. A dose-dependent effect of M2 was observed with HCT-116 cells being notably more sensitive to M2 treatment than HT-29 cells. Treatment of 40 µM M2 gave the greatest induction of apoptosis in HCT-116 and HT-29 cells, with 26.34 or 14.38% apoptotic cells, respectively. The 10 and 20 µM treatments also yielded twice as many apoptotic HCT-116 cells compared to HT-29 cells, respectively.

Induction of apoptosis was further confirmed by Western blot analysis of markers of the intrinsic mitochondrial apoptosis pathway. Increasing doses of M2 led to PUMA induction (up to ~17-fold increase in both cell lines when treated with 40 µM M2) and progressive reduction of Bcl-2 levels (undetectable in HCT-116 and ~0.1-fold in HT-29 cells when treated with 40 µM M2). A progressive increase in cytochrome c release with increasing doses of M2 (up to ~2.2-fold increase in both cell lines when treated with 40 µM M2) was observed, as was a clear, progressive reduction in XIAP expression with increasing doses of M2 (undetectable in HCT-116 and ~0.3-fold in HT-29 cells when treated with 40 µM M2). Finally, increasing concentration of the cleaved forms of caspase 9 (up to ~4.6-fold increase in both cell lines when treated with 40 µM M2) and caspase 3 (up to ~3 to 4-fold increase in both cell lines when treated with 40 µM M2) were detected with increasing doses of M2. Without being bound by theory, these results suggest that markers of the mitochondrial pathway (PUMA, Bcl-2) of apoptosis were activated upon exposure to M2, and ultimately led to the release of the corresponding apoptosis markers (cytochrome c, cleaved caspases 3 and 9).

8S, 10S, M2' and M2" Activate Apoptosis

Screening of the markers modulated by the pro-apoptotic activity of M2 gave similar results for 8S and 10S and their respective cysteine-conjugated metabolites M2' and M2". In other words, PUMA, and cleaved caspase-3 were all up-regulated, with concomitant down-regulation of Bcl-2. The changes in markers expression was observed in both cell lines in a nearly identical amplitude between the parent compound and its corresponding metabolite.

Shogaols and its Cysteine-Conjugated Metabolites Affect Wild-Type and Mutant p53 Expression in Human Colon Cancer Cells HCT-116 and HT-29

To study the impact of M2 on p53 regulation in human colon cancer cells and its dependency on p53 integrity, p53 wild-type HCT-116 or p53 mutant HT-29 cells were cultured with M2 or 6S for 24 hours at concentrations of 10, 20, or 40 µM. The p53 response in colon cancer cells to 6S treatment (10, 20, or 40 µM for 24 hours) was observed in HCT-116 and HT-29. After M2 or 6S treatment, a dose-dependent up-regulation of p53 was noted in both wild-type and mutant cancer cell lines, indicating that M2 or 6S regulation of p53 does not require a wild-type gene, although induction of p53 expression by M2 or 6S is dramatic in HCT-116 cells and slightly less striking (but still significant) in HT-29 cells. The expression of p53 in HCT-116 and HT-29 cells after exposure to 20 µM of 8S, M2', 10S or M2" showed an increase in p53 accumulation for all compounds. The cysteine-conjugated metabolites were able to increase p53 accumulation in a similar manner to their parent compound.

6S and its Cysteine-Conjugated Metabolite M2 Affect Reactive Oxygen Species Generation in Human Colon Cancer Cells HCT-116 and HT-29

Figure 15:
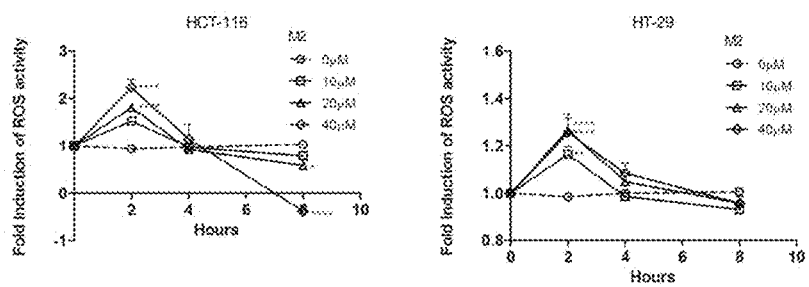
FIG. 15 shows that cysteine conjugated shogaols induce apoptosis via oxidative stress-mediated p53 pathway. Protein levels were relatively quantitated by densitometric analysis using β-actin as a loading control. Fold induction for each marker compared to DMSO is indicated under the corresponding line. Induction of ROS by M2 or 6S. HCT-116 and HT-29 cells were treated with indicated concentrations of 6S or M2 for different time periods, and the intracellular ROS levels were determined as described under Materials and Methods. (* p<0.05,  p<0.01, * p<0.001, and **** p<0.0001)
Figure 15:
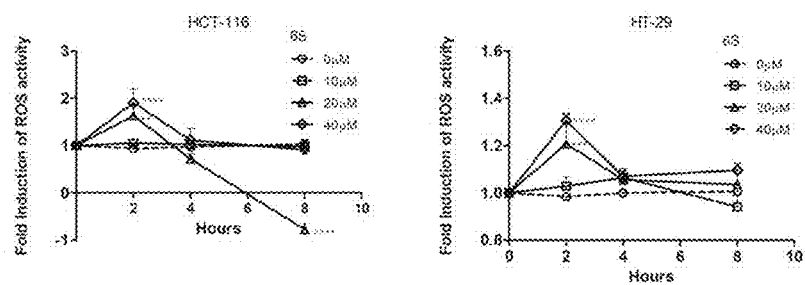

As shown in FIGS. 15A and 15B, the trends of ROS induction by both M2 and 6S are similar, with the greatest peak at 2 hours after treatment and a steady decline thereafter, which is consistent with the changes of glutathione levels in cancer cells. Treatment of HCT-116 cells with 40 µM M2 produced the greatest ROS activity after two hours, with greater than 2-fold induction (with statistical significance, p<0.0001). The scales of induction of ROS by M2 or 6S are parallel to the p53 induction response in the two respective cell lines. That is, in HCT-116 cells, ROS activity is induced 2-fold or greater by M2 or 6S treatment, while in HT-29 cells, ROS activity is induced less than 1.5-fold.

Treatment of HCT-116 and HT-29 cells for 24 hours with M2 or 6S (10, 20, or 40 µM) and supplemented with 5 mM GSH suppressed ROS accumulation in the cells. Addition of GSH suppressed p53 induction in both cell lines for all concentrations of M2 or 6S, suggesting that p53 does not accumulate if there is no ROS generation.

M2 Inhibits Colony Formation in Human Colon Cancer Cells HCT-116 and HT-29

Figure 16:
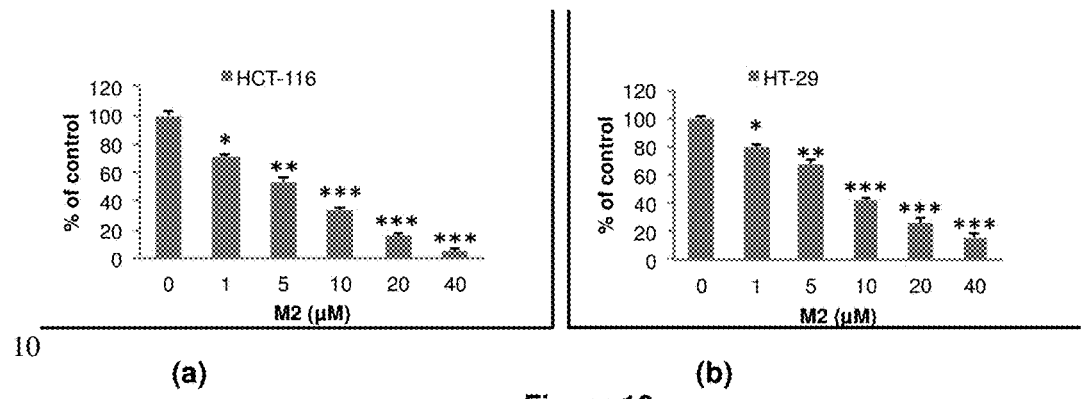
FIG. 16 shows a dose dependent inhibition of human colon cancer cell colony formation by M2 in HCT-116 (A) and HT-29 (B) cells. Cells were treated with M2 (0, 1, 5, 10, 20 and 40 µM) and incubated in 6-well plates for 2 weeks, and the cells were then stained with crystal violet and counted for colony formation. Each column represents a mean±SD (n=3; * p<0.05;  p<0.01; and * p<0.001)

Human colon cancer cells HCT-116 (FIG. 16A) and HT-29 (FIG. 16B) were treated with M2 with doses ranging from 0 to 40 µM for two weeks. Inhibition of colony formation was observed in a dose-dependent manner in both cell lines, with 50% inhibition between 5 and 10 µM treatments. Following a trend underlined previously, HCT-116 cells are slightly more sensitive to M2 than HT-29 cells.

Discussion

[6]-shogaol has been shown herein to be extensively metabolized in mice and in cancer cells. Reduction of xenobiotic carbonyls is a metabolic route to produce more hydrophilic and often less toxic compounds, which can be substrates for phase II conjugation by UDP-glucuronosyl-transferases or sulfotransferases, leading ultimately to excretion of the products. As disclosed herein reduced metabolites were formed in which M11 is the double-bond-reduced metabolite of [6]-shogaol, and M9 and M6 are ketone group-reduced metabolites of M11 and [6]-shogaol, respectively.

The metabolic profiles of shogaols in mouse and in human urine were analyzed using liquid chromatography/electrospray ionization (ESI) tandem mass spectrometry. The structures of major metabolites (FIG. 1) were identified by analyzing the $MS^2$ and $MS^3$ spectra of each compound. The regulation of GSH by [6]-shogaol was also investigated in human colon cancer cells. In particular, the metabolism of [10]-shogaol in mouse urine, was investigated with special focus on the mercapturic acid pathway, and then the formation of thiol-conjugated metabolites of shogaols ([6]-, [8]-, and [10]-shogaols) in human urine was studied. Eight major thiol-conjugated metabolites of [10]-shogaol were detected in mouse urine, while six major thiol-conjugated metabolites of [6]-shogaol, two thiol-conjugated metabolites of [8]-shogaol, and two thiol-conjugated metabolites of [10]-shogaol were detected in urine collected from human after drinking ginger tea, using liquid chromatography/electrospray ionization tandem mass spectrometry. Without being bound by theory, the results indicate the mercapturic acid pathway is a major metabolic route for [10]-shogaol in mice and for shogaols in human. The regulation of glutathione (GSH) by [6]-shogaol in HCT-116 human colon cancer cells was also investigated; [6]-shogaol, after initially depleting glutathione levels, was shown to subsequently restore and increase GSH levels over time.

M2 was shown to substantially retain the biological activities of [6]-shogaol, with an $IC_{50}$ of 24.43 µM in HCT-116 human colon cancer cells and an $IC_{50}$ of 25.82 µM in H-1299 human lung cancer cells. M13 had $IC_{50}$ values of 45.47 and 47.77 µM toward HCT-116 and H-1299 cells, respectively. The toxicity evaluation of the synthetic metabolites (M1, M2, and M4-M13) against human normal fibroblast colon cells CCD-18Co and human normal lung cells IMR-90 demonstrated a detoxifying metabolic biotransformation of [6]-shogaol. The most active metabolite M2 had almost no toxicity to CCD-18Co and IMR-90 normal cells with $IC_{50}$ of 99.18 and 98.30 µM, respectively. TUNEL (Terminal deoxynucleotidyl transferase dUTP nick end labeling) assay indicated apoptosis was triggered by metabolites M2, M13, and its two diastereomers M13-1 and M13-2. There was no significant difference between the apoptotic effect of [6]-shogaol and those of M2 and M13 at 6 hour time point treatment.

Further, the in vitro metabolism of [6]-shogaol was compared among five species using liver microsomes from mouse, rat, dog, monkey, and human. Following incubations with [6]-shogaol, three major reductive metabolites 1-(4'-hydroxy-3'-methoxyphenyl)-4-decen-3-ol (M6), 1-(4'-hydroxy-3'-methoxyphenyl)-decan-3-ol (M9), and 1-(4'-hydroxy-3'-methoxyphenyl)-decan-3-one (M11), as well as two new oxidative metabolites (1E, 4E)-1-(4'-hydroxy-3'-methoxyphenyl)-deca-1,4-dien-3-one (M14) and (E)-1-(4'-hydroxy-3'-methoxyphenyl)-dec-1-en-3-one (M15) were found in all species (See FIG. 1). The kinetic parameters of M6 in liver microsomes from each respective species were quantified using Michaelis-Menten theory. A broad CYP-450 inhibitor, 1-aminobenzotriazole, precluded the formation of oxidative metabolites M14 and M15, and 18β-glycyrrhetinic acid, an aldo-keto reductase inhibitor, eradicated the formation of the reductive metabolites M6, M9, and M11 in all species. Metabolites M14 and M15 were tested for cancer cell growth inhibition and induction of apoptosis and both showed substantial activity, with M14 displaying greater potency than [6]-shogaol.

[6]-shogaol can be metabolized through the mercapturic acid pathway. Initial conjugation with GSH promoted by glutathione transferase gives rise to the corresponding conjugate, and the GSH conjugate undergoes further enzymatic modification: first modification by γ-glutamyltranspeptidase to form the cysteinylglycine conjugate; then alteration by cysteinyl-glycine dipeptidase or aminopeptidase M to form the cysteine conjugate; and finally conversion by N-acetyltransferase to form the N-acetylcysteine conjugate. Both the cysteine and the N-acetylcysteine conjugates act as substrates of cysteine S-conjugate β-ylase, a mainly renal and hepatic enzyme that cleaves the S—C bond in the cysteinyl moiety, thus liberating a thiolated metabolite, which can be further S-methylated by thiol S-methyltransferase to form 5-methylthio-1-(4"-hydroxy-3"-methoxyphenyl)-decan-3-one (M10) or 5-methylthio-1-(4"-hydroxy-3"-methoxyphenyl)-decan-3-ol (M12).

Attention should be paid to the dose administrated as a supplement of a condensed ginger extract. The metabolism of [6]-shogaol in HCT-116 and HT-29 human colon cancer cells, H-1299 human lung cancer cells, and CL-13 mouse lung cancer cells has been evaluated. The results show that [6]-shogaol in cancer cells has a similar metabolic pathway as that in mice. 5-glutathionyl-[6]-shogaol in treated HCT- 116 cells was detected, giving further evidence to the existence of the mercapturic acid pathway. However, secondary metabolites such as cysteinyl, N-acetylcysteinyl, and cysteinylglycinyl conjugates were not observed in the cancer cell lines. Without being bound by theory, it is possibly due to the absence of the enzymes that lead to the loss of the individual amino acids from the GSH conjugate of [6]-shogaol. Over time, the double-bond-reduced product (M11) formed and the ketone group of M11 was reduced to form M9. At 24 h, [6]-shogaol was almost completely converted to M9 and M11 in HCT-116 and H-1299 cells and to M9 in CL-13 cells.

Figure 2:
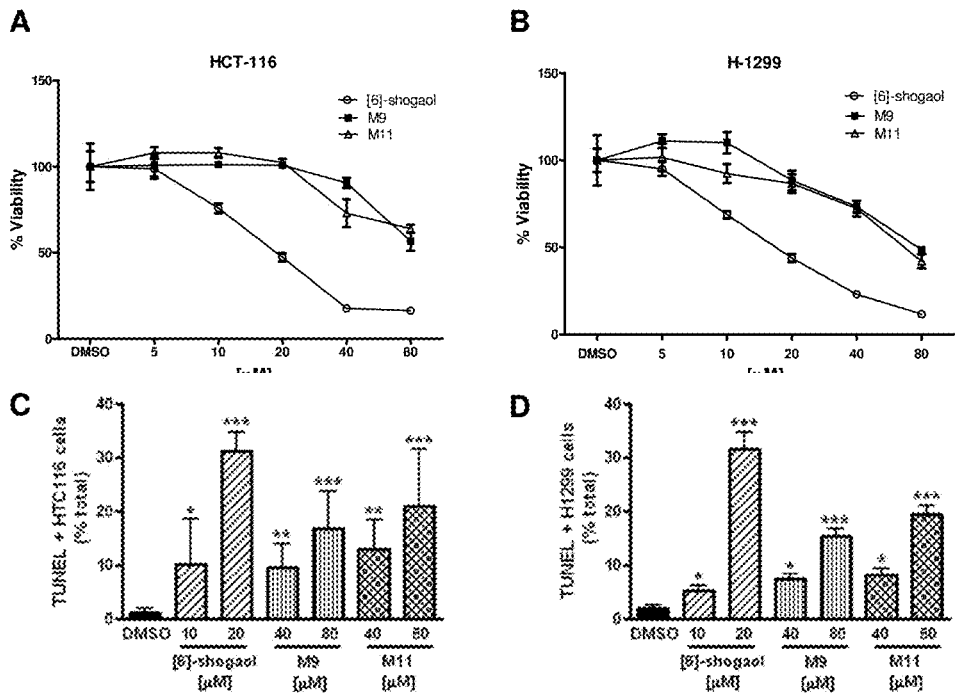
FIG. 2 shows the growth inhibitory effects of [6]-shogaol, M9, or M11 on HCT-116 (A) and H-1299 (B) cells; and effects of [6]-shogaol, M9, or M11 on the induction of apoptosis in HCT-116 (C) and H-1299 (D) cells. MTT assay was used to measure the growth inhibitory effect and each value in A and B represents the mean±S.D. (n=6). TUNEL assay was used to measure the induction of apoptosis and each value in C and D represents the mean±S.E. (n=10). TUNEL-positive cells have been observed at 400× power. Ten fields per slide have been counted and averaged. Significantly different from DMSO control according to the two-tailed Student's t test (*, $p<0.05$, , $p<0.001$, and *, $p<0.0001$).

M9 and M11 both exhibit measurable antiproliferative activity in HCT-116 and H-1299 cancer cells, albeit with less potency than [6]-shogaol (FIGS. 2A and 2B). In addition, M9 and M11 are capable of triggering apoptosis in human colon and lung cancer cells (FIGS. 2C and 2D). [6]-shogaol demonstrated a superior apoptotic effect, so M9 and M11 are at least partially implicated in the stimulation of apoptosis.

The growth inhibitory effects of the synthetic metabolites were compared with [6]-shogaol in two human cancer cells and two human normal cells. Two metabolites, M2 and M13, showed the most comparable growth inhibitory effects to [6]-shogaol towards cancer cells. M2 exhibited a discriminatory effect, that is, it did not seem to be toxic towards normal cells. This effect was not detected with [6]-shogaol. M13 also showed less toxic effects towards normal cells compared to [6]-shogaol. In addition, M5, M6 and M8-M12 also had certain potency against the growth of cancer cells, but showed no toxicity towards normal cells with $IC_{50}$ values greater than 100 µM (FIGS. 3 and 4). Metabolites of [6]-shogaol remain bioactive against cancer cells but are much less toxic than [6]-shogaol to normal cells.

As disclosed herein, TUNEL assay showed that both M2 and M13, but not M6, are capable to induce cancer cell apoptosis in both HCT-116 human colon cancer cells and H-1299 human lung cancer cells (FIGS. 6A and 6B). For M13, apoptosis induction could not firmly be attributed to one isomer or the other, suggesting that stereo configuration is not determinative to the bioactivity of this compound. Both M2 and M13 can trigger apoposis in HCT-116 cells at a level similar to that of [6]-shogaol at the 6 hour time point (FIG. 6C). However, after 24 hours of exposure to the metabolites, the percentage of TUNEL-positive cells was mostly unchanged at 20 µM for both M2 and M13 while the effect of [6]-shogaol was increased. The induction effect of M2 on apoptosis at a concentration of 40 µM increased at the 24 hour time point compared to that of the 6 hour time point, which was higher than that of M13 at a 40 µM concentration. A concentration-dependant effect of [6]-shogaol and its metabolites was observed on cancer cell apoptosis, where an increase in concentration of a compound resulted in a corresponding increased percentage of apoptotic cells.

The metabolite M13 is a mixture of M13-1 and M13-2 and had slightly better growth inhibitory effects on cancer cells than either of the two diastereomers alone. The isomers had similar activity, though M13-2 was slightly more potent than M13-1. M13 was identified as the metabolite of [6]-shogaol in the form of a mixture of M13-1 and M13-2 in HCT-116 human colon cancer cells.

The metabolism of [6]-shogaol is comparable in liver microsomes from mouse, rat, dog, monkey, and human. The spectra were similar across all animal species and the major metabolites were found in all samples, with a few differences—for instance, the ratios and relative abundances of the major metabolites were not conserved. Metabolite M6, which was the dominant peak in spectra from the rodent species after 30 minutes incubation of [6]-shogaol with microsomes, was found in an intermediate relative amount in dog and in human, and was a minor metabolite in monkey. Metabolite M11 was the major product of [6]-shogaol metabolism in HLM, but a very minor product of incubation from microsomes of other species, with minute amounts in MLM and CyLM. The greatest species variegation noted was metabolites M14 and M15: M14 was the major metabolite in CyLM, while the peak produced from this compound was minor in all other species, with the smallest amount produced from HLM incubation; metabolite M15, although present in all species after [6]-shogaol metabolism, was very minor in mouse, rat, and human and was abundant in dog and monkey.

Using a general CYP-450 inhibitor ABT, it was shown that both M14 and M15 were catalyzed predominantly by CYP-450 enzymes, suggesting that the P450 enzymes involved in [6]-shogaol metabolism are not conserved as a function of evolutionary similarity, given the disparity between CyLM and HLM. Genetically, monkey and human have a low relative divergence; however, minute differences in the composition of the CYP enzymes in seemingly familiar species have apparent metabolic consequences.

An α,β-unsaturated ketone such as [6]-shogaol is likely to undergo selective reductive metabolism with initial chain saturation and subsequent reduction to the alcohol metabolite by an aldo-keto reductase. An easily accessible and well known dehydrogenase inhibitor, licorice root derivative 18β-glycyrrhetinic acid (18β-GA), was used to investigate the role of aldo-keto reductase enzymes in [6]-shogaol metabolism in liver microsomes. Administration of 18β-GA inhibited [6]-shogaol metabolism in all species, thereby verifying the assumption that [6]-shogaol reductive metabolism was a function of aldo-keto reductase(s).

To quantify a portion of [6]-shogaol metabolism, the pharmacokinetics of major metabolite M6 formation in MLM, RLM, DLM, CyLM, and HLM was investigated using Michaelis-Menten parameters. The calculated results were consistent with the observed spectra engendered from incubations of each respective species and [6]-shogoal. That is, mouse and rat showed significant preference for M6 formation, both qualitatively and quantitatively, with the largest peak areas for this metabolite and the lowest $K_m$ values after 30 minute incubations with [6]-shogaol. Intrinsic clearance values for these species were also the highest, indicating greater catalytic efficiency. Conversely, monkey liver microsomes produced a small amount of M6, with a matching high $K_m$ value and a low intrinsic clearance value. Human liver microsomes gave intermediate values for $K_m$ and intrinsic clearance, compared to the four species The study of the metabolism of [6]-shogaol in different species provided the opportunity to identify two oxidative metabolites, (1E,4E)-1-(4-Hydroxy-3-methoxyphenyl)deca-1,4-dien-3-one(M14) and (E)-1-(4-Hydroxy-3-methoxyphenyl)dec-1-en-3-one (M15) (FIG. 1). Bioactivity assays showed M14 had a significantly increased potency over [6]-shogaol, in both killing cancer cells and inducing apoptosis, while M15 displayed moderate activity. Without being bound by theory, it appears that the increased potency of M14 can be attributed to the additional double bond on the α,β-unsaturated ketone [6]-shogaol. The double bonds in this compound are thought to be specifically available to sulfhydryl groups via Michael addition and may react by depleting antioxidants such as glutathione. Drastic glutathione depletion is typically an indication of cellular distress and may induce apoptosis. Similarly, as M15 retains an α,β-unsaturated ketone composition similar to [6]-shogaol, it is likely the activity retained by this metabolite can be attributed to this structure. However, in examining the placement of the double bond, the reduced activity is putatively a result of steric hindrance of the benzyl ring against bonding of sulfhydryl groups and subsequent glutathione depletion. Metabolites M14 and M15 induced apoptosis in these cancer cells lines (FIG. 8), indicative of their means of effect against cancer cells.

The cysteine-conjugated 6S (M2), exhibits a cancer cell toxicity similar to the parent compound 6S, but is relatively less toxic towards normal lung cells than 6S. Both compounds can cause cancer cell death by an activation of the mitochondrial apoptotic pathway. The cancer cell toxicity is initiated by early modulation of glutathione (GSH) intracellular content; the generated oxidative stress activates a p53 transcription-independent pathway that ultimately leads to the release of mitochondria-associated apoptotic molecules such as cytochrome C, and cleaved caspases 3 and 9. In a xenograft nude mouse model, a dose of 30 mg/kg of 6S or M2 was able to significantly decrease tumor burden in animals, without any associated toxicity to the animals. This effect correlated with an induction of apoptosis and reduction of cell proliferation in the tumors. 6S and M2 can activate a similar cascade of pathways ultimately leading to cancer cell apoptosis, and that the cysteine-conjugated metabolite has a superior in-vivo cancer chemopreventive potential, in addition to its ability to discriminate between cancer and normal cells, while decreasing tumor burden.

While both compounds displayed a significant toxicity towards A549 cancer cells in the MTT assay, M2 was less toxic towards normal cells, suggesting that the cysteine-conjugation of 6S allowed discrimination between cancerous and normal human lung cells.

6S and its metabolite M2 activate the apoptosis pathway in A549 cells, based on data of the detection of cytoplasmic histone-associated-DNA-fragments upon treatment with 6S or M2 for 24 hours. While the $IC_{50}$ of M2 is higher than 6S, its capacity to specifically induce apoptosis was superior. The final apoptotic markers such as cytochrome C, capases 3 and 9 and their cleaved isoforms are also modulated, while the markers of the Bcl-2 family (Bcl-2, Bak, Bax) were not affected. An early increase in p53 and PUMA, two major actors in the transmission of cellular changes such as (but not limited to) oxidative stress, were observed. Treatment of A549 cells with 6S and M2 led to a disturbance in GSH homeostasis, which would explain the generation of oxidative stress.

When the interaction between Bcl-2 or Bcl-XL and p53 is disrupted using the targeted chemical inhibitor pft, the toxicity of both 6S and M2 is reduced (FIGS. 12B and 12C), as was the induction of apoptosis (FIG. 12D). Without being bound by theory, an apoptotic signal transmitted through the activation of the transcription-independent mitochondrial p53 pathway would explain the lack of variation in the Bcl-2 family markers expression. A marked increase in PUMA expression was observed after 24 hours of exposure to both 6S and M2. PUMA is another molecule that can mediate the p53 apoptotic message through its interaction with members of the Bcl-2 family, suggesting that apoptosis is in part accountable for the death of A549 cells, and that multiple mechanisms inducing apoptosis and/or toxicity in cancer cell toxicity are acting together.

In the xenograft experiment, A549 xenograft cancer cell growth was significantly delayed by both 6S and M2. M2-treated animals showed a further reduction in tumor burden compared to the animals treated with 6S at an equivalent dose of 30 mg/kg body weight. As demonstrated by TUNEL staining of tumor tissues, 6S could still significantly induce apoptosis in-vivo, while M2 was close to significance. Both 6S and M2 decrease cell proliferation. Only 6S at the higher dose was shown to have a significant effect while M2 was close to significance. This is consistent that blocking of the apoptotic pathway through chemical methods in-vitro only partially rescued cells from the toxicity of 6S and M2. Similarly, the percentage of apoptotic cells detected by ELISA could not be entirely restored to DMSO (control)-treated levels, especially at the higher concentration (40 µM) of the compounds, when treated with pft.

Cysteine-conjugated shogaols (M2, M2' and M2") are the major metabolites of [6]-, [8]-, and [10]-shogaol in humans. M2 is a carrier of its parent molecule [6]-shogaol in cancer cells and is less toxic to normal colon fibroblast cells. [8]- and [10]-shogaol have similar metabolic profiles to [6]-shogaol and exhibit similar toxicity towards human colon cancer cells. Analogously, M2' and M2" both show low toxicity against normal colon cells but retain potency against colon cancer cells. Cysteine-conjugated shogaols cause cancer cell death through the activation of the mitochondrial apoptotic pathway. Without being bound by theory, oxidative stress activates a p53 pathway that ultimately leads to PUMA induction, down-regulation of Bcl-2, followed by cytochrome c release, perturbation of inhibitory interactions of XIAP with caspases, and finally caspase 9 and 3 activation and cleavage. A brief screen of the markers attenuated by the proapoptotic activity of M2 revealed similar results for [8]- and [10]-shogaols and their respective cysteine-conjugated metabolites M2' and M2".

An initial reaction between the $\alpha,\beta$-unsaturated ketone functional group of 6S and the cysteine sulfhydryl component of GSH takes place in the MAP, giving rise to the corresponding conjugates. The conjugates then undergo series of enzymatic modifications on the GSH moiety, forming cysteinylglycine-, cysteine-, and finally N-acetyl-cysteine-conjugates. Both 8S and 10S are also metabolized in human through the MAP and the cysteine-conjugated metabolites, M2' and M2" respectively were identified as their major metabolites in human urine. These metabolism products are more water soluble and both less toxic and less pungent than their parent compounds.

M2' and M2" were identified as the major metabolite of 8S and 10S, respectively, from humans upon consumption of ginger tea and are the carriers of 8S and 10S, respectively. The metabolites have similar anti-proliferative activity against human colon cancer cells and less toxicity in normal human colon cells to their respective parent compounds. This portion of Phase II metabolism transforms electrophiles to less reactive and more water-soluble intermediates, thus aiding in their mobility and decreasing their toxicity en route.

M2 treatment has been shown to induce ROS generation that in turn up-regulated p53 expression and induced apoptosis through the mitochondrial pathway. M2 induces apoptosis in both wild-type p53 HCT-116 human colon cancer cells as well as mutant p53 HT-29 human colon cancer cells. Although the p53 pro-apoptotic pathway was exploited for at least some of M2's bioactivity, the metabolite's efficacy was ultimately not compromised by p53 mutation. Without being bound by theory, this suggests that the cysteine-conjugated metabolite of 6S would still be able to activate a p53 apoptotic response even in cancer cells containing mutations of the p53 gene.

Both HCT-116 and HT-29 human colon cancer cells experienced a dramatic down-regulation of Bcl-2 after M2 treatment. Interestingly, PUMA, a transcriptional target of p53, was also up-regulated in both colon cancer cell lines after treatment with M2. Upon a transcriptionally-induced signal from p53, PUMA assists in promoting apoptosis by disrupting the association restraints Bcl-xL exerts on p53, thus liberating the molecule to exert pro-apoptotic activity, but binding to Bcl-xL in the process. This evidence supports the strong role of M2 as a chemopreventive agent against colon cancer cells that induces p53 expression and downstream regulation.

Treatment of colon cancer cells HCT-116 and HT-29 with M2 in this study lead to apoptosis, through early production of reactive oxygen species. Over-abundance of ROS combined with a cancer cell's reduced detoxification ability often leads to oxidative stress sufficient to induce programmed cell death. Apoptosis induced by p53 is at least partially dependent upon accumulation of ROS in the current model, suggesting that M2 causes p53 induction of apoptosis via ROS production in both HCT-116 and HT-29 human colon cancer cells. Since it has been demonstrated that metabolites M2' and M2" activate similar markers of apoptosis and contain the same chemical reactivity as M2, it is reasonable to conclude that these metabolites behave in a similar way and also activate cancer cell apoptosis through ROS induction and the subsequent p53 accumulation. In addition, it was demonstrated that M2 does not exclusively induce cancer cell death through apoptosis and can also influence other major mechanisms such as cell proliferation; it further follows that other cysteine conjugated metabolites originating from the same MAP have that potential as well. It has been shown that cysteine-conjugated shogaols are novel compounds with a putative role as natural pharmaceuticals with low-toxicity, high-potency, and at least partially indifferent to p53 integrity in colon cancer cells.

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed:

1. A method of treating lung cancer in a subject in need thereof, comprising the steps of: administering to said subject a therapeutically effective amount of a compound having the formula:

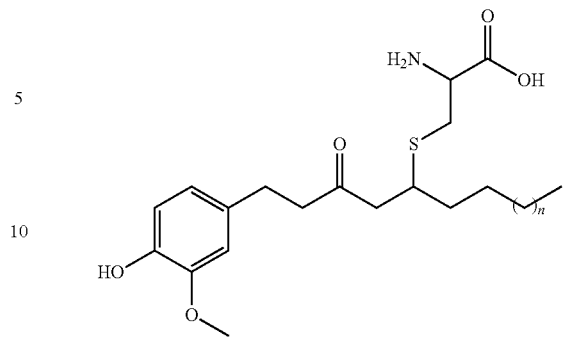

wherein n is selected from the group consisting of 2, 4, 6 and combinations thereof.

2. The method of claim 1 wherein the step of administering a compound having said formula includes the step of including a pharmaceutically acceptable salt or hydrate of said formula.

3. The method of claim 1, wherein said compound is in an isolated or purified form.

4. A method of treating colon cancer in a subject in need thereof, comprising the steps of: administering to said subject a therapeutically effective amount of a compound having the formula:

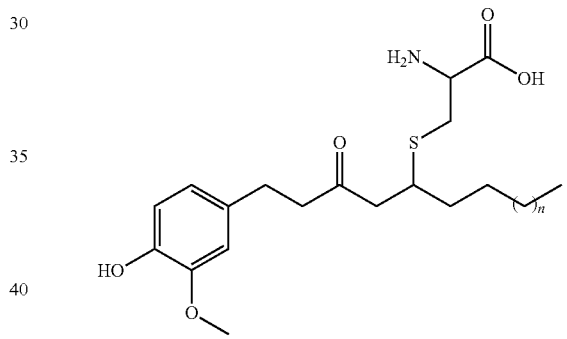

wherein n is selected from the group consisting of 2, 4, 6 and combinations thereof.

5. The method of claim 4 wherein the step of administering a compound having said formula includes the step of including a pharmaceutically acceptable salt or hydrate of said formula.

6. The method of claim 4, wherein said compound is in an isolated or purified form.

7. The method of claim 1 wherein n is 2.
8. The method of claim 1 wherein n is 4.
9. The method of claim 1, wherein n is 6.
10. The method of claim 4, wherein n is 2.
11. The method of claim 4, wherein n is 4.
12. The method of claim 4, wherein n is 6.

* * * * *

UNITED STATES PATENT AND TRADEMARK OFFICE
CERTIFICATE OF CORRECTION

PATENT NO. : 9,549,911 B2
APPLICATION NO. : 15/010011
DATED : January 24, 2017
INVENTOR(S) : Sang et al.

It is certified that error appears in the above-identified patent and that said Letters Patent is hereby corrected as shown below:

On the Title Page

On page 2, item (56), Column right, Line 7, --Rae, K. B.-- should be "Bae, K. B."

In the Specification

In Column 32, Line 10, --R2-- should be "$R^2$"

In Column 32, Line 11, --R2-- should be "$R^2$"

In Column 32, Line 12, --R2-- should be "$R^2$"

In Column 38, Line 33, --R2-- should be "$R^2$"

In Column 38, Line 34, --R2-- should be "$R^2$"

In Column 38, Line 35, --R2-- should be "$R^2$"

In Columns 45 and 46, Table 1, second entry across from 6', --128.3-- should be "120.3"

In Column 50, Line 39, --C===0-- should be "C=0"

In Column 54, Line 18, --C===0-- should be "C=0"

In Column 54, Line 59, --C===0-- should be "C=0"

In Column 55, Line 13, --C===0-- should be "C=0"

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,549,911 B2

In Column 57, Line 30, --C===0-- should be "C=0"
In Column 57, Line 52, --C===0-- should be "C=0"

In Column 65, Line 3, --analyzing the MS'-- should be "analyzing the $MS^n$"

In Column 65, Line 60, --3", 4" -dihydroxyphenyl-- should be "3', 4' -dihydroxyphenyl"

In Column 65, Line 65, --[M + H – $H_2O$]-- should be "[M + H – $H_2O]^+$"

In Column 66, Lines 5-6, --(4"- hydroxy-3"-methoxyphenyl)-- should be "(4'-hydroxy-3'-methoxyphenyl)"

In Column 66, Line 18, --(4"- hydroxy-3"-methoxyphenyl)-- should be "(4'-hydroxy-3'-rnethoxyphenyl)"

In Column 67, Line 61, --OH-3/C-3 and OH-31C-4-- should be "OH-3/C-3 and OH-3/C-4"

In Column 69, at about Line 53, --iv) L-glutathione reduced, NaHCO3 (cat.), MeOH/H2O, rt, 3 h.-- should be "iv) L-glutathione reduced, $NaHCO_3$ (cat.), MeOH/$H_2O$, rt, 3 h."

In Column 71, at about Line 24, --BBr3-- should be "$BBr_3$"

In Column 71, at about Line 26, --NaSCH3-- should be "$NaSCH_3$"

In Column 71 at about Line 28 --NaBH4, CeCl3-7H2O-- should be "$NaBH_4$, $CeCl_3$-$7H_2O$"

In Column 73, Line 7, --α-glutamyl-- should be "y-glutamyl"

In Column 73, Line 17, --HCys-βb[LH 2.73-- should be "HCys-βb [δH2.73"

In Column 73, Line 49, --H-1299 cells with 1050-- should be "H-1299 cells with IC50"

In Column 78, Line 63, --FIG.110-- should be "(FIG. 11C)"

In Column 84, Line 58, --(4"- hydroxy-3"-methoxyphenyl)-- should be "(4'-hydroxy-3'-methoxyphenyl)"

In Column 84, Line 59, --(4"- hydroxy-3"-methoxyphenyl)-- should be "(4'-hydroxy-3'-methoxyphenyl)"

In Column 86, Line 50, --compared to the four species-- should be "compared to the four species."